United States Patent

Walba et al.

[11] Patent Number: 6,139,771
[45] Date of Patent: Oct. 31, 2000

[54] MESOGENIC MATERIALS WITH ANOMALOUS BIREFRINGENCE DISPERSION AND HIGH SECOND ORDER SUSCEPTIBILITY ($X^{(2)}$).

[75] Inventors: David M. Walba, Boulder, Colo.; Daniel J. Dyer, Pasadena, Calif.; Uwe Muller, Berlin, Germany; Peter Cobben, Waalre, Netherlands; Xin Hua Chen, Boulder, Colo.; William Thurmes, Longmont, Colo.; Michael Wand, Boulder, Colo.

[73] Assignee: Displaytech, Inc., Longmont, Colo.

[21] Appl. No.: 08/833,280

[22] Filed: Apr. 4, 1997

[51] Int. Cl.⁷ .......................... C09K 19/52; C09K 19/06; C07D 239/02; C07C 19/08

[52] U.S. Cl. .................. 252/299.01; 252/299.6; 252/299.61; 252/582; 252/299.63; 252/299.2; 544/298; 544/224; 544/242; 546/339; 568/626; 568/647; 570/128; 570/129; 570/144; 585/25

[58] Field of Search .......................... 252/299.63, 299.1, 252/299.62, 582, 299.01, 299.2, 299.61, 299.6; 585/25; 544/298, 224, 242; 546/339; 556/54; 568/626, 647; 570/128, 129, 144

[56] References Cited

U.S. PATENT DOCUMENTS

| | | | |
|---|---|---|---|
| 5,051,506 | 9/1991 | Wand et al. | 544/289 |
| 5,061,814 | 10/1991 | Wand et al. | 549/560 |
| 5,167,855 | 12/1992 | Wand et al. | 252/299.01 |
| 5,178,791 | 1/1993 | Wand et al. | 252/299.6 |
| 5,178,793 | 1/1993 | Vohra et al. | 252/299.61 |
| 5,180,520 | 1/1993 | Wand et al. | 252/299.61 |
| 5,245,456 | 9/1993 | Yoshimi et al. | 359/73 |
| 5,271,864 | 12/1993 | Wand et al. | 252/299.61 |
| 5,380,460 | 1/1995 | Wand et al. | 252/299.6 |
| 5,422,037 | 6/1995 | Wand et al. | 252/299.61 |
| 5,453,218 | 9/1995 | Wand et al. | 252/299.01 |
| 5,457,235 | 10/1995 | Wand et al. | 568/65 |
| 5,580,950 | 12/1996 | Harris et al. | 528/350 |
| 5,635,105 | 6/1997 | Kawata et al. | 252/299.01 |
| 5,649,045 | 7/1997 | Fjare et al. | 385/145 |

FOREIGN PATENT DOCUMENTS

WO92/20058  12/1992  WIPO.

OTHER PUBLICATIONS

Arnett, K.E. et al. (1995), "Technique for Measuring Electronic–Based Electro–Optic Coefficients of Ferroelectric Liquid Crystals," Mat. Res. Soc. Symp. Proc. 392:135–146.
Baena, M.J. et al. (1994), "Ferroelectric Behavior in Metal–Containing Liquid Crystals: A Structure–Activity Study," J. Am. Chem. Soc. 116:1899–1906.

(List continued on next page.)

Primary Examiner—C. H. Kelly
Attorney, Agent, or Firm—Greenlee, Winner & Sullivan, P.C.

[57] ABSTRACT

This invention provides LC compositions useful as birefringent materials in electrooptic devices which exhibit zero or low negatively sloped birefringence dispersion (e.g., exhibiting positive birefringence dispersion significantly lower than that of currently available LC compositions) or more preferably positively sloped birefringence dispersion in which birefringence of the material increases with wavelength. The invention provides compounds useful as components of LC compositions which exhibit negative birefringence where $n_o$ is higher than $n_e$. The compounds of this invention are dimers of LC-like compounds in which the monomers are linked to each other through a high birefringence moiety (dimerization linker). The LC monomers consist of an LC core and one or two tail groups. Preferred monomers for this invention have low birefringence in comparison to the birefrigence of the monomer linking moiety. The dimers have normal positive birefringence dispersion to have birefringence that is lower in absolute value at longer wavelengths. But since they have negative birefringence, their birefringence actually increases (i.e., goes less negative) as wavelength increases.

39 Claims, 4 Drawing Sheets

OTHER PUBLICATIONS

Dyer, D.J. and Walba, D.M. (1994), "Improvement of Thermotropic Liquid Crystallinity by Incorporation of Unsaturated Fatty Alcohol Tail Units," Chem. Mater. 6:1096–1098.

Fouquey et al. (1987), "Liquid Crystals for Non–linear Optics: Mesophases Formed by Push–Pull Stilbenes and Diacetylene," J. Chem. Soc. Chem. Comm. 1424–1426.

Ikeda, T. et al. (1993), "Photochemical switching of polarization in ferroelectric liquid–crystal films," Nature 361:428–430.

Kanis et al. (1994), "Design and Construction of Molecular Assemblies with Large Second–Order Optical Nonlinearities. Quantum Chemical Aspects," Chem. Rev. 94:195–242.

Kobayashi, S. et al. (1990), "New Ferroelectric Liquid Crystals with Very Large Spontaneous Polarization," Mol. Cryst. Liq. Cryst. Lett. 7(4):105–110.

Meyers et al. (1994), "Electric Field Modulated Nonlinear Optical Properties o Donor–Acceptor Polyenes: Sum–Over–States Investigation of the Relationship between Molecular Polarizabilites ($\alpha$, $\beta$, $\gamma$) and Bond Length Alternation," J. Am. Chem. Soc. 116:10703–10714.

Sasaki et al. (1994), "Photochemical Control of Properties of Ferroelectric Liquid Crystals: Photochemical Flip of Polarization," J. Am. Chem. Soc. 116:625–628.

Schmitt, K. et al. (1993), "Strongly non–linear optical ferroelectric liquid crystals for frequency doubling," Liq. Cryst. 14(6):1735–1752.

Sonogashira, K. et al. (1975), "A Convenient Synthesis of Acetylenes: Catalytic Substitutions of Acetylenic Hydrogen with Bromoalkenes, Iodoarenes, and Bromopyridines," Tet. Lett. 50:4467–4470.

Stephens, R.D. and Castro, C. (1963), "The Substitution of Aryl Iodides with Cuprous Acetylides. A Sunthesis of Tolanes and Heterocyclics," J. Org. Chem. 28:3313–3315.

Vtyurin, A.N. et al. (1981), "Study of Optical Second Harmonic Generation in Ferroelectric Liquid Crystal," Phys. Stat. Sol. B 107:397–402.

Walba, D.M. et al. (1991), "Ferroelectric Liquid Crystals Designed for Electronic Nonlinear Optical Applications," Materials for Nonlinear Optics. Chemical Perspectives, ACS Symposium Series 455, Marder et al. (eds.) American Chemical Society, Washington, D.C., pp. 484–496.

Walba, D.M. (1991), "Ferroelectric Liquid Crystals. A Unique State of Matter," in *Advances in the Synthesis and Reactivity of Solids*, vol. 1, JAI Press Ltd., pp. 173–235.

Walba, D.M. et al. (1989), "Design and Synthesis of New Ferroelectric Liquid Crystals. 9. An Approach to Creation of Organic Polymer Thin Films with Controlled, Stable Polar Orientation of Functional Groups," J. Am. Chem. Soc. 111:8273–8274.

Walba, D.M. et al. (1991), "Design and Synthesis of New Ferroelectric Liquid Crystals. 14. An Approach to the Stereocontrolled Synthesis of Polar Organic Thin Films for Nonlinear Optical Applications," J. Am. Chem. Soc. 113:5471–5474.

Walba, D.M. et al. (1991), "Design and Synthesis of Ferroelectric Liquid Crystals. 15. FLC Materials for Nonlinear Optics Applications," Ferroelectrics 121:247–257.

Walba, D.M. et al. (1991), "An Approach to the Design of Ferroelectric Liquid Crystals with Large Second Order Electronic Nonlinear Optical Susceptibility," Mol. Cryst. Liq. Cryst. 198:51–60.

Walba, D.M. et al., "Orientation of the Disperse Red 1 Chromophore Along the Polar Axis in Ferroelectric Liquid Crystals," Abstract for FLC–95, pp. 425–426, 1995.

Walba, D.M. (1995), "Fast Ferroelectric Liquid–Crystal Electrooptics," –251 Science 270:250.

Williams, D.J. (1984), "Organic Polymeric and Non–Polymeric Materials with Large Optical Nonlinearities," Angew. Chem. Int. Ed. Engl. 23:690–703.

Pelzl, G. and Sackmann, H. (1971), "Birefringence of Smectic Modifications of the Homologous Thallium Soaps," Mol. Cryst. Liq. Cryst. 15:75–87.

MESOGENIC MATERIALS WITH ANOMALOUS BIREFRINGENCE DISPERSION AND HIGH SECOND ORDER SUSCEPTIBILITY ($X^{(2)}$).

This invention was made at least with partial funding from the U.S. Government through the Office of Naval Research, and the National Science Foundation. The United States Government may have certain rights in this invention.

FIELD OF THE INVENTION

This invention relates to compounds and liquid crystal compositions containing them which are useful in electooptical and non-linear optical applications.

BACKGROUND OF THE INVENTION

Liquid crystal (LC) displays are now nearly ubiquitous in our culture, being used in both monochrome and color displays in a variety of products from watches to automobile gauges and from road signs to computer displays. It is most desirable that monochrome displays are simply black and white with no particular cast of color. Similarly, it is imperative for quality color displays that all colors be transmitted equally well. If a display is less transmissive for one wavelength compared to another, the display will not show true colors and will be less marketable than a display showing true colors.

LC displays rely on the birefringence (Δn) of the LC, i.e., the difference in refractive indices between different orientations of the LC. Birefringence, $\Delta n = n_e - n_o$, where $n_e$ is the index of refraction along the extraordinary axis of a birefringent material (parallel to the optic axis) and $n_o$ is the index of refraction its ordinary axis (perpendicular to the optic axis). The optimal thickness of an LC cell such that it behaves as a half-wave plate, to maximize contrast and true color transmission, at a given wavelength is proportional to the birefringence. The optimal birefringence for a fixed pathlength, i.e., thickness of LC, increases with increasing wavelength as shown in FIG. 1. In contrast, birefringence of a given material generally decreases as a function of increasing wavelength (FIG. 1). The change in birefringence of a material as a function of wavelength is called birefringence dispersion. (Herein, the term "positive birefringence dispersion" is used for birefringence that decreases with increasing wavelength and "negative birefringence dispersion" is used for birefringence dispersion that decreases with increasing wavelength.) Thus, if birefringence of an LC cell is optimized for transmission at one wavelength by optimization of cell thickness, it will not be the optimal birefringence at a second wavelength and as a consequence light transmission through the cell at the second wavelength will be lower.

Typically, in designing an LC device, a compromise is made by setting cell thickness for optimal transmission of a wavelength in the middle of the operational wavelength range (i.e., at the design wavelength). For LC devices used in the visible, cell thickness is chosen to optimize transmission of green light, giving a cell less than optimal, but useful, transmission in the red and blue. Such a cell has a slight yellow or green cast.

If the birefringence dispersion of an LC material were negative (increasing in slope as a function of increasing wavelength), cells made from this material would exhibit significantly less chromatic behavior. In general, LC materials, i.e. mesogenic compositions, which exhibit a lower positive (including zero) or negative birefringence dispersion than existing materials will be useful for decreasing the chromatic behavior of LC displays and related electrooptical devices. Such mesogenic materials will be useful in optical filters with improved color balance, larger free spectral range, maintaining high resolution with fewer filter stages and in tunable Fabry-Perot filters using liquid crystal spatial light modulators (SLMs).

Furthermore, ferroelectric liquid crystals (FLCs) used in displays often have quite high birefringence requiring the use of thin cells. When thin LC cells are used, small variances in cell thickness can have a significant effect on the cell's optical properties. For example, a 0.1 μm variance in thickness of a cell that is 1.1 μm thick results in a ±9% difference in transmission, while the same variance in a thicker 1.9 μm cell results in only a ±5% difference. Thinner LC cells also tend to suffer from non-uniform spacing, which can lead to shorts. Environmental contamination of LC cells, for example by inclusion of dust and other contaminants, has a more severe effect on thinner cells. Designs using thicker cells, for more stability, easier manufacturing and lower cost, require LC materials with generally lower birefringence (compared to presently available materials). There is a general need in the art for LC materials, particularly FLC materials, with decreased birefringence.

Ferroelectric liquid crystals (FLCs) are true fluids possessing thermodynamically stable polar order. As the liquid crystal cools from a normal isotropic liquid to a crystalline state, it passes through a series of mesogenic phases of increasing order. A typical phase sequence includes several phases, of which only the tilted smectic C* ($S^*_c$) phase possesses the thermodynamically stable polar order necessary to exhibit a net dipole moment. In the $S^*_c$ phase the molecules self-assemble into layers, with the long axis of the molecules coherently tilted with respect to the layer normal. The single polar axis of the phase is normal to the tilt plane. For most such FLCs, a spontaneous macroscopic dipole density or spontaneous ferroelectric polarization P along the polar axis is easily measurable.

The ferroelectric nature of a C* phase affords a very strong coupling of the molecular orientation with external fields, leading to a high contrast electro-optic light valve with fast response relative to the well known nematic devices currently in use. The complicating factor of the C* helix was solved with the invention of the Surface Stabilized Ferroelectric Liquid Crystal (SSFLC) light valve. In the SSFLC geometry, the helix is spontaneously unwound due to surface interactions with bounding glass plates. In this case, when the director prefers a parallel orientation with respect to the surface plates, two states are allowed. In one state the molecules tilt right by tilt angle θ, while in the other state they tilt left. In both cases, the ferroelectric polarization vector is pointing normal to the title plane (normal to the surface of the glass plates).

Due to the birefringence of FLC molecules, the two states have different optical characteristics. When the tilt angle θ=22.5°, and the thickness of the cell is tuned correctly relative to the birefringence, then the cell behaves as a half wave plate, and can be aligned between crossed polarizers such that one state gives good transmission, while the other state shows good extinction, giving rise to the desired electro-optic effect.

SSFLC cells show very high contrast (1,500:1 demonstrated), low switching energy, bistability, high resolution (≅$10^7$ pixels/cm$^2$ demonstrated, $10^8$ pixels/cm$^2$ possible) and other performance characteristics which make it particularly attractive for many optoelectronic applications.

Compounds which self-assemble into the smectic C phase are often termed C phase mesogens. While there is currently no detailed understanding of the relationship between molecular structure and the occurrence of LC phases, empirically, C phase mesogens generally possess a rigid core separating two "floppy" tails. The tails of chiral and achiral mesogens can include a variety of chemical functionalities, but components of commercial mixtures often have one or two alkyl or alkoxy tails. The tails often have similar lengths, and both are typically longer than four carbons. Many compounds of this type also exhibit a nematic phase. For C* mesogens generally one of the tails will possess one or more tetrahedral stereocenters.

In order to be useful in the many types of devices of interest, FLC materials must possess properties never achievable in a single compound, but the stable temperature range and other material parameters can in general be tuned by mixing components. Commercial LC mixtures are generally composed of at least eight components. FLC mixtures generally contain two types of components: 1) A smectic C host, designed to afford the required temperature range and other standard LC properties; and 2) Chiral components designed to induce ferroelectric polarization and produce fast switching or other desirable properties (e.g., tilt angle adjustment)in the FLC film. FLC mixture may also contain additional achiral components that adjust other desirable FLC properties.

Birefringence refers to the property of a liquid crystal to interact more strongly with light along one LC axis than along another LC axis. As discussed above, most LCs are made of a core with extensive electron delocalization, to which one or two tails are attached to help orient the molecules, give a dipole moment or polarization or confer other desirable properties on the molecule. Typical LC are rod-shaped with the majority of the pi-electron delocalization along the long or extraordinary axis (also referred to as the director). As a consequence the extraordinary axis of LCs have the higher index of refraction, so their birefringence $\Delta n = n_e - n_o$ is positive. Birefringence of a liquid crystal at a given wavelength is:

$$\Delta n = G(T) \frac{\lambda^2 \lambda^{*2}}{\lambda^2 - \lambda^{*2}},$$

where $\Delta n$ is the birefringence at a given wavelength, G is a constant, T is the temperature, $\lambda$ is the particular wavelength, $\lambda^*$ is the mean resonance frequency which can be calculated given the spectrum of a material or the its birefringence at several wavelengths. See: S. -T. W (1986) Phys. Rev. A 33:1270; S. -T. W (1987) Opt. Eng. 26:120; S. -T. W, C. -S. W (1989) J. Appl. Phys. 66:5297; S. -T. W et al. (1993) Opt. Eng. 32:1775. As the wavelength of interest moves away from $\lambda^*$, the birefringence decreases asymptotically until in the infrared, the birefringence is relatively constant (except near IR absorbencies). There is, however, a large amount of birefringence dispersion in the visible spectrum. This is particularly true if $\lambda^*$ is close to the visible region so that $\lambda^2 - \lambda^{*2}$ is small. While the birefringence of the typical LC is higher at short wavelengths than at longer wavelengths, optimization of LC cells as half-waveplates at a given wavelength generally require the opposite behavior of birefringence as a function of wavelength. FLC cell half-wave plates in particular require:

$$d = \frac{\lambda}{2 \Delta n}$$

where a wavelength ($\lambda$) of about 500 nm is usually chosen as the optimal for LC cells (for applications in the visible). As indicated in FIG. 1, this thickness is then not optimal for all wavelengths of visible light due to the birefringence dispersion.

FIG. 2 shows transmission (measured and calculated) at different wavelengths for cells with three different FLC materials (a standard mixture and two theoretical mixtures), normalized for 100% transmission of 500 nm light. The first measured transmission (solid line) is ZLI 3654 which has typical birefringence behavior with a $\lambda^*$ of 217 nm. With this mixture, only about half of the 400 nm light and about 70% of the 700 nm is transmitted. A cell using this material has a noticeable greenish cast. The second, a calculated transmission (dotted line) is that based on use of a theoretical material in which the birefringence is invariant with changing wavelength. A cell using such a material is calculated to transmit about 83% of 400 nm light and about 83% of 700 nm light. Such a cell would have much truer color, particularly in the blue, compared to the standard FLC cell. The third, another calculated transmission (dashed line) is that based on use of a theoretical material in which the birefringence dispersion is negative, with the absolute value of the proportional change as a function of wavelength the same as for the standard LC mixture. A cell using such a material is calculated to transmit very nearly 100% of blue light and 92% of red light, resulting in a cell with quite true colors.

The present invention relates in one aspect to low birefringence mesogens or to mesogens having anomalous birefringence dispersion. As used herein, "anomalous" refers to birefringence dispersion atypical for liquid crystal material, either exhibiting zero (as illustrated in FIG. 2 dotted line) or negative birefringence dispersion (increasing with increasing wavelength) (as illustrated in FIG. 2 dashed line), or significantly less positive birefringence dispersion compared to known LC materials. Compounds of this invention can be mesogens or can be employed as components in mesogenic compositions to lower birefringence or to lower birefringence dispersion.

Mesogenic materials of the present invention are chiral nonracemic and achiral materials having mesogenic phases (LC phases) useful in electrooptical devices, including chiral and achiral tilted smectic phase materials (particularly smectic C and smectic A materials) and nematic phase materials. Mesogenic materials of this invention include those that are ferroelectric liquid crystals (FLCs), nematic liquid crystals, and materials useful in SSFLC, electroclinic and DHF devices.

While the discussion of anomalous birefringence dispersion herein has focused on FLC's used in SSFLC devices, other electrooptic devices employing LCs, such as nematic cells will also benefit from the use of LC's with low or negative birefringence dispersion (and more generally from LCs with low or negative birefringence). The mechanism of FLC and nematic cells differ, but in both cases optimization of cell thickness depends on the wavelength of light being transmitted. In nematic cells some efforts have been made to make cells achromatic. For example, a combination of at least two polymer retarder films can be employed as compensators to give light that is reasonably achromatic (T. Scheffer, J. Nehring (1995) SID Seminar Lecture Notes, Vol. 1, M2). However, the use of such external means of chromaticity compensation can be detrimental to contrast ratio or viewing angle of the device. Thus, nematic liquid crystals with little or no birefringence dispersion would be quite beneficial.

Development of methods for creation of organic thin films with large $\chi^{(2)}$ is a problem of great interest due to the potential utility of such films in the fabrication of fast integrated electro-optic (EO) modulators. Such modulators are hybrid devices wherein the organic material must work in concert with semiconductor integrated circuits. For this application the material design and synthesis task involves three key considerations:

1) Molecules with large molecular second order susceptibility $\chi$ must be created; 2) The molecules must be assembled into a material with the correct supermolecular stereochemistry to afford the required bulk $\chi^{(2)}$; and 3) This material must be integrated with a semiconductor device—a key process requiring supermolecular stereocontrol on a more global level.

Early in the development of chiral smectic FLC chemistry and physics, the spontaneous thermodynamically stable polar supermolecular structure exhibited by these anisotropic liquids suggested their potential utility in second order nonlinear optics applications. This work, however, showed that FLCs known at the time, such as DOBAMBC, exhibited values of $\chi^{(2)}$ too small to be useful ($d_{eff}$~0.001 pm/V for SHG from 1064 nm light). Efforts directed toward design of FLCs with increased $\chi^{(2)}$ provided materials with demonstrated EO coefficients on the order of 1 pm/V for modulation of 633 nm light at 100 MHz and d coefficients on the order of 5 pm/V for SHG (Arnett et al. (1995) "Technique for Measuring Electronic-Based Electro-Optic Coefficients for Ferroelectric Liquid Crystals" in Thin Films for Integrated Optics Applications, Wessels et al. (eds), Materials Research Society (Pittsburg, Pa.); Walba et al. (1991) Ferroelectrics 121:247; Schmitt, K. et al. (1993) Liq. Cryst. 14:1735). Still, further increases in the magnitude of $\chi^{(2)}$ are required, since EO coefficients on the order of 50 pm/V are desirable for fast integrated optics applications (Walba, D. M. (1995) Science 270:250). Achieving such a large increase in $\chi^{(2)}$, however, seems problematical in FLCs since functional arrays with large molecular susceptibility $\beta$ are typically "long," and tend to orient along the director when incorporated into traditional thermotropic liquid crystal (LC) structures. Since the FLC polar axis is normal to the director, small values of $\chi^{(2)}$ result as observed for DOBAMBC.

Achieving large $\chi^{(2)}$ in FLCs involves orientation of "large $\beta$" functional arrays, typically possessing two rings and a conjugating spacer unit, along the polar axis with a high degree of supermolecular stereocontrol (Williams, D. J. (1984) Angew. Chem. Int.

Ed. Engl. 23:690; *Quantum Chemical Computational calculations of Nonlinear Susceptibilities of Organic Materials;* Bredas, J. L. et al.(eds.); Special Issue of Mol. Cryst. Liq. Cryst. Sci. Technol. Sect. B, Gordon & Breach (1994) 6(3–4):135; Kanis et al. (1994) Chem. Rev. 94:195; Meyers et al. (1994) J. Am. Chem. Soc. 116:10703.) Excellent supermolecular stereocontrol is indeed achievable in FLCs (on the order of 60% polar excess has been demonstrated as evidenced by ferroelectric polarization measurements), and "large d" functional arrays are easily incorporated into LC structures (Kobayashi et al. (1990) Mol. Cryst. Liq. Cryst. Letts. 7:105; Fouquey et al. (1987) J. Chem. Soc. Chem. Comm. 1424; Berdague et al. (1993) Liq. Cryst. 14:667; Ikeda et al. (1993) Nature 361:428; Sasaki et al (1994) J. Am. Chem. Soc. 116:625). However, in all know cases such functional arrays orient along the liquid crystal director n, while the FLC polar axis is normal to the director.

This invention relates in a second aspect to LC compounds for NLO applications. While an LC mesogen is not required for NLO FLCs (doping of achiral C phase hosts with appropriate non-mesogenic quests delivers the required supermolecular stereocontrol) mesogenicity is desirable since for NLO applications achieving the highest possible concentration of NLO active units is advantageous. Certain compounds of this invention that have negative birefringence also exhibit NLO properties. Herein we demonstrate an approach for achieving large $\chi^{(2)}$ in FLCs with examples of a class of chiral smectic materials demonstrating orientation of large $\beta$ NLO chromophores along the polar axis.

WO 92/20058 (Walba et al.) published Nov. 12, 1992 relates to ferroelectric liquid crystal materials for nonlinear optics applications. Certain of the compounds reported therein are monomers for the side-by-side dimer materials of this invention. WO 92/20058 takes priority from U.S. patent application Ser. No. 07/690,633 filed Apr. 24, 1991 (now abandoned). U.S. patent application Ser. No. 08/137,093, filed Oct. 18, 1993, (now allowed) is the U.S. national stage application of WO 92/20058. WO 92/20058, U.S. Ser. No. 07/690,633 and U.S. Ser. No. 08/137,093 are incorporated in their entirety by reference herein.

The following U.S. patents provide general descriptions of LC's for electrooptical applications, including FLCs: U.S. Pat. Nos. 5,051,506, 5,061,814, 5,167,855, 5,178,791, 5,178,793, 5,180,520, 5,271,864, 5,380,460, 5,422,037, 5,453,218, and 5,457,235. These patents are incorporated by reference in their entirety herein and provide methods of synthesis for a variety of LC materials, including methods of synthesis of a variety of LC cores and chiral and achiral LC tails that are used in the compounds of this invention. These patents also provide a general description of the properties of LC materials for electrooptical applications, particularly those for use in SSFLC, electroclinic, DHF and nematic devices.

SUMMARY OF THE INVENTION

This invention provides mesogenic compositions which exhibit anomalous dispersion. More specifically this invention provides LC compositions useful as birefringent materials in electrooptic devices which exhibit zero or low negatively sloped birefringence dispersion (e.g., exhibiting positive birefringence dispersion significantly lower than that of currently available LC compositions) or more preferably positively sloped birefringence dispersion in which birefringence of the material increases with wavelength. As a means to this end, the invention provides compounds useful as components of LC compositions which exhibit negative birefringence where no is higher than $n_e$. These compounds can be doped into LC compositions having typical positive birefringence dispersion to reduce that dispersion. LC compositions with reduced birefringence dispersion can be used to make LC cells and other electrooptical devices having decreased chromaticity. Preferred compounds of this invention with negative An are those that mix with available FLC and/or nematic mixtures with minimal suppression of the desired mesogenic phases.

Additionally, this invention provides LC electrooptic devices having optical retardance substantially independent of wavelength. The invention particularly relates to LC electrooptic devices for use in the visible.

In a second aspect certain of the dimers of this invention have useful NLO properties.

Most generally, the compounds of this invention are dimers of LC-like compounds in which the monomers are linked to each other through a high birefringence moiety (dimerization linker). The LC monomers consist of an LC core and one or two tail groups. Preferred monomers for this invention have low birefringence in comparison to the birefrigence of the monomer linking moiety. The monomers are linked to each other such that the relatively low birefringence groups, with little conjugation, comprise the long axis of the molecule and the high birefringence linking moiety is substantially perpendicular to that low birefringence long axis. This long axis preferably aligns with the director. These dimers, have more extensive conjugation and high birefringence along the ordinary axis and as a consequence exhibit negative birefringence. The dimers have normal positive birefringence dispersion, to have birefringence that is lower in absolute value at longer wavelengths. But since they have negative birefringence, their birefringence actually increases (i.e., goes less negative) as wavelength increases.

A particularly interesting subset of compounds of this invention are those having negative birefringence and which exhibit strong absorption bands near, but not in the visible. These materials exhibit negative birefringence and birefringence dispersion that slopes steeply in the blue portion of the spectrum. The $\lambda^*$ of a material can be adjusted by changing functional groups in the high birefringence linker between monomers. Substitution with functional groups including among others, nitro groups, azo groups, Shiff bases, ketones, sulfonates, thiols, and amines can be employed to adjust absorption spectrum of the compounds of this invention.

When mixed into standard LC materials with positive birefringence dispersion, compounds of this invention with negative birefringence result in mixtures having reduced birefringence dispersion or negative birefringence dispersion.

Compounds of this invention include those of formula I:

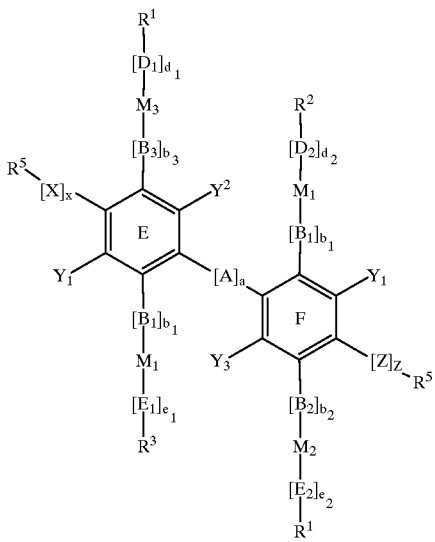

where a is 0 or 1 and A is selected from the group consisting of a —C=C—, —C≡C—, —C≡C—C≡C—, —C=C—C=C—, —C≡C—C=C—C≡C—, —N=N—, —N=NO—, and a —HC=N— group;

$b_1$–$b_4$, independently of one another, are 0 or 1 and $B_1$–$B_4$, independently of one another, are selected from the group consisting of —C=C—, —C≡C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—;

$d_1$ and $d_2$, independently of one another, are 0 or 1 and $D_1$ and $D_2$, independently of one another, are selected from the group consisting of —C=C—, —C≡C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—;

$e_1$ and $e_2$, independently of one another, are 0 or 1 and $E_1$ and $E_2$, independently of one another, are selected from the group consisting of —C=C—, —C≡C—, —COO—, —OOC—, —CO—, —O—, —CH$_2$—, —OCH$_2$—, —CH$_2$—CH$_2$—, —S—, —COS—, —SOC—, —CH=CHCOO—, —OOCCH=CH—, —CH=CHCOS—, and —SOCCH=CH—;

six-membered aromatic rings E and F, independently of one another, are phenyl rings or phenyl rings in which one or two of the carbon atoms of the ring are replaced with nitrogen atoms and wherein the carbon atoms of the phenyl or nitrogen-containing phenyl rings can be substituted with a halogen, CN, NO$_2$, alkyl, alkenyl, alkynyl, haloalkyl, haloalkenyl, or haloalkynyl group (preferred halogens being fluorines);

$Y_1$–$Y_4$, substituents on rings E and F, independently of one another, are selected from the group consisting of H, halogen, CN, alkyl, alkenyl, alkynyl, haloalkyl, haloalkenyl, or haloalkynyl group (preferred halogens being fluorines) wherein one or more non-neighboring CH$_2$ groups in the substituent can be substituted with an O, or S (e.g., giving alkoxy, ether, thioether or related groups) or with a SiR$^A$R$^B$ group, where R$^A$ and R$^B$ are small alkyl or alkenyl groups having from 1 to about 6 carbon atoms, with the proviso that any ring position of aromatic rings E or F that is a nitrogen is not substituted with any of the $Y_1$–$Y_4$;

x and z, independently of one another are 0 or 1, and X and Z, independently of one another, are selected from the group consisting of electron acceptor groups, electron donor groups, H, halogen, NO$_2$, —C=C—, —C≡C—, —COO—, —OOC—, —CO—, O, S, —COS—, —SCO—, CN, NH, NCH$_3$ (more generally NR', where R' is a small alkyl having 1 to about 3 carbon atoms), NHCO, NCH$_3$CO (more generally NR'CO, where R' is a small alkyl having 1 to about 3 carbon atoms), SO, and SO$_2$, with the proviso that any ring position of aromatic rings E or F that is a nitrogen is not substituted with any X or Z, and R$^5$ and R$^6$, independently of one another, are selected from the group consisting of H, halogen, CN, alkyl, alkenyl, alkynyl, haloalkyl, haloalkenyl, or haloalkynyl group (preferred halogens being fluorines) wherein one or more non-neighboring CH$_2$ groups in the substituent can be substituted with an O, or S (e.g., giving alkoxy, ether, thioether or related groups) or with a SiR$^A$R$^B$ group, where R$^A$ and R$^B$ are small alkyl or alkenyl groups having from 1 to about 6 carbon atoms, dependent upon the X or Z group, R$^5$ and/or R$^6$ may be absent; and $M_1$–$M_4$, independently of one another, are core moieties having from one to four aromatic or non-aromatic rings, optionally separated by up to three linking groups $F_1$–$F_3$ as in formula:

where f1–f4, independently of one another, are 0 or 1, $F_1$–$F_4$, independently of one another, are selected from the group consisting of —C=C—, —C≡C—, —COO—, —OOC—, —CO—, —O—, —CH₂O—, —OCH₂—, —CH₂—CH₂—, —S—, —COS—, —SOC—, —CH=CHCOO—, —OOCCH=CH—, —CH=CHCOS—, and —SOCCH=CH—; and n1–n4, independently of one another, are 0 or 1, and $N_1$–$N_4$ are selected from the group consisting of aromatic rings having one or two six-member and/or five-membered aromatic rings, which may be fused or non-fused ring systems, or monocyclic or bicyclic alkyl and alkenyl non-aromatic rings having from 5 to about 12 ring carbon atoms wherein in each ring of $N_1$–$N_4$, one or more of the ring carbons can be substituted with a halogen, CN, small alkyl, alkenyl or alkynyl group having from 1 to about 3 carbon atoms or small halogenated alkyl, halogenated alkenyl or halogenated alkynyl having from 1 to about 3 carbon atoms preferred halogens being fluorines), in each ring of $N_1$–$N_4$ that is aromatic, one or two of the ring carbons can be replaced with a nitrogen (N), in each ring of $N_1$–$N_4$ that is non-aromatic, one or two non-neighboring CH₂ groups can be replaced with an oxygen; and $R^1$, $R^2$, $R^3$, and $R^4$, independently of one another, are selected from the group consisting of linear, branched or cyclic alkyl, alkenyl or alkynyl groups having from 1 to about 20 carbon atoms wherein one or more CH₂ groups can be optionally substituted with one or more halogens, or CN groups, or in which one or more non-neighboring CH₂ groups can be replaced with an oxygen, a sulfur, or a substituted silyl group, $Si(R^A)(R^B)$, in which $R^A$ and $R^B$, independently, are alkyl, alkenyl, alkynyl, haloalkyl, haloalkenyl or haloalkynyl groups, preferably those having from 1 to about 6 carbon atoms (preferred halogens being fluorines).

$R^1$, $R^2$, $R^3$, and $R^4$ groups can be chiral nonracemic groups or achiral groups dependent upon the desired application of the compound. A subset of $R^1$–$R^4$ groups are fully or partially fluorinated alkyl, alkenyl or alkynyl groups, designated by RF Preferred $R^1$–$R^4$ include those that have about 6 to about 12 carbons. Preferred $Y_1$–$Y_4$ that are alkyl, alkenyl, alkynyl or halogenated derivatives thereof are those that have from 1 to about 6 carbon atoms. Preferred $R^5$ and $R^6$ that are alkyl, alkenyl, alkynyl or halogenated derivatives thereof are those having from 1 to about 6 carbon atoms.

Preferred $N_1$–$N_4$ are aromatic rings having one six-member aromatic ring and monocyclic or bicyclic alkyl and alkenyl non-aromatic rings having from 5 to about 12 ring carbon atoms. More preferred monocyclic non-aromatic rings are cyclohexane and cylcohexene rings.

X and Z groups can include electron donor groups and/or electron acceptor groups as defined herein below.

In general herein, unless otherwise stated alkyl, alkenyl and alkynyl groups can contain linear, branched or cyclic portions, may be fully or partially halogenated, one or more carbons of the group may be substituted with halogen or CN, and one or more non-neighboring CH₂ groups can be replaced with an O, S or $Si(R^A)(R^B)$, in which $R^A$ and $R^B$, independently, are alkyl, alkenyl, alkynyl, haloalkyl, haloalkenyl or haloalkynyl groups, preferably those having from 1 to about 6 carbon atoms (preferred halogens being fluorines).

In the most general sense, the six member aromatic rings E and F in formula I can be replace with other aromatic systems, including 5-member aromatic rings and aromatic systems having one or two 5- or 6-member aromatic rings, wherein the aromatic ring system can be fused or non-fused ring system.

Compounds of this invention also include those of formula II and III:

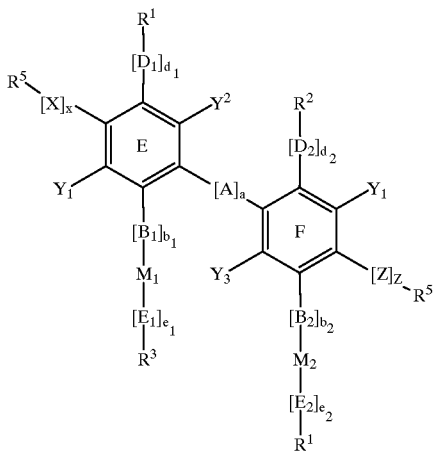

II where a, A, $b_1$, $b_2$, $B_1$, $B_2$, $d_1$, $d_2$, $D_1$, $D_2$, $e_1$, $e_2$, $E_1$, $E_2$, $Y_1$–$Y_4$, x, z, X, Z, $M_1$, $M_2$ and $R^1$–$R^6$ are as defined for formula I;

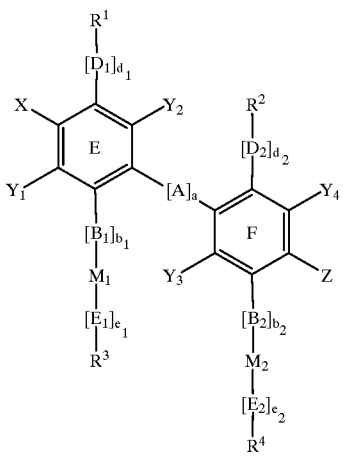

III where a, A, $b_1$, $b_2$, $B_1$, $B_2$, $d_3$, $d_2$, $D_1$, $D_2$, $e_1$, $e_2$, $E_1$, $E_2$, $Y_1$–$Y_4$, $M_1$, $M_2$ and $R^1$–$R^4$ are as defined for formula I and;

X and Z, independently of one another except as specifically stated herein, are selected from one of the following:

(1) the group consisting of H, an electron donor or an electron acceptor, with the proviso that when one of X or Z is an electron donor, the other of X or Z is an electron acceptor; or (2) the group consisting of H, halogen, CN, small alkyl, alkenyl or alkynyl groups having from 1 to about 3 carbon atoms, or small halogenated alkyl, alkenyl or alkynyl group having from 1 to about 3 carbon atoms with the proviso that any ring position of aromatic rings E or F that is a nitrogen does not carry a substituent.

$R^1$, $R^2$, $R^3$ and $R^4$ groups can be chiral nonracemic groups or achiral groups dependent upon the desired application of the compound. A particular subset of $R^1$–$R^4$ groups are those that are fully or partially fluorinated, designated by the variable $R_F$.

X and Z electron donor groups include any grouping known in the art to be an electron donor, for example any grouping causing activation of an aromatic ring relative to benzene in an electrophilic aromatic substitution reaction. Electron donors include groups in which the group atom connected to the aromatic ring is less electronegative than a halogen and where that atom possesses a lone pair able to interact with the aromatic ring in a resonance sense. Electron donors include: OR", NR"R'", NR"COR'", and OCOR", where R" and R'", independently of one another, are H or an alkyl having from 1 to about 6 carbon atoms (preferably having from 1 to 3 carbon atoms and most preferably methyl). More preferred electron donors are NR"R'", with $N(CH_3)_2$ being most preferred.

A particular subset of X and Z groups are those where one of X or Z is an electron donor and the other of X or Z is an electron acceptor.

X and Z electron acceptor groups include any grouping known in the art to be an electron acceptor, for example any grouping causing deactivation of an aromatic ring relative to benzene in an electrophilic aromatic substitution reaction. Electron acceptors include, among others, halogens, CN, $(CN)C=C(CN)_2$, COR", $CO_2R$", CONR"R'", $SO_2R$", $SO_2CF_3$ and $NO_2$ where R" and R'", independently of one another (and independent of R" and R'" groups of any electron donor), are H or alkyl or haloalkyl (preferably a fluoroalkyl) having from 1 to about 6 carbon atoms (preferably having 1 to 3 carbon atoms and most preferably methyl), except that in the group SOR", R" cannot be H. $NO_2$ is preferred over halogen and CN for obtaining large molecular β. The $(CN)C=C(CN)_2$, $SO_2CF_3$ and $NO_2$ are generally more preferred acceptors. $SO_2CF_3$ and $NO_2$ are more preferred acceptors for ferroelectric liquid crystal materials. The $NHCOCH_3$ grouping can be an acceptor if the lone pair on nitrogen is unable to interact with the aromatic ring in a resonance sense.

Compounds of this invention also include those of formula IV:

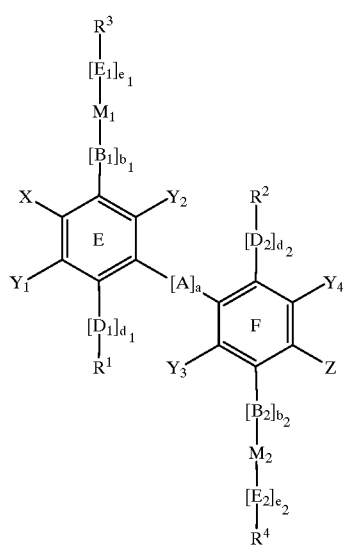

wherein a, $b_1$, $b_2$, $d_1$, $d_2$, $e_1$, $e_2$, A, $B_1$, $B_2$, $D_1$, $D_2$, $E_1$, $E_2$, Ring E and Ring F, X, Z, $Y_1$–$Y_4$, $M_1$, $M_2$, $R^1$ and $R^1$ are as defined for formula III ; and those of formula V:

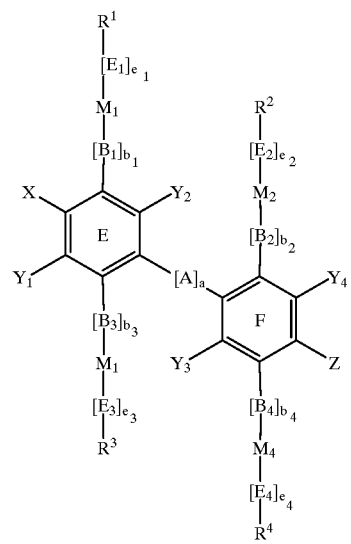

wherein a, $b_1$, $b_2$, $e_1$, $e_2$, A, $B_1$, $B_2$, $E_1$, $E_2$, Ring E and Ring F, X, Z, $Y_1$–$Y_4$, $M_1$, $M_2$, $R^1$ and $R^2$ are as defined for formula II and wherein $b_3$, $b_4$, $e_3$, and $e_4$ are 0 or 1, $B_3$ and $B_4$, independently of one another and $B_1$ and $B_2$, can be the same groups as defined for $B_1$ and $B_2$, $E_3$ and $E_4$, independently of one another and $E_1$ and $E_2$, can be the same groups as defined for $E_1$ and $E_2$, $M_3$ and $M_4$, independently of one another and $M_1$ and $M_2$, can be the same groups as defined for $M_1$ and $M_2$, $R_3$ and $R_4$, independently of one another and $R^1$ and $R^2$, can be the same groups as defined for $R^1$ and $R^2$.

In a more specific embodiment compounds of this include those of formula VI:

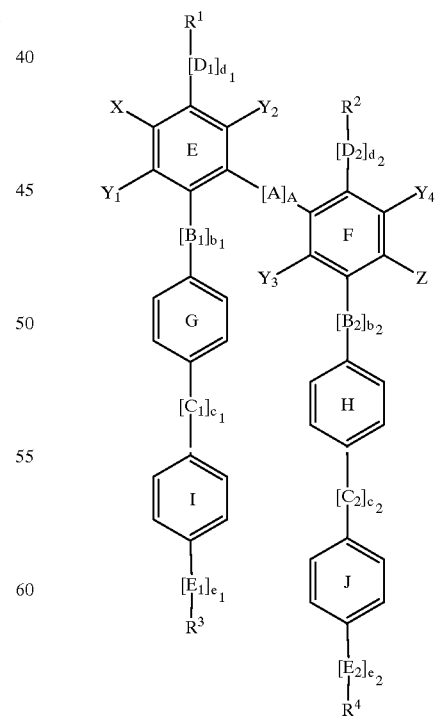

wherein $c_1$ and $c_2$, independently of one another, are 0 or 1 and $C_1$ and $C_2$, independently of one another, are selected from the group consisting of —C=C—, —C≡C—, —COO—, —OOC—, —CO—, —O—, —CH$_2$O—, —OCH$_2$—, —CH$_2$—CH$_2$—, —S—, —COS—, —SCO—, —CH=CHCOO—, —OOCCH=CH—, —CH=CHCOS— and —SOCH=CH—; and six-membered aromatic rings G, H, I and J, independently of one another, are 1,4-phenyl rings or 1,4-phenyl rings in which one or two of the carbon atoms of the ring are replaced with nitrogen atoms and in which carbons of the phenyl rings or nitrogen-containing phenyl rings can be substituted with halogens, CN, NO$_2$ or small alkyl, alkenyl, alkynyl, haloalkyl, haloalkenyl or haloalkynyl groups having from 1 to about 3 carbon atoms and all other variables are as defined in formula III.

$M_1$ and $M_2$ and ($M_3$ and $M_4$) moieties of the compounds of this invention include, but are not limited to those in which one or more of the $N_1$–$N_4$ are a 1,4-phenyl, a 1,4-phenyl in which one or two of the ring carbon atoms are replaced with nitrogens, a 1,4-phenyl in which one or more of the carbon atoms of the ring are substituted with a halogen, CN, small alkyl, alkenyl or alkynyl group having from 1 to about 3 carbon atoms, or small halogenated alkyl, alkenyl or alkynyl group having from 1 to about 3 carbon atoms, a 1,4-phenyl in which one or two of the ring carbon atoms are replaced with nitrogens and wherein one or more of the ring carbons are substituted with a halogen, CN group, small alkyl, alkenyl or alkynyl group having from 1 to about 3 carbon atoms, or small halogenated alkyl, alkenyl or alkynyl group having from 1 to about 3 carbon atoms, a 1,4-cyclohexyl or 1,4-cyclohexenyl group, a 1,4-cyclohexyl or 1,4-cyclohexenyl group in which one or two of the non-neighboring CH$_2$ groups are replaced with an oxygen, a 1,4-cyclohexyl or 1,4-cyclohexenyl group in which one or more of the ring carbons are substituted with a halogen or CN group, a bicyclic alkyl or bicyclic alkenyl group having from 5 to about 12 carbon atoms, a bicyclic alkyl or bicyclic alkenyl group having from 5 to about 12 carbon atoms in which one or two of the non-neighboring ring CH$_2$ groups are replaced with an oxygen atom; and a bicyclic alkyl or bicyclic alkenyl group having from 5 to about 12 carbon atoms, in which one or more of the ring carbons are substituted with a halogen or CN group.

$M_1$ and $M_2$ (and $M_3$ and $M_4$) groups of this invention include those in which one or more of $N_1$–$N_4$ are bicyclic [2,2,n] alkyl or alkenyl ring groups comprising a cyclohexyl or cyclohexenyl ring where n is an integer from 1 to about 6 wherein the bicyclic ring is optionally substituted with one or more halogens or CN groups.

Compounds of this invention also include those in which $M_1$, $M_2$, $M_3$, and $M_4$ are 1,4-cyclohexyl or 1,4-cyclohexenyl group, particularly those in which the cyclohexyl or cyclohexenyl group is in the trans configuration.

"A" groups are conjugating linker groups between the LC monomers. When a is 0 in formulas I–VI, then there is a single bond linking the rings of the dimerization link, preferred dimerization linkers when a is 0 are those containing at least one aromatic ring, such as biphenyl groups, phenylpyridine groups or phenylpyrimidine groups. Preferred "A" groups are —C≡C—, trans —C=C—, C≡C—C≡C— and —N=N—.

Preferred for NLO applications are compounds of this invention of formulas I–VI in which X is an electron donor or acceptor and Z is an electron acceptor or donor. More preferred electron acceptors are —NH$_2$ and N(CH$_3$)$_2$. Preferred electron donors are CN or NO$_2$.

Preferred achiral tails are those in which $E_1$–$E_4$ are O or S or those in which $e_1$–$e_4$ are 0.

In general, any chiral nonracemic LC tail group that is known to be useful in the preparation of FLC's or FLC dopant materials can be employed as a chiral tail group in the compounds of this invention. U.S. Pat. Nos. 5,051,506, 5,061,814, 5,167,855, 5,178,791, 5,178,793, 5,180,520, 5,271,864, 5,380,460, 5,422,037, 5,453,218, and 5,457,235, provide exemplary chiral (as well as achiral) tail groups for FLC, DHF and nematic LCs. Specifically, chiral tails of this invention include chiral 1-methylalkoxy groups, chiral 2,3-dihaloalkoxy groups, chiral 2-halo-3-methyl alkoxy and ester tails.

DETAILED DESCRIPTION OF THE INVENTION

Figure 1:
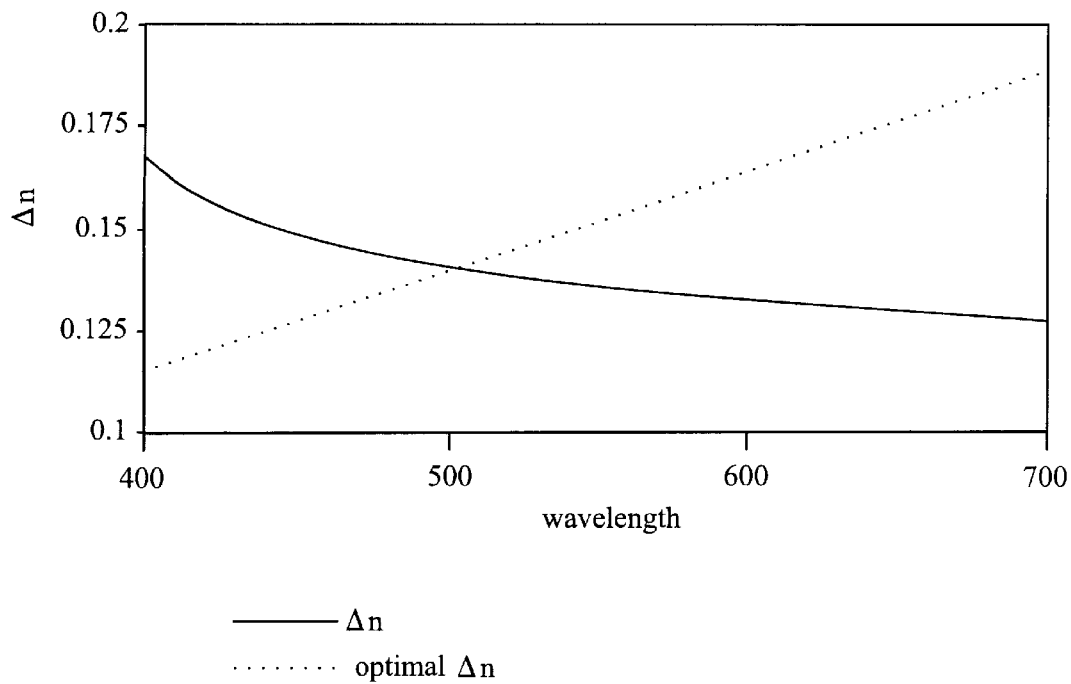
FIG. 1 shows the actual birefringence change with wavelength and the optimal birefringence for a cell of fixed thickness.
Figure 2:
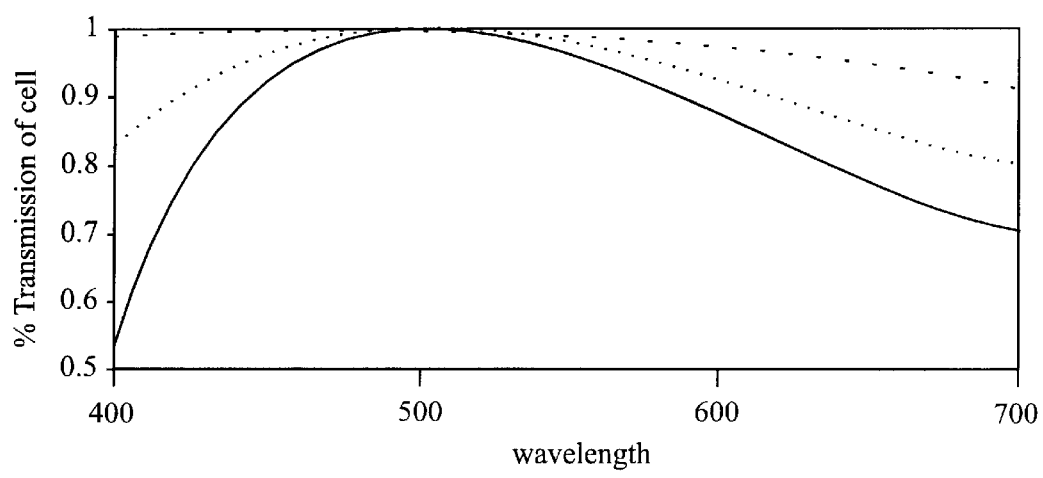
FIG. 2 shows light transmission of materials with positive, zero and negative birefringence dispersion.

In one aspect, the compounds of this invention are made up of low-birefringence monomers that are linked together to form dimers. The birefringence of the monomers is preferably minimized while making them compatible with the smectic C, nematic or other mesogenic phases. At the same time a highly birefringent group is incorporated perpendicular to the monomer's long axis. This moiety is the dimerization link. Several types of moieties typically used as cores in LC molecules are listed with their approximate birefringence in Scheme 1:

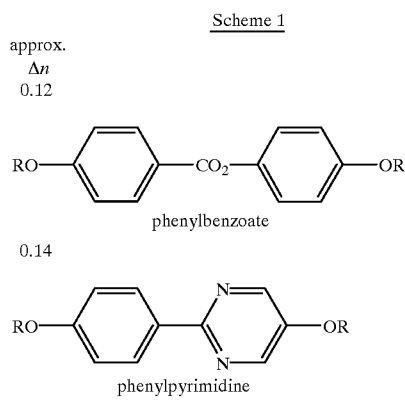

-continued 0.19
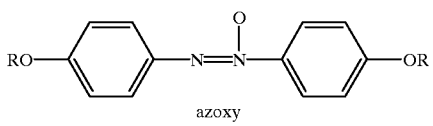
azoxy 0.21
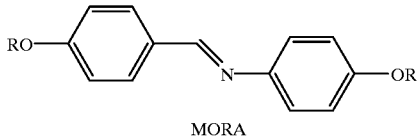
MORA 0.22
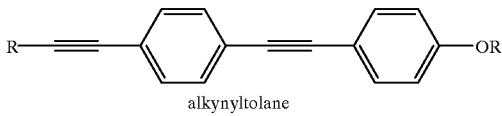
alkynyltolane 0.23
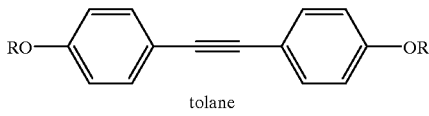
tolane 0.31
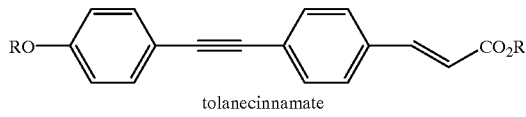
tolanecinnamate 0.33
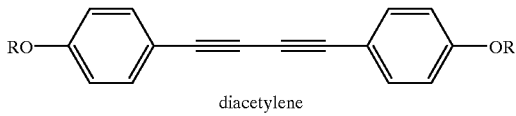
diacetylene Incorporation of moieties like those in Scheme 1, with birefringence higher than about 0.12 as the dimerization link perpendicular to the molecule's long axis ensures that n, will be greater than n, and that the dimer will have negative birefringence. U.S. patent applications Ser. No. 08/301,121 filed Sep. 9, 1994 and Ser. No. 08/458,411 filed Jun. 2, 1995 disclose compounds having high birefringence LC cores suitable for use as dimerization links in the compounds of this invention. These pending U.S. patent applications are incorporated in their entirety by reference herein.

Phenylbenzoate moieties have birefringence generally too low for use as dimerization links in the compounds of this invention. In contrast, a biphenyl moiety having birefringence of about 1.3 is useful as a dimerization link. Note that one type of exemplary dimerization link is composed of two Ph groups (where Ph is a 1,4-phenyl, or a 1,4-phenyl in which one or two ring carbons are replaced with nitrogen, for example, pyrimidinyl or pyridinyl) joined by a conjugating linking group A, for example: C≡C or C≡C—C≡C and other groups listed above, as in the moiety: —Ph—A—Ph—. In some cases the conjugation of the dimerization link is extended on one side of the Ph's as in the general formula: —A'—Ph—A—Ph— or —Ph—A—Ph—A', where A' can be the same conjugating groups as A. Useful dimerization links also include those in which conjugation is extended on both sides of the Ph's, as in the formula: —A'—Ph—A—Ph—A'—. The Ph rings of the dimerization link represent a portion of the core of the LC monomer. Substitution on the Ph rings of the dimerization link can be used to adjust the absorption spectra of the dimers to give a desired optimal birefringence dispersion.

The LC monomers that represent the lower birefringence and substantially linear moiety composing the long axis of the dimers of this invention can be generally represented by the formula:

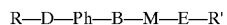

where Ph-B-M represents the core of the LC moiety, R and R' are chiral or achiral tail groups and D and E are optional linking groups between the core and the tails. B is an optional linking group between M and the Ph group and M can be a generally linear array of up to about four aromatic and/or alicyclic rings (N's) optionally separated by linking groups (F's):

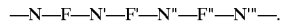

N ring groups of the monomers can be substituted with a variety of groups to adjust properties of the monomer (and dimers) for example to adjust LC properties or introduce NLO properties (as discussed below).

Monomers can be linked together at the Ph groups to form dimers in several configurations including a head-to-head (HH) and head-to-tail (HT) configurations, illustrated as:

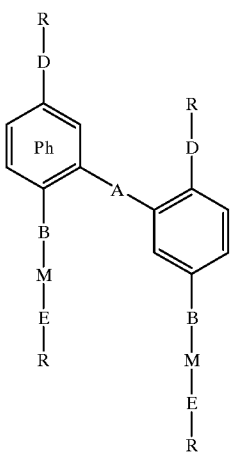

I

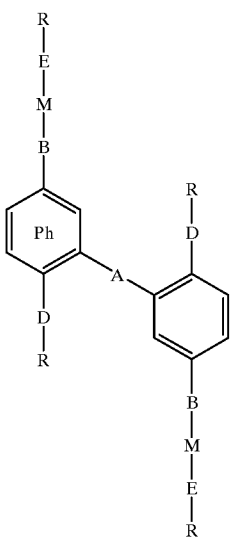

II

Compounds 2 and 3 are examples of head-to-tail configurations and compounds 4 and 5 are examples of head-to-head configurations.

More generally, the dimerization link can be mediated by any aromatic or alicyclic ring, in which alicyclic rings include, among others, cyclohexane and cyclohexene rings and bicyclic rings, such as -Cyc-A-Cyc-, where A is a conjugated linker as listed above in the definition of A, such as —C≡C— or —C≡C—C≡C— and Cyc=an alicyclic ring including a cyclohexane or cyclohexene ring. In this case too, conjugation can be extended on either side of the alicyclic rings as in the formulas; -A'-Cyc-A-Cyc-, -Cyc-A-Cyc-A'- or -A'-Cyc-A-Cyc-A'-. If the dimerization link is made through an alicyclic ring then the monomer need not contain any aromatic rings. Monomers in such cases can be given by the formula:

R-D-Cyc-B-M-E-R' where variables are as defined in the previous section. Dimers linked through dimerization links having alicyclic rings can be linked in head-to-tail HT and head-to-head HH configurations as described above.

Again more generally, the dimerization link between low birefringence monomers can be between any ring on one monomer and any ring on the other monomer. Note that although the term dimer has been used, the compounds of this invention include those "dimers" combining two structurally different monomers. Thus, the Ph or Cyc ring of the dimerization link need not be a terminal ring of the core linked to one of the tail groups, as illustrated by the monomer formulas:

R-D-M-B-Ph-B'-M'-E-R'

R-D-M-B-Cyc-B'-M'-E-R' where M' and B' can be selected from the same groups as M and B and the dimers are illustrated in formulas:

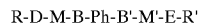
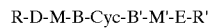

Compound 1 is an example of a dimer of this invention in which the dimerization link is between internal rings of the monomer core.

In general, the more rings a compound has, the more likely the compound will have mesogenic phases, although compounds with four or more rings tend to have higher viscosity and tend to be less soluble. Monomer cores can be extended without significantly increasing the birefringence along the long axis by including alicyclic rings, such as cyclohexyl and bicyclic rings, in the M core. These rings are linked in the monomer core in a generally linear fashion. Exemplary alicyclic M groups (with exemplary R shown) include:

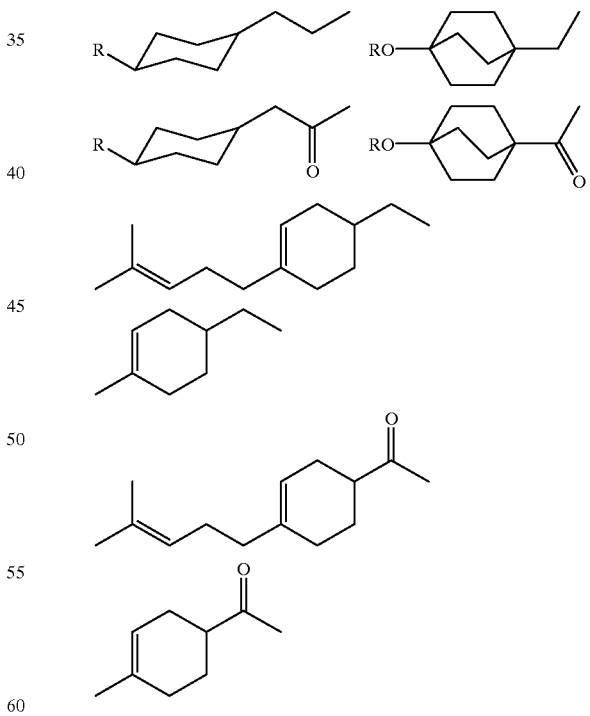

M core N rings can be one and two ring aromatics, such as 1,4-phenyl, 2,5-pyridinyl, 2,5-pyrimidinyl, napthalenyl, and biphenyl or alicyclic rings, such as trans-cyclohexyl, trans-cyclohexenyl, 1,4-bicyclo[2,2,2]octyl, and 1,4-bicyclo[2,2,2]octenyl. Bicyclic rings suitable for use as monomer N groups include those having from 5 to about 12 carbons in the bicyclic ring and include those bicyclic rings having 2 six-member rings ([2,2,2] rings), one six-member ring ([2,2,n] rings, where n is 1 about 6), and propellanes ([1,1,1] rings). Alicyclic and aromatic rings of the M groups can be substituted with a variety of functional groups including halogens (particularly fluorines), CN or $NO_2$.

R and R' groups are also generally linear and can contain a variety of functionalities. R and R' can be chiral non-racemic or achiral. Exemplary R and R' tail groups include the following:

---

A.
R—
alkyl-
$CH_3$—$Si(CH_3)_2$—$(CH_2)_n$
$CH_3$—$(CH_2)$—=—$(CH_2)_m$—
$CH_2$=$CH_2$—$(CH_2)_n$—
$CH_3$—$(CH_2)_n$—≡—$(CH_2)_m$—
$CH_3$—$(CH_2)_n$—O—$(CH_2)_m$—
$CH_3$—$(CH_2)_n$—S—$(CH_2)_m$—
$CH_3$—$(CH_2)_n$—$CF_2$—$(CH_2)_m$—
$CF_3$—$(CH_2)_n$—
$CF_3CF_2$—$(CH_2)_n$—
$CF_3$—$(CF_2)_n$—$(CH_2)_m$—
c-propyl-$(CH_2)_{n-3}$—
c-hexyl-$(CH_2)_{n-6}$
B.
R—≡—
alkyl—≡—
$CH_3$—$Si(CH_3)_2$—$(CH_2)_n$—≡—
$CH_3$—$(CH_2)_n$—=—$(CH2)_m$—≡—
$CH_2$=$CH_2$—$(CH_2)_m$—≡—
$CH_3$—$(CH_2)_n$—≡—$(CH_2)_m$—≡—
$CH_3$—$(CH_2)_n$—O—$(CH_2)_m$—≡—
$CH_3$—$(CH_2)_n$—S—$(CH_2)_m$—≡—
$CH_3$—$(CH_2)_n$—$CF_2$—$(CH_2)_m$—≡—
$CF_3$—$(CH_2)_n$—≡—
$CF_3CF_2$—$(CH_2)_n$—≡—
$CF_3$—$(CF_2)_n$—$(CH_2)_m$—
All other $R_1$ from column A
C.
R—=—
alkyl—=—
$CH_3$—$Si(CH_3)_2$—$(CH_2)_n$—=—
$CH_3$—$(CH_2)_n$—=—$(CH_2)_m$—=—
$CH_2$=$CH_2$—$(CH_2)_n$—=—
$CH_3$—$(CH_2)_n$—≡—$(CH_2)_m$—=—
$CH_3$—$(CH_2)_n$—O—$(CH_2)_m$—=—
$CH_3$—$(CH_2)_n$—S—$(CH_2)_m$—=—
$CH_3$—$(CH_2)_n$—$CF_2$—$(CH_2)_m$—=—
$CF_3$—$(CH_2)_n$—=—
$CF_3CF_2$—$(CH_2)_n$—=—
$CH_3(CH_2)_n$—O—CO—=—
$CH_3(CH_2)_n$—S—CO—=—
All other R from column A
D.
R—O—
alkoxy-
$CH_3$—$Si(CH_3)_2$—$(CH_2)_n$—O—
$CH_3$—$(CH_2)_n$—=—$(CH_2)_m$—O—
$CH_2$=$CH_2$—$(CH_2)_n$—O—
$CH_3$—$(CH_2)_n$—≡—$(CH_2)_m$—O—
$CH_3$—$(CH_2)_n$—O—$(CH_2)_m$—O—
$CH_3$—$(CH_2)_n$—S—$(CH_2)_m$—O—
$CH_3$—$(CH_2)_n$—$CF_2$—$(CH_2)_m$—O—
$CF_3$—$(CH_2)_n$—O—
$CF_3CF_2$—$(CH_2)_n$—O—
All other R from column A
E.
$R_1$—S—
$CH_3$—$Si(CH_3)_2$—$(CH_2)_n$—S—
$CH_3$—$(CH_2)_n$—=—$(CH_2)_m$—S—
$CH_2$=$CH_2$—$(CH_2)_m$—S—
$CH_3$—$(CH_2)_n$—≡—$(CH_2)_m$—S—
$CH_3$—$(CH_2)_n$—O—$(CH_2)_m$—S—
$CH_3$—$(CH_2)_n$—S—$(CH_2)_m$—S—
$CH_3$—$(CH_2)_n$—$CF_2$—$(CH_2)_m$—S—
$CF_3$—$(CH_2)_n$—S—
$CF_3CF_2$—$(CH_2)_n$—S—
All other $R_1$ from column A

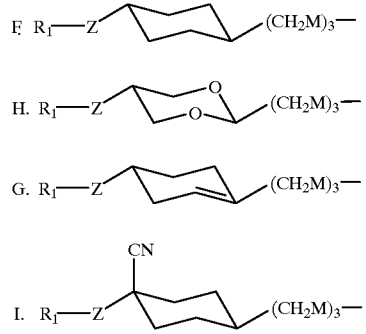

F. $R_1$—Z—(cyclohexyl)—$(CH_2M)_3$—

H. $R_1$—Z—(tetrahydropyran)—$(CH_2M)_3$—

G. $R_1$—Z—(cyclohexenyl)—$(CH_2M)_3$—

I. $R_1$—Z—(CN-cyclohexyl)—$(CH_2M)_3$—

--- where n and m are integers; n+m less than or equal to about 20; Z is a single bond, oxygen or sulfur; M is —$CH_2$—, a single bond or oxygen and a is 0 or 1.

$CH_3$—$Si(CH_3)_2$—$(CH_2)n$—
$CH_3$—$(CH_2)_n$—=—$(CH_2)_m$—
$CH_2$=$CH_2$—$(CH_2)_n$—
$CH_3$—$(CH_2)_n$—≡—$(CH_2)_m$—
$CH_3$—$(CH_2)_n$—O—$(CH_2)_m$—
$CH_3$—$(CH_2)_n$—S—$(CH_2)_m$—
$CH_3$—$(CH_2)_n$—$CF_2$—$(CH_2)$—
$CF_3$—$(CH_2)_n$—
$CF_3CF_2$—$(CH_2)$—
$CF_3$—$(CF_2)_n$—$(CH_2)_m$—
$CH_3$—$(CF_2)_n$—$(CH_2)_m$— n and m are integers; n+m less than or equal to about 20.

---

| Exemplary $R_F$—X— | |
|---|---|
| $R_F$— | $R_F$—O— |
| $CH_3$—$(CH_2)_n$—$CF_2$—$(CH_2)_m$— | $CH_3$—$(CH_2)_n$—$CF_2$—$(CH_2)_m$—O— |
| where: n + m ≤ about 18 or | |
| n + 1 = m and n + m ≤ about 18 | |
| $CH_3$—$(CH_2)_n$—$(CF_2)_m$— | $CH_3$—$(CH_2)_n$—$(CF_2)_m$—O— |
| where: n + m ≤ about 19 | |
| n + 1 = m and n + m ≤ about 19 | |
| $CF_3$—$(CH_2)_n$— | $CF_3$—$(CH_2)_n$—O— |
| where: n ≤ about 19 | |
| $CF_3CF_2$—$(CH_2)_n$— | $CF_3CF_2$—$(CH_2)_n$—O— |
| where: n ≤ about 18 | |
| $CF_3$—$(CF_2)_n$—$(CH_2)_m$— | $CF_3$—$(CF_2)_n$—$(CH_2)_m$—O— |
| where: n + m ≤ about 19 or | |
| n + 1 = m and n + m ≤ about 19 | |
| $CH_2$=CH—$(CF_2)_n$— | $CH_2$=CH—$(CF_2)_n$—O— |
| where: n ≤ about 18 | |
| $CF_2$=CF—$(CF_2)_n$— | $CF_2$=CF—$(CF_2)_n$—O— |
| where: n ≤ about 18 | |
| $CF_3$—$(CF_2)_n$—CH=CH— $(CH_2)_m$— | $CF_3$—$(CF_2)_n$—CH=CH— $(CH_2)_m$—O— |
| where: n + m ≤ 17 or | |
| n + 1 = m and n + m ≤ 17 | |
| $CF_3$—$(CF_2)_n$—$(CH_2)_m$—CH=CH— | |
| where: n + m ≤ 17 or | |
| n + 2 = m and n + m ≤ 17 | |
| c-propyl-$(CF_2)_n$— | c-propyl-$(CF_2)_n$—O— |
| where: n ≤ about 17 | |
| Note: n and m are both integers | |
| $CF_3$—$(CF_2)_n$— | $CF_3$—$(CF_2)_n$—O— |
| where: n ≤ about 19 | |
| $CF_2H$—$(CF_2)_n$— | $CF_2H$—$(CF_2)_n$—O— |

-continued

| Exemplary $R_F$—X— | |
|---|---|
| $R_F$— | $R_F$—O— |
| where: $n \leq$ about 19 | |
| $CF_2H$—$(CF_2)_n$—$(CH_2)_m$— where: $n + m \leq$ about 19 or $n + 1 = m$ and $n + m \leq$ about 19 Note: n and m are both integers | $CF_2H$—$(CF_2)_n$—$(CH_2)_m$—O— |

$CH_3$—$(CH_2)_n$—
Branched alkyl-
$CH_3$—$Si(CH_3)_2$—$(CH_2)_n$—
$CH_3$—$(CH_2)_n$—$CH$=$CH$—$(CH_2)_m$—
$CH_2$=$CH_2$—$(CH_2)_n$—

$CH_3$—$(CH_2)_n$—$C\equiv C$—$(CH_2)_m$—
$CH_3$—$(CH_2)_n$—O—$(CH_2)_m$—
$CH_3$—$(CH_2)_n$—S—$(CH_2)_m$—
$CH_3$—$(CH_2)_n$—$CF_2$—$(CH_2)_m$—
$CF_3$—$(CH_2)_n$—
$CF_3CF_2$—$(CH_2)_n$—
$CF_3$—$(CF_2)_n$—$(CH_2)_m$—
$CH_3$—$(CF_2)_n(CH_2)_m$—
$CF_3$—$(CF_2)_n$—
c-cyclopropyl-$(CH_2)_n$—
c-hexyl-$(CH_2)_n$— where: n and m are integers; $n+m \leq$ about 20.

Specific types of compounds of this invention include those listed in Schemes 2–7:

Scheme 2

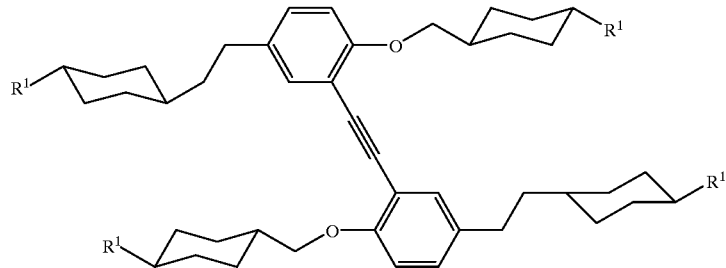

1

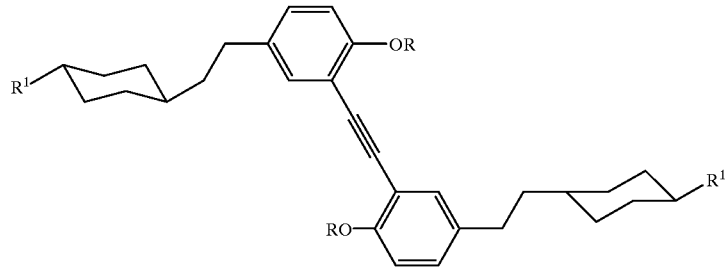

2

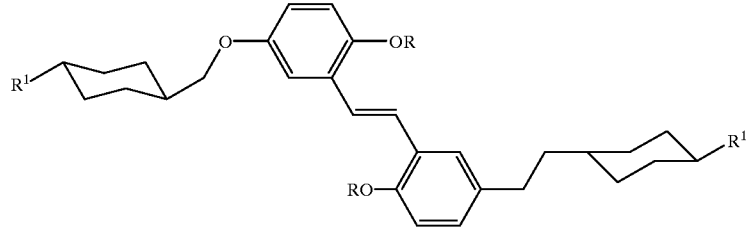

3

-continued
4
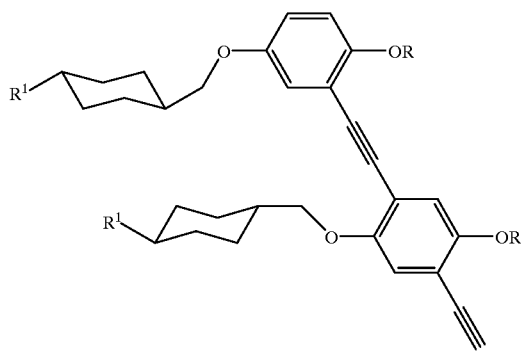
5
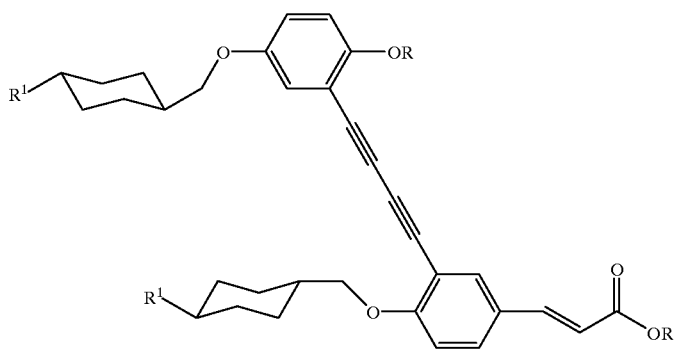
R¹ can be ——C₅H₁₁
——C₅F₁₁, among others
Scheme 3
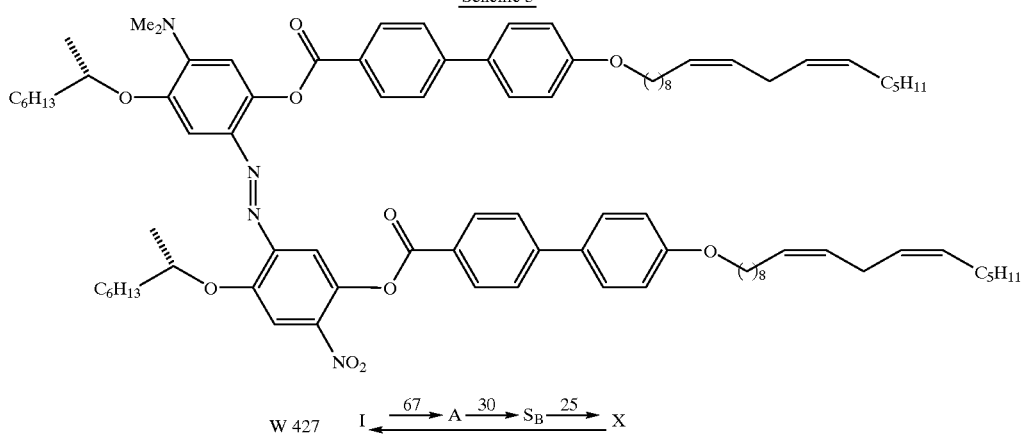
W 427   I $\xrightleftharpoons{67}$ A $\xrightarrow{30}$ S$_B$ $\xrightarrow{25}$ X Scheme 4
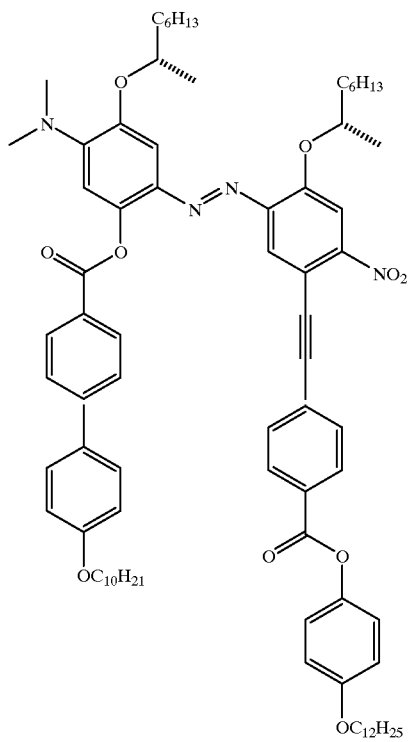
70
Core
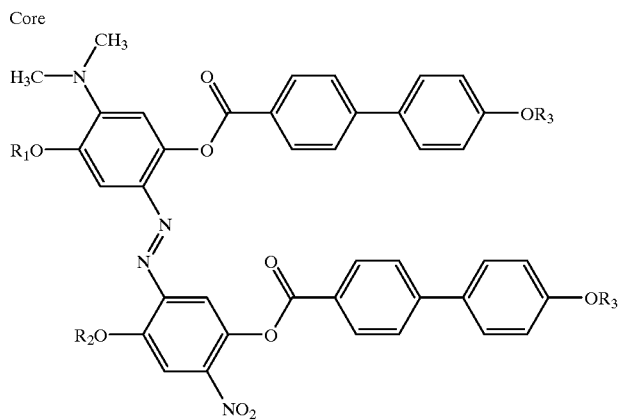
Tails
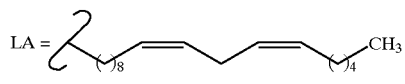
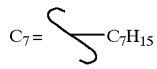
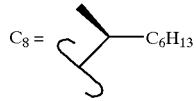
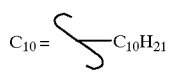

Scheme 5
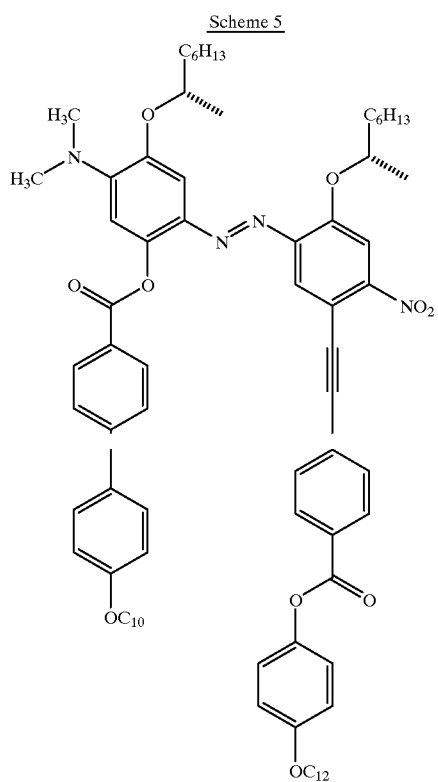
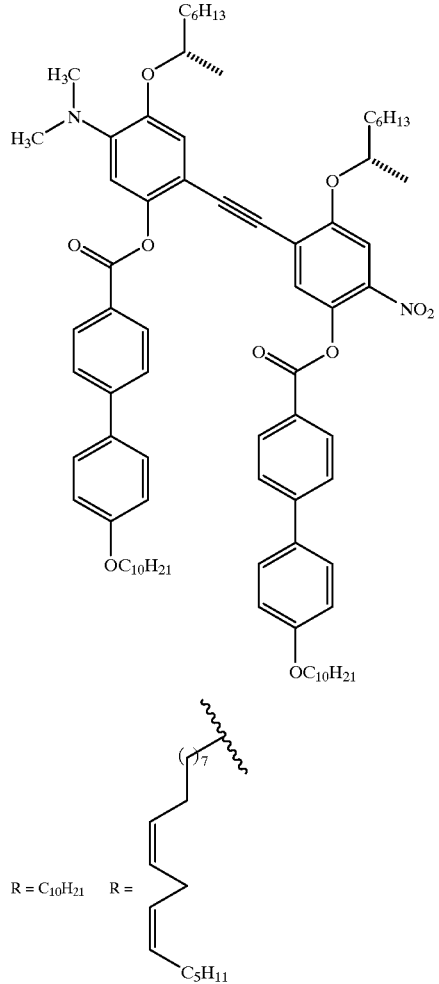
R = $C_{10}H_{21}$    R =
Scheme 6
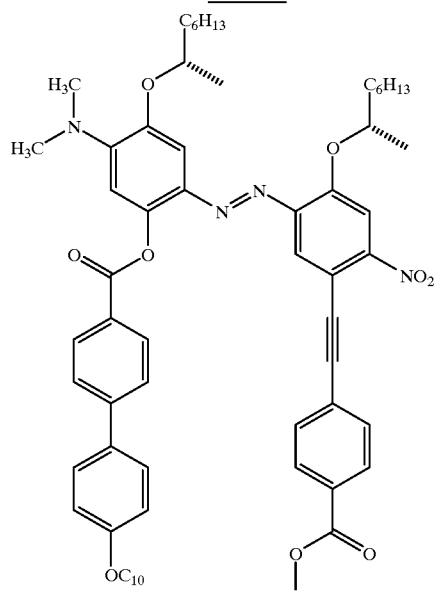

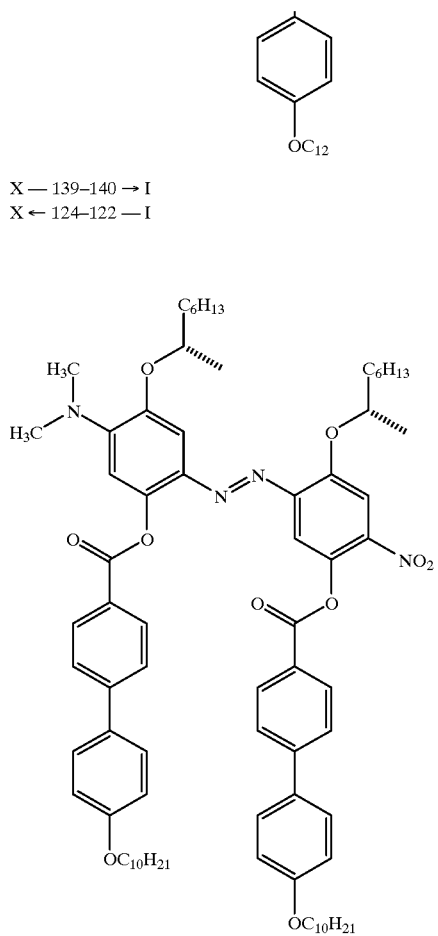
X — 139–140 → I
X ← 124–122 — I
X ← <25 — A* ← 99–97 — I
X — 111.6 → I
A* — 103–107 → I
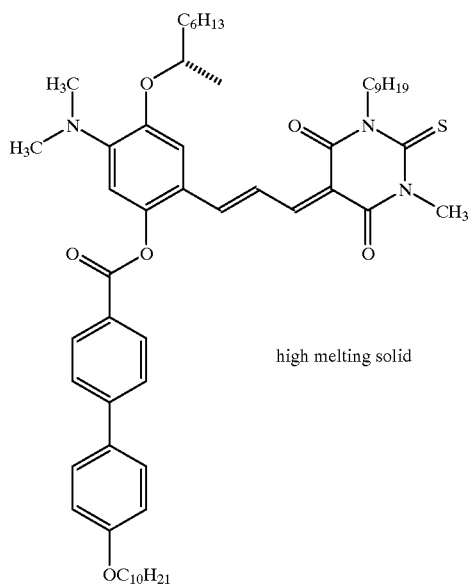
high melting solid
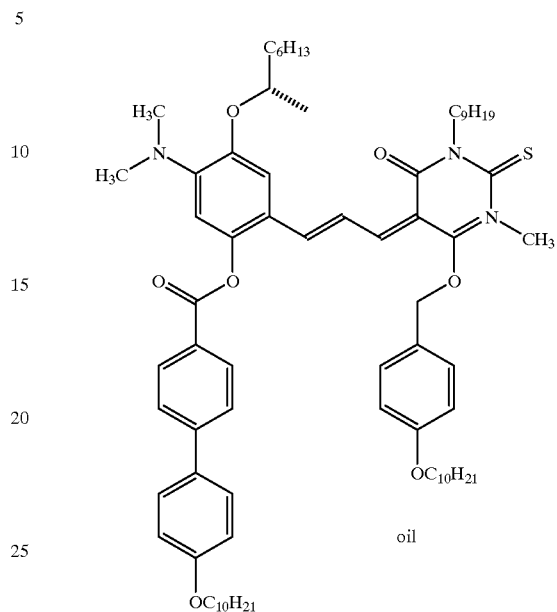
oil
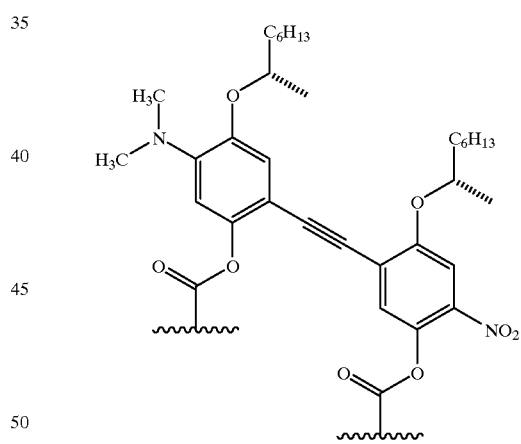
$S_x$ ← 72.6 — A* ← 78.5 — N* ← 91.8 — I
X — 73 → A* — 78.5 → N* — 92 → I
40% in W 346:
SI* ← 99 — A* ← 118 — I
$P_{ext}$ in the I* phase ≈ 35 nC/cm²

-continued

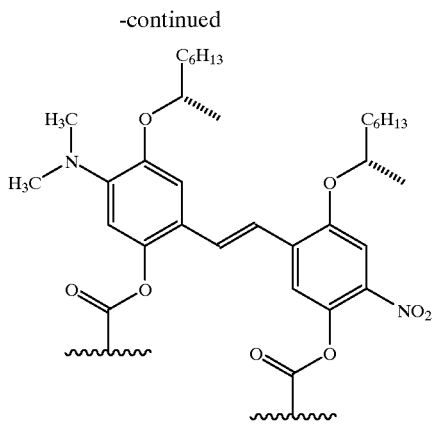

12% in W 346:
X ← 53 — C* ← 88 — A* ← 123 — I
$P_{ext} \cong 50$ nC/cm² (10% pc)

Scheme 7

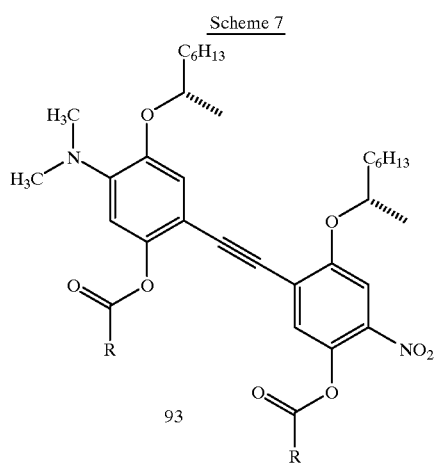

93

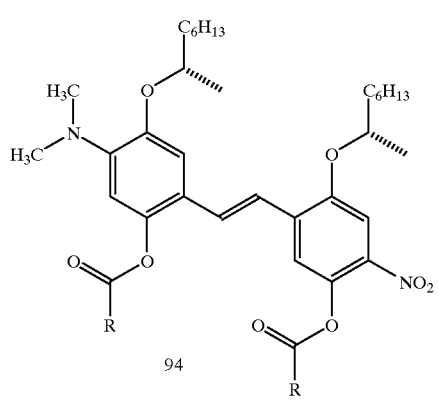

94

R = ——Ph——Ph——OC₁₀H₂₁

-continued

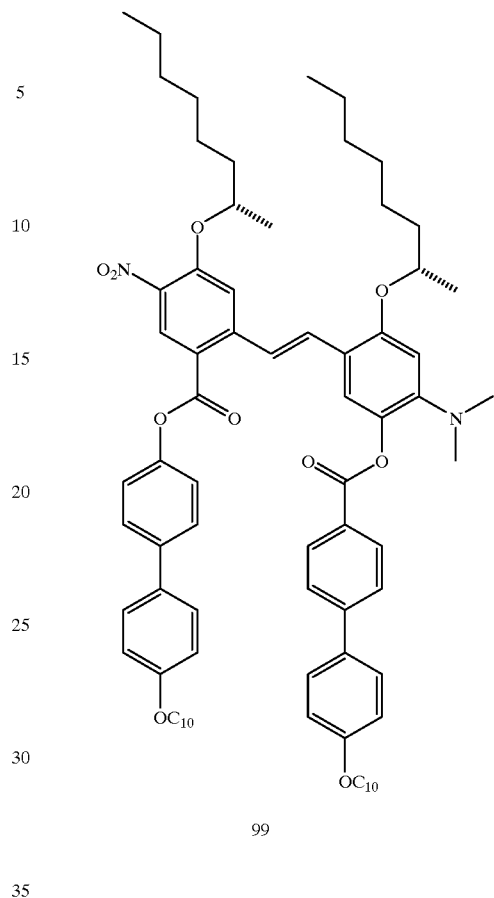

99

Methods of synthesis for several types of compounds of this invention are exemplified in the Examples section, including several reaction schemes, below. One of ordinary skill in the art can use the exemplified methods, or routine adaptations or modifications of these methods and in combination with methods well known in the art can synthesize any of the dimer compounds of this invention.

Compounds of this invention are useful as components in LC compositions having reduced or negative birefringence dispersion (compared to typical LC compositions composed of monomer LC compounds). Mesogenic composition of this invention include those that incorporate one or more of the dimers of this invention. Typically an LC composition can contain from about 1% to about 50% of a dimer (or a mixture of dimers of this invention). The amount of negative birefringent dimer or dimers included in a given composition is adjusted to maximize benefit to the birefringence dispersion without significant detriment to desired mesogenic (LC) properties.

The LC compositions of this invention with anomalous dispersion are useful in a variety of electrooptical devices to reduce chromaticity. Device applications include, among others, FLC-, nematic-, and DHF-based optical cells and devices, small area displays, nematic displays, Fabry-Perot tunable filters, optical bandwidth filters, and polarization filters.

In a second aspect this invention relates to LC materials having NLO properties. While excellent improvement of $\chi^{(2)}$ in FLCs has been achieved by design, useful materials for integrated optics clearly require further increases in susceptibility. Thus, a value for the electro-optic coefficient of 50 pm/V for modulation of 1.3 μm light at frequencies on the order of 50 GHz seems a reasonable target, and indeed even larger EO coefficients would be highly desirable. Prototypical "large β" functional arrays, typified by the Disperse Red 1 (DR1) chromophore (β=49×10$^{-30}$ esu), involve at least two rings linked by a conjugating spacer unit. While such units are easily incorporated into LC structures, in all known cases such functional arrays orient along the liquid crystal director, while in C*FLCs the polar axis is normal to the director. Maintaining the LC aspect ratio of an LC compound with a two ring 1 unit, such as that present in DR1, oriented normal to the director would require such a long structure that an intractable material would be expected. Thus the aspect ratio argument seems to preclude the orientation of large β units along the polar axis in FLCs, limiting the obtainable $\chi^{(2)}$ values.

Initial results of a study directed towards developing a solution to this problem are illustrated below:

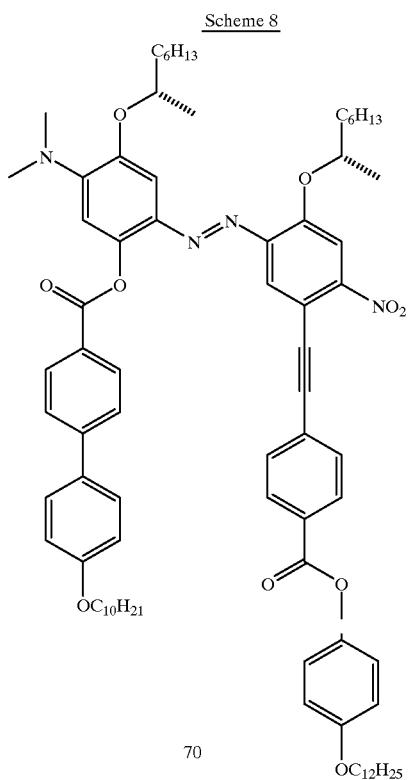

Scheme 8

70

Phase sequence of the mixture (30% by weight)
of 70 in racemic 3a (temperatures in degrees C.):
X ← 35 — C* ← 90 — A* ← 120 — I
X — 70 → C*

$P_{obs}$ = +26.6 nC/cm$^2$ @ 40° C., θ = 31.5°
$P_{ext}$ = +88.5 nC/cm$^2$ ≈ 0.5 D/molecule Negative Dichroism (max absorption ⊥ n̂)

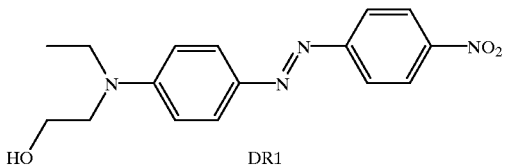

DR1

A side-by-side dimer structure such as 70 would show the following desired properties: 1) Dimers such as 70 show considerable solubility in C phase hosts; 2) The tolan and biphenyl units orient along the director, forcing the DR1 chromophore to make a large angle to the director; and 3) Steric coupling of the chiral tails with the ortho substituents provides polar orientation of the DR1 unit in the FLC phase as required for $\chi^{(2)}$.

The azo dye 70 mixes up to at least 30% by weight in the C phase host racemic 73a, with the 30% mixture showing a 20° enantiotropic C* phase range and a very broad monotropic C* phase. The sign of the observed ferroelectric polarization for (S,S)-70 (opposite that observed for (S)-73a is consistent with the expected supermolecular structure since the dipole contribution from the azo unit should be opposed to dipole contributions from the ether oxygens, and of larger magnitude. Finally, preliminary visible light spectroscopy measurements show that parallel-aligned samples exhibit the expected negative dichroism (dichroic ratio <1) suggesting that the axo unit is making an angle >54° (the magic angle) with the LC director. The value of $P_{ext}$≈0.5 D/molecule (assuming a density of 1.1 gms/cm$^3$ for the mixture) suggests a polar excess of ≅10% assuming a net dipole normal to the director of 5 D.

That the polar excess obtained with compound 70 is smaller than that obtained for the o-nitroalkoxyphenyl systems 73 and 76 is likely not due to the dimer structure itself, but rather to the relatively weak polar orientation of aryl rings observed when a dimethylamino grouping is placed ortho to the 1-methylheptyloxy chiral tail. Thus, the biphenylbenzoate 78 exhibits a very small extrapolated polarization (5nC/cm$^2$, sign not given), while as noted above, in racemic 73a as host the "flipped" o-nitroalkoxyaniline induces a very large negative polarization in mixtures.

The "side-by-side" LC dimer 70 exhibited relatively low ferroelectric polarizations (P≅60 nC/cm$^2$), and small polar-excesses (pe≅15%). We considered that the dimethylamino unit could exhibit poor steric coupling with the chiral tail.

Scheme 9

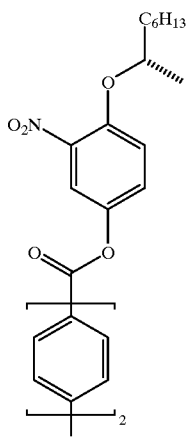

73a; R = C₁₀H₂₁
73b; R = C₁₀H₂₀Si(Et)₃

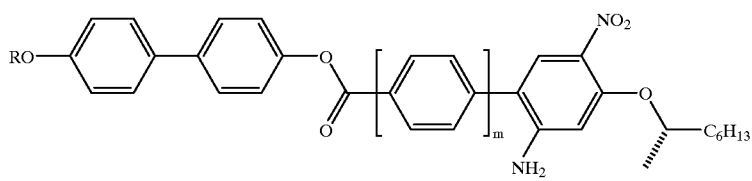

76a; R = C₁₀H₂₁, m = 0
76b; R = C₉H₁₉, m = 1

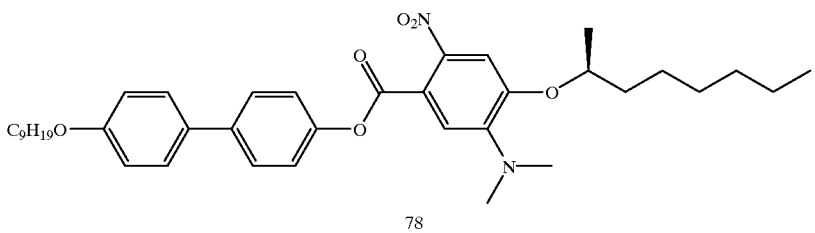

78

We examined the steric control that the chiral tails exert on the DR1 chromophore in order to orient it along the polar axis. Substitution of the methyl group on the chiral tail for a hydrogen should eliminate any steric bias between the two conformations. Thus, the polarization drops to zero (it must since the system becomes achiral). For the azo system there are two chiral tails. These tails sterically couple with the dimethylamino and the trans-azo moieties. The "mono chiral tailed" analogs 85 and 86 yielded 60% and 20% lower values for P respectively, than compound 84 with two chiral tails. Thus, each tail-core system contributes to the overall orientation of the DR1 unit (the dimethylamino moiety appears to be twice as effective as the trans-azo linkage), however, in all cases the polar order is quite low, with pe≅13% for compounds 83 and 84.

Scheme 10
Core

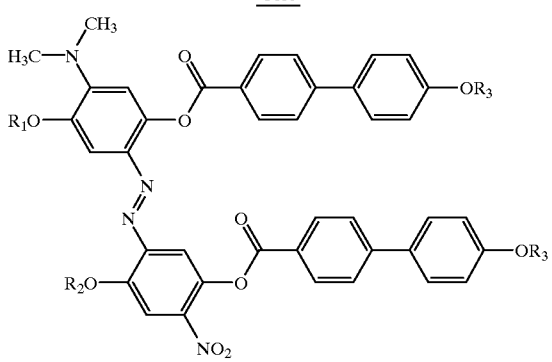

-continued

Tails

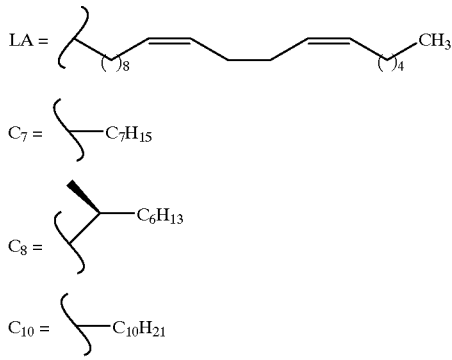

Scheme 11

The "anisole effect" may not be as strong when an amino group is ortho to the alkoxy tail.

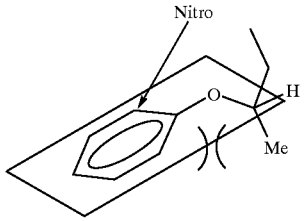

(A) Good Steric Coupling

| Compound | $R_1$ | $R_2$ | $R_3$ | Phase Diagram | P @ ° C. (nC/cm$^2$) | $P_{ext}/\sin(\theta)$ | pe |
|---|---|---|---|---|---|---|---|
| 83 | $C_8$ | $C_8$ | $C_{10}$ | X $\underset{44}{\overset{112}{\rightleftarrows}}$ A* $\underset{}{\overset{99}{\rightleftarrows}}$ I | +35.6 @ 50$^a$ | 129 | 13% |
| 84 | $C_8$ | $C_8$ | LA | X $\underset{<25}{\overset{72}{\rightleftarrows}}$ B* $\underset{34}{\overset{}{\rightleftarrows}}$ A* $\underset{67}{\overset{73}{\rightleftarrows}}$ I | +33.1 @ 55$^a$ | 133 | 13% |
| 85 | $C_7$ | $C_8$ | LA | X$_A$ $\underset{91}{\overset{100}{\rightleftarrows}}$ X$_B$ $\underset{102}{\overset{123}{\rightleftarrows}}$ I | +8.7 @ 55$^b$ | 55 | 4% |
| 86 | $C_8$ | $C_7$ | LA | X $\underset{71}{\overset{92}{\rightleftarrows}}$ ? $\underset{84}{\overset{}{\rightleftarrows}}$ C* $\underset{99}{\overset{101}{\rightleftarrows}}$ I | +20.0 @ 45$^b$ +32.3 @ 85$^c$ | 107 204 | 10% |

$^a$50% by weight in racemic W314.
$^b$40% by weight in racemic W314.
$^c$Neat

Figure 3:
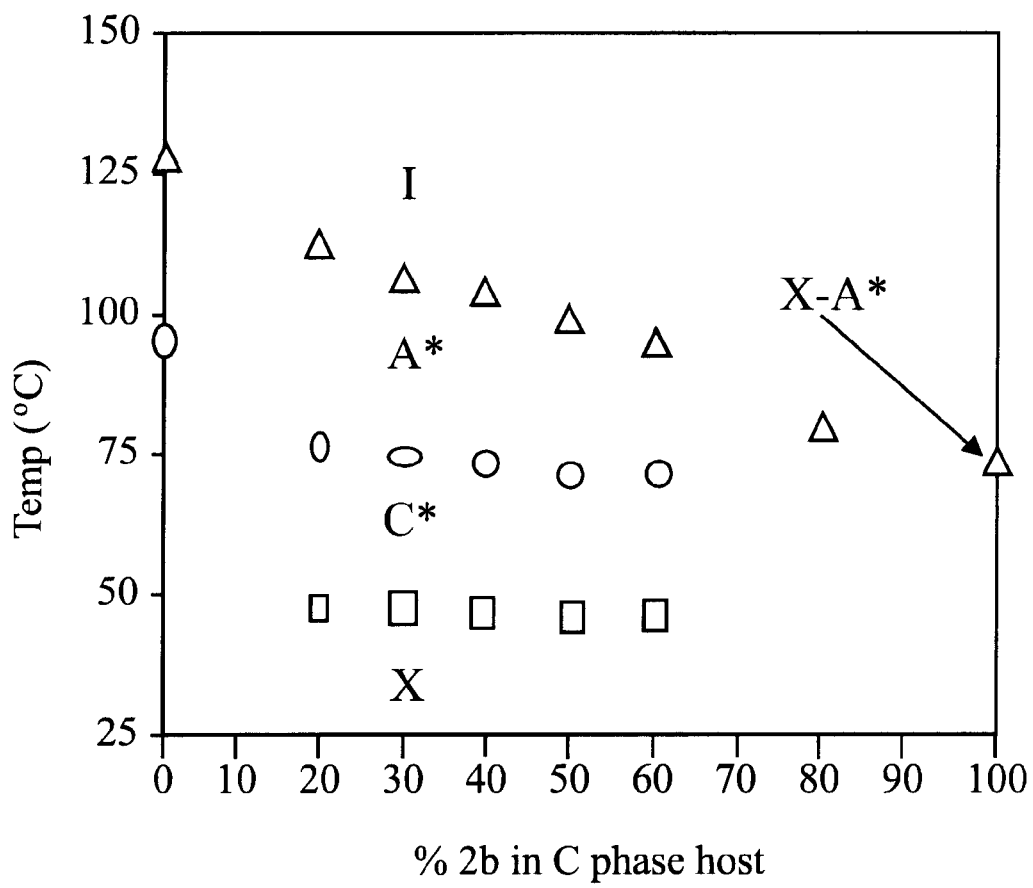
FIG. 3 shows a phase diagram for mixtures of 84 in racemic W314.
Figure 4:
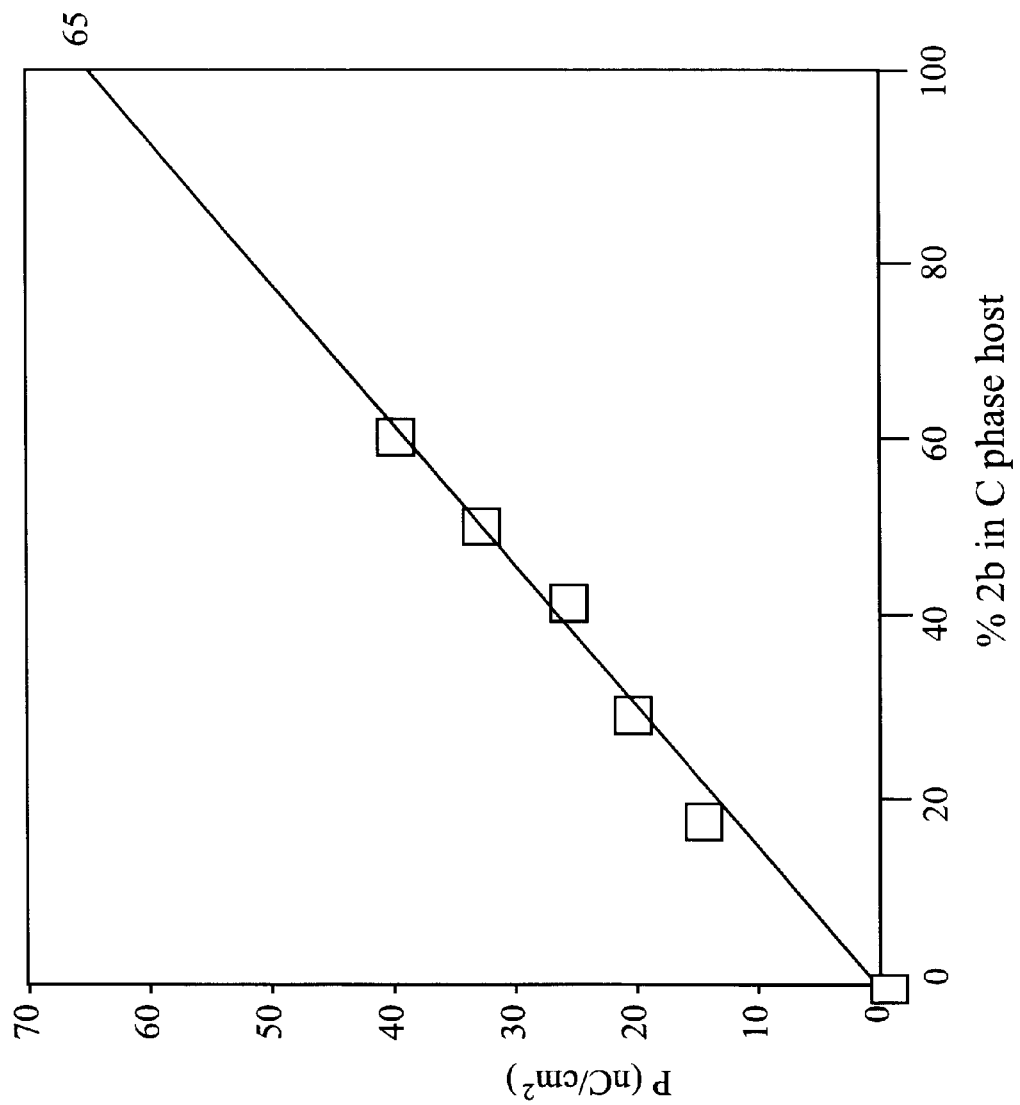
FIG. 4 shows the measured saturation ferroelectric polarization for mixtures 84 in racemic W314.

Compound 84 is miscible in all proportions with host racemic W314 with mixtures exhibiting a C phase up to 60% by weight as shown by the following phase diagram in FIG. 3. The ferroelectric polarization of these C* mixtures is well-behaved, as indicated in the following plot in FIG. 4. These figures show an extrapolated polarization of +65 nC/cm$^2$ (about 0.4 D/molecule) for 84.

One possible explanation for the poor stereocontrol exhibited by the o-dimethylamino system is suggested by MOPAC semi-empirical quantum mechanics calculations using the AM1 Hamiltonian. The so-called "anisole effect," whereby the aromatic ring and the alkoxy bond lie in the same plane, is an important contributor to the overall steric coupling of our systems. The following diagram illustrates this problem with two possible conformations for the alkoxy bond relative to the aryl ring. Calculations suggests that conformation B is preferred over A when the dimethylamino group is situated ortho to the alkoxy tail. This would lead to poor steric coupling:

-continued

Rotations around these bonds are not sterically coupled to the ortho substituent

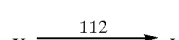

(B) Poor Steric Coupling
Proposed Orientation of the Alkyloxy Bond Relative to the Ary Ring.

Since dimethylaminonitrostilbene (DANS) is known to possess a larger β value than DR!, the carbon analogs 93 and 94 of the azo dyes were synthesized. Compound 93 shows excellent mesogenicity with enantiotropic N* and A* phases. The DANS dimer 94 is not mesogenic. Characterization of 94 in a mixture with racemic W314:

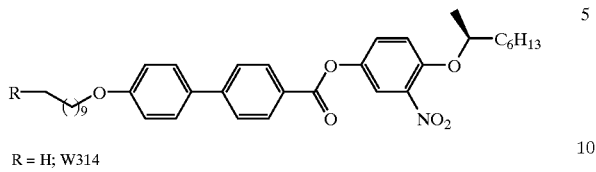

R = H; W314 suggests that the supermolecular structure obtained with the DANS dimer is similar to that obtained in the DR1 case, with a 10% polar excess for orientation of the chromophore indicated by the observed ferroelectric polarization.

Scheme 12

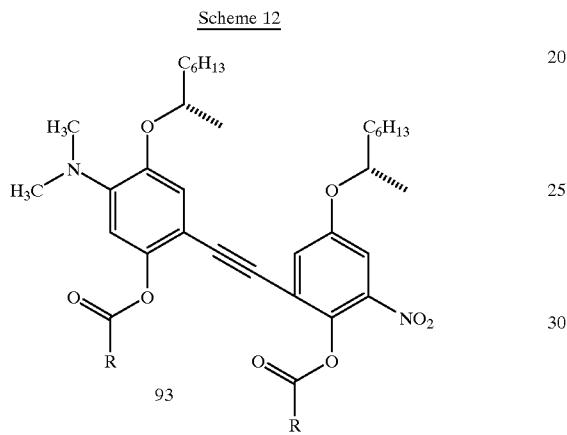

93

Phase sequence of neat sample:

Sx ← 72.6 — A* ← 78.5 — N* ← 91.8 — I
X — 73 → A* — 78.5 → N* — 92 → I

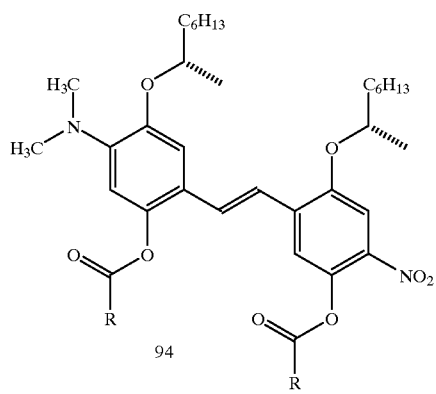

94

12% in racemic W314:

X ← 53 — C* ← 88 — A* ← 123 — I $P_{ext} \cong 50$ nC/cm$^2$ (10% pe)

R = ——Ph——Ph——OC$_{10}$H$_{21}$

In dimers of this invention for NLO applications, substituted at X and Z positions (see Formulas I–IV), compounds in which the electron donor is substituted ortho to the chiral tail are preferred having generally higher ferroelectric polarization compared to the analogous compounds having the electron donor in the meta position with respect to the chiral tail. This improvement is illustrated by the following comparison:

Scheme 13

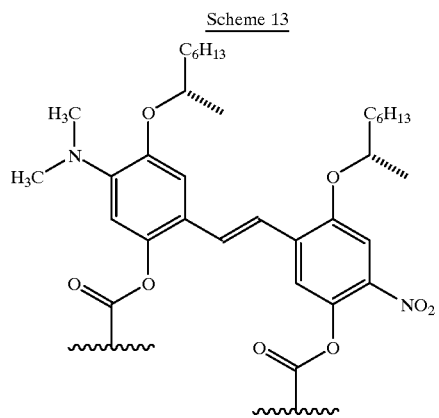

12% in W 346:

X ← 53 — C* ← 88 — A* ← 123 — I $P_{ext} \cong 50$ nC/cm$^2$ (10% pc)

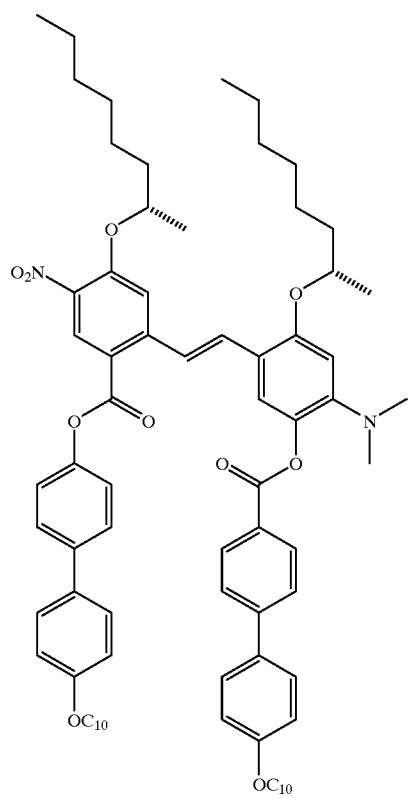

X — 100 → A* — 150 → I $P_{ext} \cong -500$ nC/cm$^2$ (25% pe)

from a 20% mix in W346

EXAMPLES
Exemplary Syntheses of Negative Birefringence Dimers

Example 1.1

Compound 2 can be made according to the method outlined in the following Scheme:

The Synthesis of Tolane and Styrene Compounds

Scheme 14

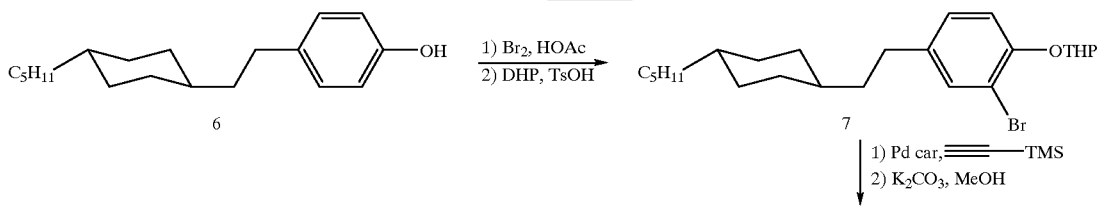

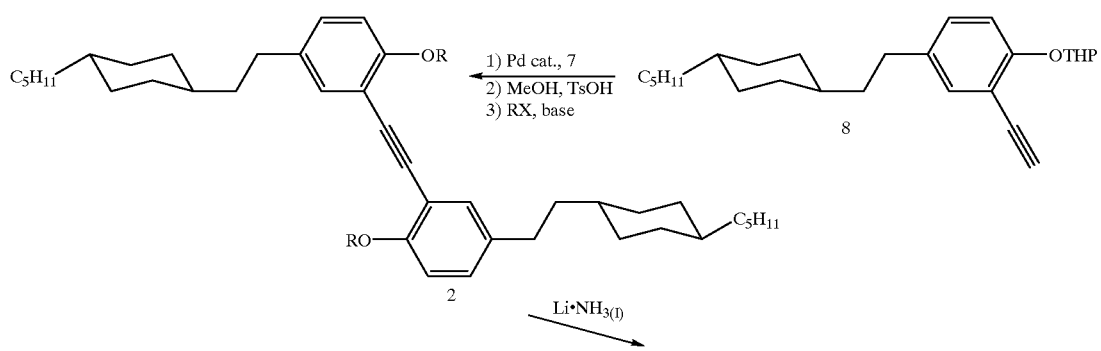

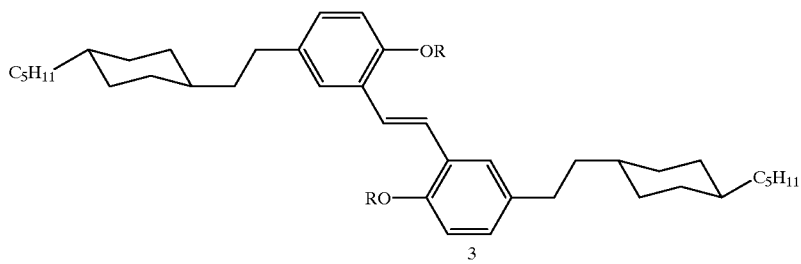

Cyclohexylethylenephenol 6 can be brominated using elemental bromine in acetic acid, giving a bromophenol. The phenol moiety can then be protected as the tetrahydropyran using dihydropyran with an acid catalyst, resulting in the THP ether 7. This material can then be transformed into an alkyne using trimethylsilylacetylene and a palladium catalyst (D. Dawson et al. (1987) "Polymers for High Technology Electronics and Photonics":445.) The trimethylsilyl group can then be removed using potassium carbonate in methanol, resulting in the acetylene 8. This, in turn, can be treated with another equivalent of aryl bromide 7 to give a tolane. The THP groups can be removed from the tolane using methanol with catalytic acid to give the dephenol. A second tail can then be attached, either by adding an acid chloride in the presence of triethylamine to give an ester, or by using an alkyl halide in the presence of cesium carbonate to give an ether. In either event, the result will be a compound of type 2.

Tolane 2 can then be partially reduced to give the styrene 3. Since the trans configuration of the double bond is desired, the preferential reduction path is using lithium in liquid ammonia. These reaction conditions are not used if compound 2 is an ester. However, in that case the lithium reaction can be done before the THP groups are removed.

Example 1.2

The synthesis of the alkynyltolane 4 is detailed in the following Scheme:

The Synthesis of Alkynyltolanes

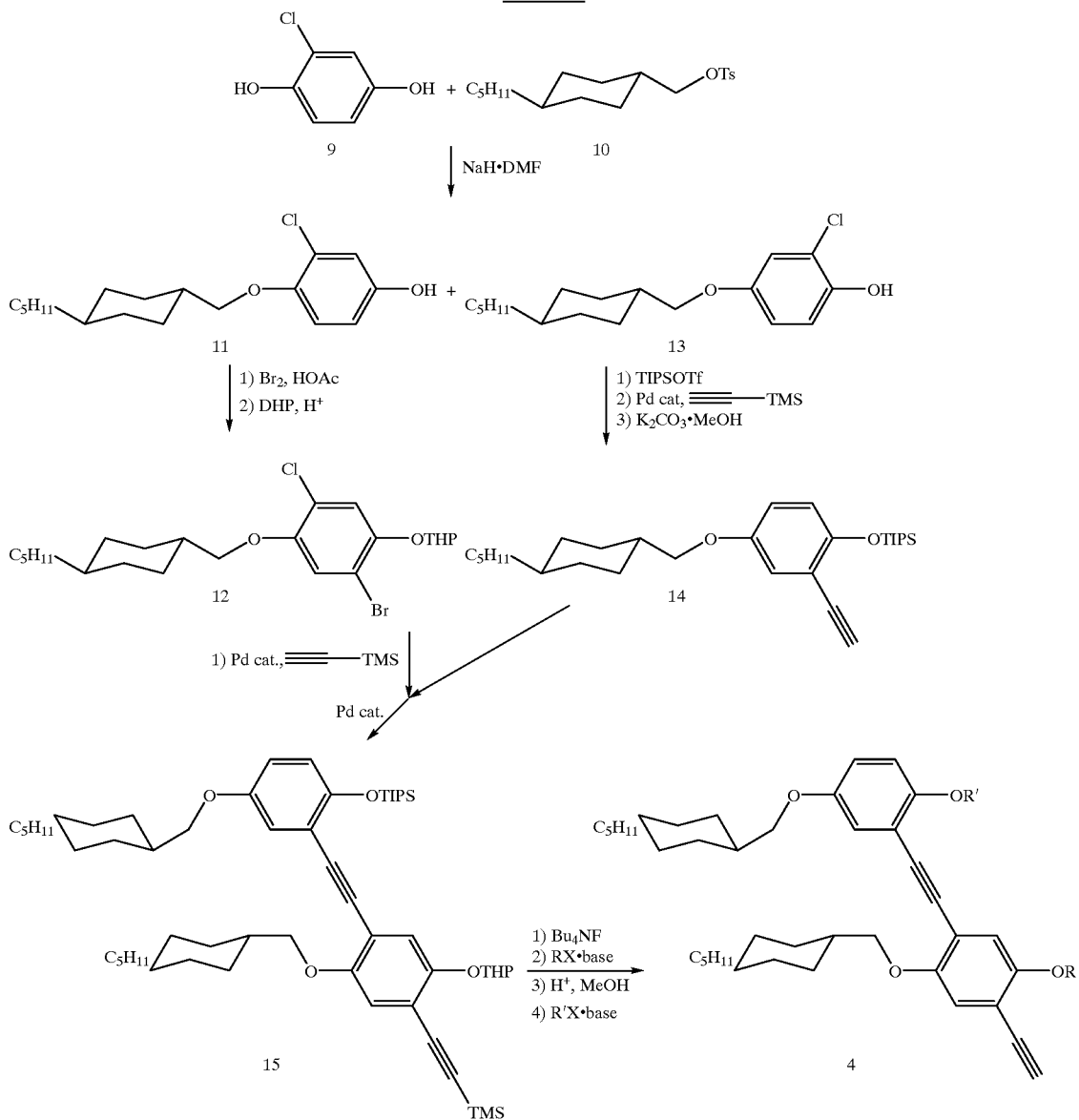

Scheme 15

The starting materials are chlorohydroquinone 9, which is commercially available, and tosylate 10. Combining the two in dimethylformamide and treating the mixture with sodium hydride gives a statistical mixture of the 3-chlorophenol 11 and the 2-chlorophenol 13. Chlorophenol 11 can then be brominated with elemental bromine in acetic acid to give the monobromide. The bromination selectively takes place at the least hindered position, para to the chlorine. Protection of the alcohol with dihydropyran will give the THP ether 12. Chlorophenol 13 can first be treated with triisopropylsilyl triflate to give the protected phenol, then alkynated with trimethylsilylacetylene, and the TMS group removed with potassium carbonate to give the acetylene 14.

Trimethylsilylacetylene should selectively react with the bromine of compound 12 to give the protected monoalkyne. This compound can then be coupled with acetylene 14 to give the alkynyltolane 15. Tetrabutylammonium fluoride removes both the TMS group from the acetylene and the TIPS group from the phenol. One tail can then be attached to the deprotected phenol. The THP group can then be removed with acid, and another tail attached to the other phenol to give product 4. Note that, using this system of protecting groups, it is possible to place different tails on the two phenols, thus making the compound less symmetrical and allowing greater versatility.

Example 1.3

Diacetylene materials are relatively unstable to UV light. However, when a cinnamate group is substituted onto placed on the material, they become remarkably stable to UV light. We believe that this remarkable stability is due to a pathway for the non-destructive release of the energy absorbed, namely cis-trans isomerization of the cinnamate double bond. This probably proceeds through a twist-state biradical, suppressing other undesired pathways that would result in decomposition. Due to binding site forces, this intermediate will be somewhat more likely to return to the trans form of the cinnamate upon recombination of the biradical. Thus, the synthesis of the more UV-stable diacetylene cinnamate is provided in the following Scheme:

Example 1.4
Instrumentation and General Procedures

Melting points and first order phase transitions were measured by differential scanning calorimetry on a Mettler (model-E) DSC. The phase diagrams were also determined by optical microscopy with a Meiji Labax CO, LTD. [Japan] (model mKI) temperature controller. Thin layer chromatography was performed on pre-coated sheets gel 60 $F_{254}$ (layer thickness 0.2 mm).

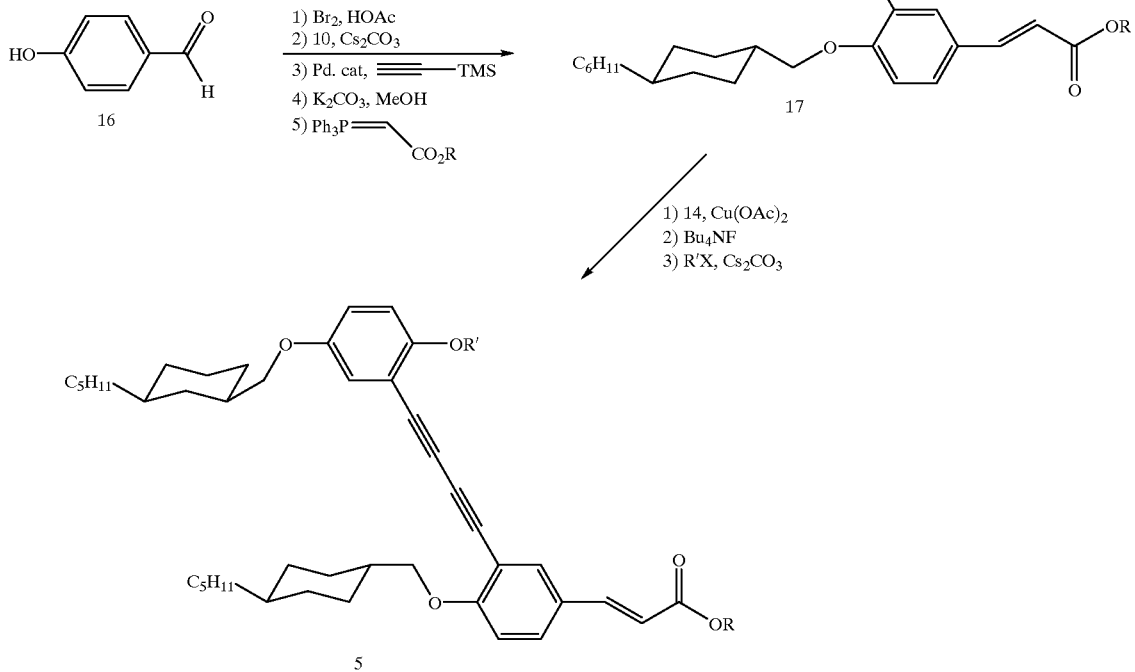

Scheme 16

The starting material for the diacetylene cinnamate is hydroxybenzaldehyde 16. Bromination with elemental bromine in acetic acid gives the monobromide, which can be alkylated using the cyclohexyl tosylate 10. The aryl bromide is alkynated with trimethylsilylacetylene and the product deprotected with potassium carbonate. The cinnamate group can be introduced by a Wittig reaction using a carboalkoxytriphenylphosphorane, which can be made using any desired alkoxy group. Since this will be a stabilized Wittig reaction, it will preferentially give the trans alkene 17. The alkyne of 17 can be coupled with the alkyne of compound 14, giving the diacetylene. Finally, the phenol can be deprotected using tetrabutylammonium fluoride, then coupled with an alkyl halide to give the desired product 5. Again, the tails used in the two monomeric portions of the molecule can be the same or different, allowing a great deal of versatility.

In several of the foregoing synthetic schemes, the cyclohexylmethylene group is used to etherify a phenol near the onset of the synthesis. Other cyclcohexy groups, including bicyclic groups with 6-membered rings which should serve equally well in this step.

Polarization measurements were made using ITO coated cells that were typically 2.8μ thick and were capillary filled with the mesogen in the isotropic state. Alignment layers were obtained by dipping the cell plates in a 0.5% methanolic solution of DuPont Elvamide followed by anti-parallel rubbing with a sable paint brush.

Most solvents were used as supplied by the vendor. Dry tetrahydrofuran was obtained by distillation from sodium. Anhydrous diethyl ether was used as supplied by the vendor. All starting materials were obtained from commercial sources unless otherwise noted.

Example 1.5
Unsaturated Alcohols

General synthesis of the alcohols. A typical procedure for the synthesis of the fatty acid derived alcohols is described. Linoleic acid (3.5 g, 12.48 mmol) dissolved in 20 ml anhydrous ether was added dropwise at 0° C. and under argon, to a suspension of LAH (947 mg, 24.9 mmol) in 280 ml anhydrous ether. The reaction mixture was stirred at 25° C. for 5 hours and was then carefully quenched at 0° C. with 5% HCl. The organic layer was separated, washed with brine, and dried over $MgSO_4$. Evaporation of solvent yielded 3.193 g (96%) of a colorless liquid. Exemplary alcohols 26a–j prepared as starting materials for synthesis of compounds of this invention are given in Table 1.

TABLE 1

Exemplary Synthesis of Alcohols from Commercially Available Fatty Acids, Aldehydes, and Carboxylic Acids RCO$_2$H $\xrightarrow[\text{Et}_2\text{O}]{\text{LAH}}$ ROH 26a R = C$_{18}$H$_{37}$— b R = H$_3$C$\diagdown\diagdown_7\diagup\diagdown_8$ c R = H$_3$C$\diagdown\diagdown_4\diagup\diagdown\diagdown_8$ d R = H$_3$C$\diagdown\diagdown_4\diagup\diagdown\diagup\diagdown_8$ e R = H$_3$C$\diagdown\diagdown\diagup\diagdown\diagup\diagdown_8$ f R = H$_3$C$\diagdown\diagdown_4\diagup\diagdown\diagup\diagdown_5$ 26 g 26 g R = C$_6$H$_{13}\diagdown\diagup\diagdown_1$ h R = C$_5$H$_{11}\diagdown\diagup\diagdown_2$ i R = C$_4$H$_9\diagdown\diagup\diagdown_3$ j R = C$_3$H$_7\diagdown\diagup\diagdown_4$ 1—Octadecanal (26a). This material is commercially available from Aldrich Chemicals.

cis-9-Octadecanol (26b). This material is commercially available from Aldrich Chemicals.

cis-9, cis-12-Octadecadienol (26c) (Linoleic acid). This material is commercially available.

trans-9, trans-12-Octadecadienol (26d) This material was obtained from Sigma Chemicals. The crude material was purified via flash chromatography over silica gel 80/20 (v/v) (Hex/EtOAc).

cis-9, cis-12, cis-15-Octadecatrienol (26e) (Linolenic acid). This material was obtained from Sigma Chemicals.

cis-6, cis-9, cis-12-Octadecatrienol (26f) (γ-Linolenic acid). This material was obtained from Sigma Chemicals.

trans-2-Decenol (26 g). This material was purchased from Lancaster Chemicals.

trans-3-Decenol (26h). The precursor carboxylic acid was obtained from Lancaster Chemicals. The carboxylic acid (3.0 g, 17.6 mmol), and LAH (1.337 mg, 35.2 mmol) in 300 ml anhydrous ether were reacted according to the general procedure. The crude alcohol was purified via flash chromatography over silica gel with gradual elutions from 98/2–50/50 (v/v %) (Hex/EtOAc). Evaporation of solvent yielded 2.32 g (84%) of a colorless oil. This was only 98% pure by NMR and was used without further purification.

trans-4-Decenol (26i). The precursor aldehyde was obtained from Lancaster Chemicals. The aldehyde (2.0 g, 12.96 mmol), and LAH (984 mg, 25.9 mmol) in 200 ml anhydrous ether were reacted according to the general procedure. The crude alcohol was purified via flash chromatography over silica gel with gradual elutions from 90/10–50/50 (v/v %) (Hex/EtOAc). This was used without further purification.

trans-5-Decenol (26j). This material was purchased from Aldrich Chemicals.

Cyanobiphenyls

Synthesis of Alkoxycyanobiphenyls.

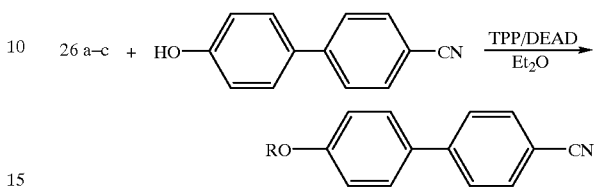

4'-(Octadecyloxy)-4-cyanobiphenyl(W400) (Hughes, D. L., "The Mitsunobu Reaction" in *Organic Reactions:* Paquette, L. A., et at., Eds., John Wiley & Sons, Inc. (1992) 42:335–656). To a suspension of 4'-hydroxy-4-biphenylcarbonitrile (Aldrich) (200 mg, 1.0 mmol), 1-octadecanol 26a (291 mg, 1.07 mmol), and triphenylphosphine (TPP) (336 mg, 1.3 mmol) in 10 ml anhydrous ether, was added diethylazodicarboxylate (DEAD) (223 mg, 1.3 mmol) via syringe with stirring and under argon. The reaction mixture was stirred for 7 hours under argon at 25° C., and was then adsorbed onto silica gel. The crude product was purified via flash chromatography with gradual elutions from 98/2 to 80/20 (v/v) (Hex/EtOAc). Evaporation of the solvent, and recrystallization from hexane yielded 322 mg (70%) of a white solid.

4'-(cis-9-Octadecenyloxy)-4-cyanobiphenyl (W396). To a suspension of 4'-hydroxy-4-biphenylcarbonitrile (500 mg, 2.56 mmol), alcohol 26b (686 mg, 2.56 mmol), and TPP (840 mg, 3.20 mmol) in 25 ml anhydrous ether was added DEAD (557 mg, 3.20 mmol) via syringe with stirring and under argon. The reaction mixture was stirred overnight under argon 25° C. The crude product was purified via flash chromatography over silica gel with elutions of 98/2, 95/5, and 90/10 (v/v) (Hex/EtOAc), respectively. Evaporation of solvent yielded 765 mg (67%) of a white solid.

4'-(cis-9, cis-12-Octadecadienyloxy)-4-cyanobiphenyl (w372). To a suspension of 4'-hydroxy-4-biphenylcarbonitrile (500 mg, 2.56 mmol), alcohol 26c (681 mg, 2.56 mmol), and TPP (1.008 g, 3.84 mmol) in 25 ml anhydrous ether was added DEAD (669 mg, 3.84 mmol) via syringe with stirring and under argon. The reaction mixture was stirred overnight under argon at 25° C. The crude product was purified via flash chromatography over silica gel with elutions of 98/2 and 95/5 (v/v) (Hex/EtOAc), respectively. Evaporation of solvent yielded 594 mg (52%) of a white liquid crystal.

Phenylpyrimidines

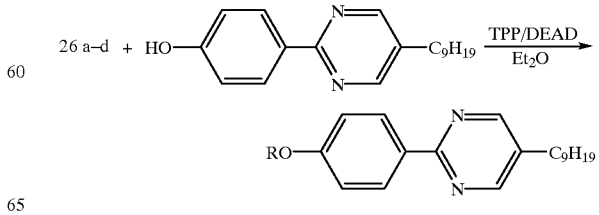

W390, 391, 397, 398

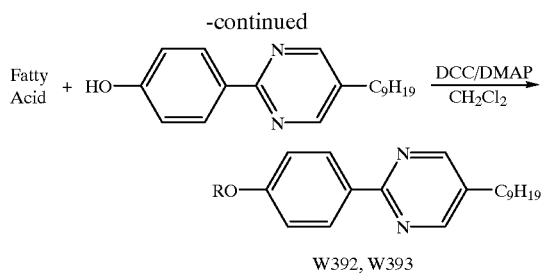

W392, W393

4'-(Octadecyloxy)-5-nonyl-2-phenylpyrimidine (W398). DEAD (115 mg, 0.66 mmol) was added via syringe with stirring and under argon to a suspension of 4'-hydroxy-5-nonyl-2-phenylpyrimidine (152 mg, 0.51 mmol), l-octadecanol 26a (152 mg, 0.56 mmol), and TPP (174 mg, 0.66 mmol) in 5 ml of anhydrous ether. The reaction mixture was stirred overnight at 25° C., and was then treated with 30% hydrogen peroxide. Ether was added (approx. 20 ml) to the reaction mixture. The organic layer was separated, washed with brine, and dried over $MgSO_4$. The crude product was concentrated and purified via flash chromatography over silica gel with elutions of 95/5, and 90/10 (v/v) (Hex/EtOAc), respectively. Evaporation of solvent yielded 205 mg (73%) of a white solid.

4'-(cis-Octadecenyloxy)-5-nonyl-2-phenylpyrimidine (W391). DEAD (109 mg, 0.63 mmol), 4'-hydroxy-5-nonyl-2-phenylpyrimidine (150 mg, 0.50 mmol), alcohol 26b (142 mg, 0.53 mmol), and TPP (165 mg, 0.63 mmol) in 5 ml of anhydrous ether were reacted according to the procedure for compound W398. The crude product was purified via flash chromatography over silica gel with elutions of 95/5, and 90/10 (v/v) (Hex/EtOAc), respectively. Evaporation of solvent yielded 154 mg (54%) of a gray liquid crystal.

4'-(cis-9, cis-12-Octadecadienyloxy)-5-nonyl-2-phenylpyrmidine (W390). DEAD (151 mg, 0.87 mmol), 4'-hydroxy-5-nonyl-2-phenylpyrimidine (200 mg, 0.67 mmol), alcohol 26c (196 mg, 0.74 mmol), and TPP (229 mg, 0.87 mmol) in 7 ml of anhydrous ether were reacted according to the procedure for compound W398. The crude product was purified via flash chromatography over silica gel with elutions of 98/2, 95/5, and 90/10 (v/v) (Hex/EtOAc), respectively. Evaporation of the solvent yielded 234 mg (64%) of a white liquid crystal.

4'-(trans-9, trans-12-Octadecadienyloxy)-5-nonyl-2-phenylpyrimidine (W397). DEAD (113 mg, 0.65 mmol), 4'-hydroxy-5-nonyl-2-phenylpyrimidine (155 mg, 0.52 mmol), alcohol 26d (145 mg, 0.55 mmol), and TPP (170 mg, 0.65 mmol) in 4 ml of anhydrous ether were reacted according to the procedure for compound W398. The crude product was purified via flash chromatography over silica gel with elutions of 95/5 and 90/10 (v/v) (Hex/EtOAc), respectively. Evaporation of solvent yielded 195 mg (69%) of a white solid.

4'-(cis-9-Octadecenoate)-5-nonyl-2-phenylpyrimidine (W393) [Neises, B. and Steglich, W., Agnew Chem. (1978) 90:556]. 1,3-Dicyclohexylcarbodiimide (DCC) (135 mg, 0.65 mmol) dissolved in 1 ml dry dichloromethane was added via syringe with stirring and under argon to a solution of 4'-hydroxy-5-nonyl-2-phenylpyrimidine (150 mg, 0.50 mmol), oleic acid (142 mg, 0.50 mmol), and 4-dimethylaminopyridine (DMAP) (18 mg, 0.15 mmol) in 4 ml dry dichloromethane. The reaction mixture was stirred overnight at 25° C. and was then treated with 5% HCl. After extraction with dichloromethane, the organic layer was washed sequentially with saturated sodium bicarbonate and brine, and dried over $MgSO_4$. The crude product was concentrated and purified via flash chromatography over silica gel with elutions of 98/2, 95/5 and 90/10 (v/v) (Hex/EtOAC), respectively. Evaporation of the solvent yielded 226 mg (80%) of a white solid.

4'-(cis-9, cis-12-Octadecadienoate)-5-nonyl-phenylpyrimidine (W392). DCC (130 mg, 0.63 mmol) dissolved in 1 ml dry dichloromethane was added via syringe with stirring and under argon to a solution of 4'-hydroxy-5-nonyl-2-phenylpyrimidine (150 mg, 0.50 mmol), linoleic acid (141 mg, 0.50 mmol), and DMAP (18 mg, 0.15 mmol) in 5 ml dry dichloromethane. The reaction mixture was stirred overnight at 25° C. and was then treated with 5% HCl. After extraction with dichloromethane, the organic layer was sequentially washed with saturated sodium bicarbonate and brine, and dried over $MgSO_4$. The crude product was concentrated and purified via flash chromatography over silica gel with elutions of 98/2, 95/5, and 90/10 (v/v) (Hex/EtOAc), respectively. Evaporation of the solvent yielded 227 mg (81%) of a gray liquid crystal.

Biphenylcarboxylates (S)-[4"-(1-Methylheptyloxy)-3"-nitrophenyl]-4'-octadecyloxy-4-biphenylcarboxylate (W374). The acid chloride derived from 29a (500 mg, 1.0 mmol) was dissolved in 15 ml of dry THF and added via syringe with stirring and under argon, to a solution of 33 (see below) (275 mg, 1.0 mmol) and triethylamine (1 15 mg, 1.1 mmol), in 10 ml dry THF. The mixture was stirred overnight at 25° C. under argon, followed by treatment with 5% HCl and extraction with chloroform. The organic layer was washed sequentially with saturated $NaHCO_3$ and brine and dried over $MgSO_4$. The crude product was concentrated and purified via flash chromatography over silica gel 90/10 (v/v) (Hex/EtOAc) to yield 544 mg (74%) of a light yellow waxy solid. The product was recrystallized from hexanes.

Scheme 17

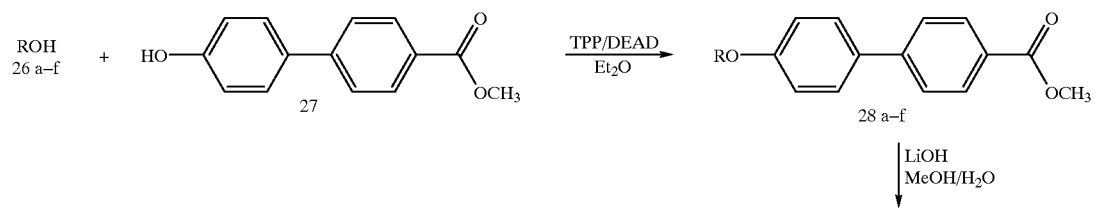

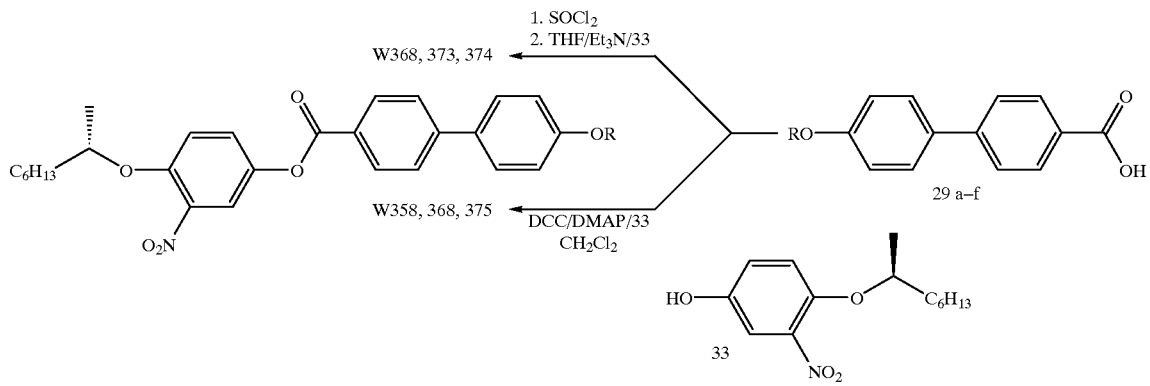

(S)-[4"-(1-Methylheptyloxy)-3"-nitrophenyl]-4'-(cis-9-octadecenyloxy)-4-biphenylcarboxylate (W368). The acid chloride derived from 29b (172 mg, 0.36 mmol) was dissolved in 2 ml of dry THF and added via syringe with stirring and under argon, to a solution of 33 (95 mg, 0.36 mmol) and triethylamine (73 mg, 0.72 mmol), in 4 ml dry THF. The mixture was stirred overnight at 25° C. under argon, followed by treatment with 5% HCl and extraction with chloroform. The organic layer was sequentially washed with saturated NaHCO₃ and brine and dried over MgSO₄. The crude product was concentrated and purified (via flash chromatography over silica gel 90/10 (v/v) (Hex/EtOAc). Evaporation of solvent yielded 200 mg (79%) of a light yellow solid.

(S)-[4"-(1-Methylheptyloxy)-3"-nitrophenyl]-4'-(cis-9, cis-12-octadecadienyloxy)-4-biphenylcarboxylate (W358). With stirring and under argon, DCC (312 mg, 1.51 mmol) dissolved in 1 ml dry dichloromethane was added via syringe to a suspension of carboxylic acid 29c (232 mg, 0.50 mmol), 33 (141 mg, 0.529 mmol), and DMAP (12 mg, 0.10 mmol) in 8 ml dry dichloromethane. The solution turned milky yellow during the addition, and the reaction mixture was stirred under argon for two days at 25° C. Dichloromethane (20 ml) was then added and the reaction mixture was treated with 5% HCl. The organic layer was washed sequentially with 5% HCl, saturated NaHCO₃, and brine, and dried over MgSO₄. The crude product was purified by flash chromatography over silica gel with gradual elutions from 98/2 to 80/20 (v/v) (Hex/EtOAc). Evaporation of solvent yielded 170 mg (47%) of a light yellow liquid crystalline material.

(S)-[4"-(1-Methylheptyloxy)-3"-nitrophenyl]-4'-(cis-9, cis-12, cis-15-octadecatrienyloxy)-4-biphenylcarboxylate (W359). With stirring and under argon, DCC (374 mg, 1.80 mmol) dissolved in 5 ml dry dichloromethane was added via syringe to a suspension of carboxylic acid 29e ((278 mg, 0.60 mmol), 33 (170 mg, 0.63 mmol), and DMAP (15 mg, 0.012 mmol) in 10 ml dry dichloromethane. The solution turned milky yellow during the addition and the reaction mixture was stirred for 12 hours at 25° C., under argon. Dichloromethane (approx. 30 ml) was added and the reaction mixture was treated with 5% HCl. The organic layer was sequentially washed with saturated NaHCO₃ and brine, and was dried over MgSO₄. The crude product was purified by flash chromatography over silica gel with gradual elutions from 98/2 to 90/10 (v/v) (Hex/EtOAc). Evaporation of the solvent yielded 330 mg (77%) of a light yellow crystalline material.

(S)-[4"-(1-Methylheptyloxy)-3"-nitrophenyl]-4'-(cis-6, cis-9, cis-12-octadecatrienyloxy)-4-biphenylcarboxylate (W373). The acid chloride derived from 29f (228 mg, 0.48 mmol) was dissolved in 3 ml of dry THF, and added via syringe with stirring and under argon, to a solution of 33 (127 mg, 0.48 mmol) and triethylamine (58 mg, 0.57 mmol), in 7 ml dry THF. The reaction mixture was stirred overnight at 25° C., was then treated with 5% HCl and extracted with ether. The organic layer was washed with saturated NaHCO₃, followed by brine, and dried over MgSO₄. The crude product was concentrated and purified via flash chromatography over silica gel with gradual elutions from 95/5 to 90/10 (v/v) (Hex/EtOAc). Evaporation of solvent yielded 163 mg (48%) of a light yellow liquid crystalline material.

(S)-[4"-(1-Methylheptyloxy)-3"-nitrophenyl]-4'-(trans-9, trans-12-octadecadienyloxy)-4-biphenylcarboxylate (W375). DCC (138 mg, 0.67 mmol) dissolved in 2 ml dry dichloromethane was added via syringe with stirring and under argon, to a solution of 33 (89 mg, 0.33 mmol), carboxylic acid 29d (155 mg, 0.33 mmol), DMAP (12 mg, 0.1 mmol), and camphorsulfonic acid (4 mg, 0.017 mmol) in 5 ml dry dichloromethane. The reaction mixture was stirred for 48 hours at 25° C. under argon and was then treated with 5% HCl. The reaction mixture was extracted with dichloromethane and the organic layer was washed with saturated sodium bicarbonate followed by brine, and dried over MgSO₄. The crude product was purified via flash chromatography over silica gel with elutions of 98/2, 95/5, and 90/10 (v/v) (Hex/EtOAc), respectively. Evaporation of the solvent yielded 111 mg (47%) of a light yellow solid.

Biphenylcarboxylic Acid Intermediates

Methyl-4'-hydroxy-4-biphenylcarboxylate (27). Concentrated sulfuric acid (approximately 4 ml) was carefully added to a solution of 4'-hydroxy-4-biphenylcarboxylic acid (Aldrich) (8.20 g, 38.3 mmol) in 1 liter of methanol. The reaction mixture was refluxed for three days and the solvent was evaporated. The resulting solid was filtered, washed with water, and recrystallized as follows. The crude solid was dissolved in a minimum amount of hot THF, and approximately three equivalents of methanol was added to the solution. The solution was brought to a boil, and water was added with vigorous stirring until the solution remained cloudy. After cooling, the tan precipitate was filtered, washed with cold ethanol, and air dried to yield 7.57 g (86%) of a tan solid.

Methyl-4'-octadecyloxy-4-biphenylcarboxylate (28a). Potassium carbonate (1.695 g, 12.3 mmol) and cesium carbonate (799 mg, 2.4 mmol) were added to a solution of the tosylate of 26a (2.60 g, 6.1 mmol), and ester 27 (1.468 g, 6.4 mmol) in 60 ml of dry DMF. The solution was stirred for 48 hours at 25° C. and was then poured over 200 ml crushed ice. Acidification with 5% HCl resulted in a tan precipitate which was filtered, washed with water, and air dried. The product was recrystallized from 80/20 (v/v) (Hex/THF) to yield 2.272 g (77%) of a tan powder.

Methyl-4'-(cis-9-octadecenyloxy)-4-biphenylcarboxylate (28b). DEAD (676 mg, 3.88 mmol) was added via syringe with stirring and under argon, to a solution of ester 27 (590 mg, 2.59 mmol), alcohol 26b (707 mg, 2.64 mmol), and TPP (1.018 g, 3.88 mmol) in 8 ml dry THF. The reaction mixture was stirred overnight under argon at 25° C. and then treated with 30% hydrogen peroxide. Ether was added (approximately 20 ml) and the organic layer was separated, washed with brine, and dried over $MgSO_4$. The crude product was adsorbed onto silica gel and purified via flash chromatography with elutions of 95/5 and 90/10 (v/v) (Hex/EtOAc), respectively. Evaporation of solvent yielded 505 mg (41%) of a white solid.

Methyl-4'-(cis-9,cis-12-octadecadienyloxy)-4-biphenylcarboxylate (28c). DEAD (818 mg, 4.70 mmol) was slowly added via syringe, with stirring and under argon, to a solution of ester 27 (857 mg, 3.76 mmol), alcohol 26c (1.0 g, 3.76 mmol), and triphenylphosphine (1.232 g, 4.70 mmol) in 31 ml dry THF. The reaction mixture was stirred overnight and was then treated with 30% $H_2O_2$. Ether was added (approximately 30 ml) and the organic layer was separated, washed with brine, and dried over $MgSO_4$. The solvent was evaporated and the crude product was adsorbed onto silica gel and purified via flash chromatography with gradual elutions from 98/2 to 90/10 (v/v) (Hex/EtOAc). Evaporation of solvent yielded 1.411 g (79%) of a white solid.

Methyl-4'-(trans-9,trans-12-octadecadienyloxy)-4-biphenylcarboxylate (28d). DEAD (392 mg, 2.25 mmol) was slowly added via syringe, with stirring and under argon, to a solution of ester 27 (343 mg, 1.5 mmol), alcohol 26d (400 mg, 1.5 mmol), and TPP (592 mg, 2.25 mmol) in 11 ml anhydrous ether. The reaction mixture was stirred overnight under argon at 25° C. and then was treated with 30% $H_2O_2$. Ether was added (approximately 20 ml) and the organic layer was separated, washed with brine, and dried over $MgSO_4$. The crude product was concentrated and purified via flash chromatography over silica gel, with elutions of 98/2, 95/5 and 90/10 (v/v) (Hex/EtOAc), respectively. Evaporation of solvent yielded 214 mg (30%) of a white solid.

Methyl-4'-(cis-9,cis-12,cis-15-octadecatrienyloxy)-4-biphenylcarboxylate (28e). DEAD (463 mg, 2.66 mmol) was slowly added via syringe, with stirring and under argon, to a solution of ester 27 (406 mg, 1.78 mmol), alcohol 26e (469 mg, 1.78 mmol), and TPP (699 mg, 2.66 mmol) in 30 ml dry THF. The reaction mixture was refluxed for 24 hours, cooled and treated with 30% $H_2O_2$. Ether was added (approximately 20 ml) and the organic layer was separated, washed with brine, and dried over $MgSO_4$. The solvent was evaporated and the crude product was purified via flash chromatography over silica gel 90/10 (v/v, Hex/EtOAc). Evaporation of solvent yielded 324 mg (38%) of a white solid.

Methyl-4'-(cis-6,cis-9,cis-12-octadecatrienyloxy)-4-biphenylcarboxylate (28f). DEAD (763 mg, 4.38 mmol) was added via syringe, with stirring and under argon, to a solution of ester 27 (800 mg, 3.5 mmol), alcohol 26f (926 mg, 3.5 mmol), and TPP (1.150 g, 4.38 mmol) in 25 ml dry THF. The reaction mixture was stirred overnight under argon at 25° C. and then was treated with 30% $H_2O_2$. Ether was added (approximately 20 ml) and the organic layer was separated, washed with brine, and dried over $MgSO_4$. The crude product was adsorbed onto silica gel and purified via flash chromatography with gradual elutions from 95/5 to 80/20 (v/v) (Hex/EtOAc). Evaporation of solvent yielded 1.034 g (62%) of a light yellow waxy solid.

4'-Octadecyloxy-4-biphenylcarboxylic acid (29a). Lithium hydroxide monohydrate (874 mg, 20.8 mmol) was added to a suspension of the ester 28a (2.00 g, 4.17 mmol), 50 ml water, and 200 ml THF. The mixture was refluxed for 48 hours and then was acidified with concentrated HCl. Water (150 ml) was added and the solution was cooled. The resulting tan precipitate was filtered and washed with water. The tan precipitate was dissolved in 100 ml hot THF and hexanes were added until the solution remained cloudy with stirring. After cooling, crystals were filtered to yield 1.4 g of a light yellow solid, and a second crop of crystals was isolated for a total yield of 1.67 g (86%). The product was used without further purification.

4'-(cis-9-octadecenyloxy)-4-biphenylcarboxylic acid (29b). Water (approximately 15 ml) was added to a solution of ester 28b (486 mg, 1.00 mmol) in 50 ml of an 80/20 (v/v) (methanol/THF) solution, until it remained milky white with vigorous stirring. To this suspension was added lithium hydroxide monohydrate (213 mg, 5.1 mmol), the reaction mixture was refluxed overnight and then was acidified with concentrated HCl. Water (approximately 20 ml) was added and the solution was cooled, filtered, washed several times with water, and air dried, yielding 422 mg (89%) of a white waxy powder.

4'-(cis-9,cis-12-octadecadienyloxy)-4-biphenylcarboxylic acid (29c). To ester 28c (989 mg, 2.07 mmol) was added 100 ml of an 80/20 (v/v) (methanol/THF) solution. With vigorous stirring, water (approximately 20 ml) was added until the solution remained milky white. To this suspension was added lithium hydroxide monohydrate (436 mg, 10.4 mmol), the reaction mixture was refluxed for 6 hours and then acidified with concentrated HCl. Water (approximately 50 ml) was added, the reaction mixture was cooled, filtered, and washed several times with water to yield 933 mg (97%) of a white waxy powder. The crude product was used without further purification.

4'-(trans-9,trans-12-octadecadienyloxy)-4-biphenylcarboxylic acid (29d). To ester 28d (211 mg, 0.44 mmol) was added 40 ml of an 80/20 (v/v) (methanol/THF) solution. Water (approximately 5 ml) was added with vigorous stirring until the solution remained milky white. To this suspension was added lithium hydroxide monohydrate (93 mg, 2.2 mmol), the reaction mixture was refluxed overnight and was then acidified with concentrated HCl. Water (approximately 20 ml) was added and the reaction mixture was cooled, filtered and the product was washed several times with water. The product was air dried yielding 172 mg (84%) of a white powder.

4'-(cis-9,cis-12,cis-15-octadecatrienyloxy)-4-biphenylcarboxylic acid (29e). To ester 28e (320 mg, 0.67 mmol) was added 50 ml of an 80/20 (v/v) (methanol/THF) solution. With vigorous stirring, water (approximately 10 ml) was added until the solution remained milky white. To this suspension was added lithium hydroxide monohydrate (142 mg, 3.34 mmol), the reaction mixture was refluxed for six hours and was then acidified with concentrated HCl. Water (approximately 20 ml) was added, the reaction mixture was cooled, filtered, washed several times with water, and air dried to yield 282 mg (91%) of a white waxy powder.

4'-(cis-6,cis-9,cis-12-octadecatrienyloxy)-4-biphenylcarboxylic acid (29f). To ester 28f (230 mg, 0.48 mmol) was added 30 ml of an 80/20 (v/v) (methanol/THF) solution. With vigorous stirring, water was added until the solution remained milky white (approximately 5 ml). To this suspension was added lithium hydroxide monohydrate (102 mg, 2.4 mmol), the reaction mixture was refluxed overnight and was then acidified with concentrated HCl. Water (approximately 15 ml) was added, the reaction mixture was cooled, filtered, washed several times with water, and air dried to yield 220 mg (99%) of a light yellow waxy powder.
Hydroquinone Fragment peroxide. The organic layer was separated, washed with brine, and dried over magnesium sulfate. The crude product was purified via flash chromatography over silica gel (90/10, v/v, Hex/EtOAc) to yield 2.99 g (87%) of a yellow oil.

4-(Heptyloxy)-3-nitro-phenylbenzoate (32b). DEAD (222 mg, 1.27 mmol), phenol 31 (250 mg, 1.02 mmol), 1-heptanol (130 mg, 1.12 mmol), and TPP (334 mg, 1.27 mmol) in 10 ml anhydrous ether were reacted according to

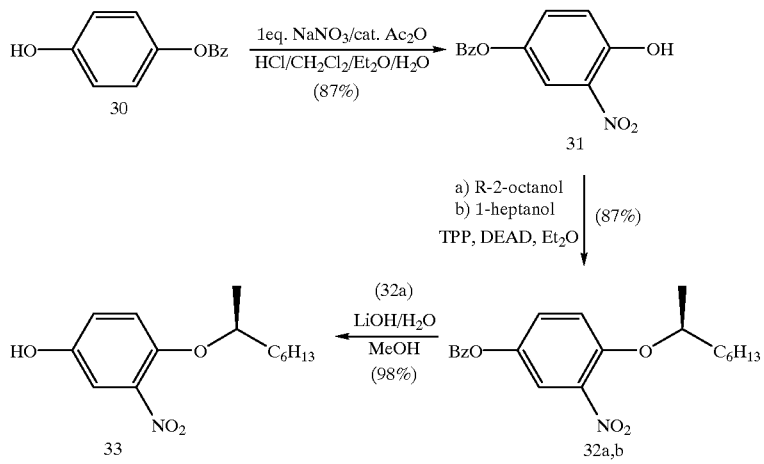

4-(Hydroxy)-phenylbenzoate (30). This material was obtained from Lancaster Chemicals.

4-(Hydroxy)-3-(nitro)-phenylbenzoate (31) [Keller, P., Bull. Soc. Chim. Fr. (1994) 131:27]. To a solution of 4-(hydroxy)-phenylbenzoate 30 (8.0 g, 37.38 mmol), $NaNO_3$ (3.336 g, 39.25 mmol), 45 ml $H_2O$, 75 ml dichloromethane, and 150 ml ether, was carefully added 9 ml concentrated HCl. With vigorous stirring acetic anhydride (1 ml) was added. The reaction mixture was stirred overnight and then the organic layer was separated, washed with brine, and dried over magnesium sulfate. Evaporation of solvent yielded an orange powder which was recrystallized twice from ethanol to yield 7.304 g of yellow crystals. The mother liquor was concentrated and purified via flash chromatography over silica gel (30/60/10, v/v/v, dichloromethane/Hex/EtOAc) to yield an additional 1.103 g product. Total yield was 8.407 g (87%) of a yellow solid.

(S)-4-(1-Methylheptyloxy)-3-nitro-phenylbenzoate (32a). DEAD (2.42 g, 13.9 mmol) was added via syringe with stirring and under argon to a solution of 31 (2.41 g, 9.3 mmol), TPP (3.66 g, 13.9 mmol), and (R)-2-octanol in 120 ml of anhydrous ether. The reaction mixture was stirred overnight at 25° C. and then was treated with 30% hydrogen the procedure for compound 32a. The crude material was purified via flash chromatography over silica gel with gradual elutions from 95/5–90/10 (v/v) (Hex/EtOAc). Evaporation of solvent yielded 294 mg (84%) of a light green oil.

(S)-4-(1-methylheptyloxy)-3-nitrophenol (33). Compound 32a (380 mg, 1.02 mmol) was dissolved in 10 ml methanol, and water (approximately 3 ml) was added until the solution remained milky yellow with vigorous stirring. Lithium hydroxide monohydrate (258 mg, 6.1 mmol) was added, the reaction mixture was stirred for six hours at 25° C., and then was acidified with concentrated HCl. The reaction mixture was extracted with dichloromethane (30 ml). The organic layer was separated, washed with saturated sodium bicarbonate, followed by brine, and dried over magnesium sulfate. The solvent was evaporated and the crude product was purified via flash chromatography over silica gel (50/50, v/v, Hex/EtOAc) to yield 269 mg (98%) of an orange oil.

Biphenylbenzoates

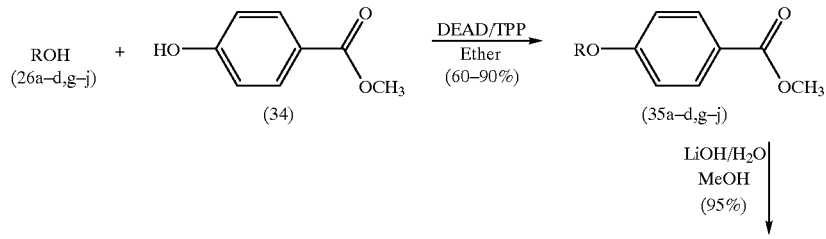

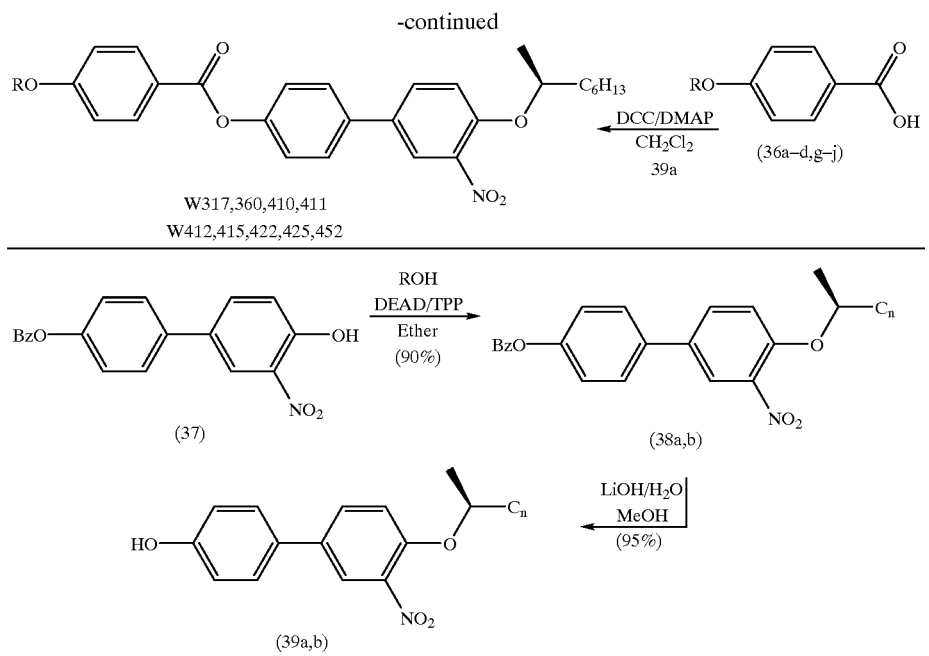

(S)-[4'-(1-Methylheptyloxy)-3'-(nitro)-biphenyl]-4-octadecyloxy-benzoate (W412). DCC (143 mg, 0.69 mmol) dissolved in 1 ml dichloromethane was added via syringe, with stirring and under argon, to a solution of the acid 36a (254 mg, 0.63 mmol), the phenol 39a (226 mg, 0.66 mmol), and DMAP (31 mg, 0.25 mmol) in 10 ml dichloromethane. The reaction mixture was stirred overnight at 25° C. and then was treated with 5% HCl. Dichloromethane (approximately 15 ml) was added, and the organic layer was separated, washed with saturated $NaHCO_3$, followed by brine, and dried over $MgSO_4$. The crude product was purified via flash chromatography over silica gel with gradual elutions from 98/2 to 80/20 (v/v) (Hex/EtOAc). Evaporation of the solvent yielded 275 mg (59%) of a yellow solid. The product was then recrystallized from hexanes.

(S)-[4'-(1-Methylheptyloxy)-3'-(nitro)-biphenyl]-4-(cis-9-octadecenyloxy)benzoate (W452). The phenol 39a (130 mg, 0.379 mmol), carboxylic acid 36b (162 mg, 0.42 mmol), DCC (94 mg, 0.45 mmol), and DMAP (18 mg, 0.15 mmol) in 4 ml dichloromethane were reacted according to the procedure for compound W412. The crude product was purified via flash chromatography over silica gel with gradual elutions from 98/2–90/10 (v/v, Hex/EtOAc). Evaporation of the solvent yielded 195 mg (72%) of a light green liquid crystalline material. This was precipitated from hexanes.

(S)-[4'-(1-Methylheptyloxy)-3'-(nitro)-biphenyl]-4-(cis-9, cis-12-octadecadienyloxy)benzoate (W360). DCC (235 mg, 1.14 mmol), carboxylic acid 36c (220 mg, 0.568 mmol), phenol 39a (195 mg, 0.568 mmol), and DMAP (28 mg, 0.228 mmol) in 6 ml dichloromethane were reacted according to the procedure for compound W412. The crude product was purified via flash chromatography over silica gel with gradual elutions from 98/2 to 80/20 (v/v, Hex/EtOAc). Evaporation of the solvent yielded 290 mg (72%) of a yellow-green liquid crystalline material. This was precipitated from hexanes.

(S)-[4'-(1-Methylheptyloxy)-3'-(nitro)-biphenyl]-4-(trans-9, trans-12-octadecadienyloxy)-benzoate (W410). DCC (195 mg, 0.95 mmol), carboxylic acid 36d (333 mg, 0.86 mmol), phenol 39a (310 mg, 0.90 mmol), and DMAP (42 mg, 0.34 mmol) in 8 ml dichloromethane were reacted according to the procedure for compound W412. The crude product was purified via flash chromatography over silica gel with gradual elutions from 98/2 to 80/20 (v/v, Hex/EtOAc). Evaporation of the solvent yielded 460 mg (75%) of a yellow-green liquid crystalline material. This was precipitated from hexanes.

(S)-[4'-(1-Methylheptyloxy)-3'-(nitro)-biphenyl]-4-decyloxybenzoate (W317). The synthesis and physical data of this material have been reported elsewhere. (See WO 92/03427.)

(S)-[4'-(1-Methylheptyloxy)-3'-(nitro)-biphenyl]-4-(trans-2-decenyloxy)-benzoate (W422). The phenol 39a (310 mg, 0.90 mmol), carboxylic acid 36 g (250 mg, 0.90 mmol), DCC (205 mg, 0.99 mmol), and DMAP (44 mg, 0.36 mmol) in 9 ml dichloromethane were reacted according to the procedure for compound W412. The crude product was purified via flash chromatography over silica gel with gradual elutions from 95/5–90/10 (v/v) (Hex/EtOAc). Evaporation of the solvent yielded 393 mg (72%) of a light green liquid crystalline material. This was precipitated from hexanes.

(S)-[4'-(1-Methylheptyloxy)-3'-(nitro)-biphenyl] -4-(trans-3-decenyloxy)-benzoate (W425). The phenol 39a (394 mg, 1.15 mmol), carboxylic acid 36h (317 mg, 1.15 mmol), DCC (260 mg, 1.25 mmol), and DMAP (56 mg, 0.46 mmol) in 12 ml dichloromethane were reacted according to the procedure for compound W412. The crude product was purified via flash chromatography over silica gel with gradual elutions from 95/5–90/10 (v/v, Hex/EtOAc). Evaporation of the solvent yielded 536 mg (78%) of a light green liquid crystalline material. This was precipitated from hexanes.

(S)-[4'-(1-Methylheptyloxy)-3'-(nitro)-biphenyl]-4-(trans-4-decenyloxy)-benzoate (W411). DCC (274 mg, 1.33 mmol), carboxylic acid 36i (334 mg, 1.21 mmol), phenol 39a (436 mg, 1.27 mmol), and DMAP (59 mg, 0.48 mmol) in 12 ml dichloromethane were reacted according to the procedure for compound W412. The crude product was purified via flash chromatography over silica gel with gradual elutions from 98/2 to 80/20 (v/v, Hex/EtOAc). Evaporation of the solvent yielded 549 mg (76%) of a yellow-green liquid crystalline material. This was precipitated from hexanes.

Benzoic Acid Fragment

Methyl-4-octadecyloxy-benzoate (35a). DEAD (400 mg, 2.3 mmol) was slowly added via syringe, with stirring and under argon, to a solution of the phenol 34 (281 mg, 1.85 mmol), alcohol 26a (500 mg, 1.85 mmol), and TPP (606 mg, 2.3 mmol) in 18 ml anhydrous ether. The reaction mixture was stirred overnight at 25° C. and then treated with 30% hydrogen peroxide. Ether was added (10 ml), the organic layer was separated, washed with brine, and dried over $MgSO_4$. The crude product was concentrated and purified via flash chromatography over silica gel (95/5, v/v, Hex/EtOAc and 5% dichloromethane). Evaporation of the solvent yielded 544 mg (73%) of a colorless liquid.

Methyl-4-(cis-9,cis-12-octadecadienyloxy)-benzoate (35c). DEAD (515 mg, 2.96 mmol), phenol 34 (300 mg, 1.97 mmol), alcohol 26c (551 mg, 2.07 mmol), and TPP (776 mg, 2.96 mmol) in 16 ml anhydrous ether were reacted according to the procedure for compound 35a. The crude product was purified via flash chromatography over silica gel 95/5 (Hex/EtOAc). Evaporation of the solvent yielded 582 mg (74%) of colorless liquid.

Methyl-4-(trans-9,trans-12-octadecadienyloxy)-benzoate (35d). DEAD (515 mg, 2.96 mmol), phenol 34 (300 mg, 1.97 mmol), alcohol 26d (551 mg, 2.07 mmol), and TPP (776 mg, 2.96 mmol) in 16 ml anhydrous ether were reacted according to the procedure described for compound 35a. The crude product was purified via flash chromatography over silica gel with gradual elutions from 98/2 to 90/10 (v/v, Hex/EtOAc). Evaporation of the solvent yielded 575 mg (73%) of colorless liquid.

Methyl-4-(trans-2-decenyloxy)-benzoate (35 g). Phenol 34 (486 mg, 3.2 mmol), 2-decenol 26 g (500 mg, 3.2 mmol), TPP (965 mg, 3.68 mmol), and DEAD (641 mg, 3.68 mmol) in 32 ml ether were reacted according to the procedure for compound 35a. The crude product was purified via flash chromatography over silica gel with gradual elutions from 95/5–90/10 (v/v, Hex/EtOAc). Evaporation of solvent yielded 603 mg (65%) of colorless needles.

Methyl-4-(trans-3-decenyloxy)-benzoate (35h). Ester 34 (500 mg, 3.29 mmol), 3-decenol 26h (514 mg, 3.29 mmol), TPP (992 mg, 3.78 mmol), DEAD (658 mg, 3.78 mmol), and 33 ml ether were reacted according to the procedure for compound 35a. The crude product was purified via flash chromatography over silica gel with gradual elutions from 95/5–90/10 (v/v, Hex/EtOAc). Evaporation of solvent yielded 810 mg (85%) of colorless liquid which was not quite pure. The product was used without further purification.

Methyl-4-(trans-4-decenyloxy)-benzoate (35i). DEAD (641 mg, 3.68 mmol), phenol 34 (487 mg, 3.2 mmol), alcohol 26i (500 mg, 3.2 mmol), and TPP (966 mg, 3.68 -mmol) in 16 ml anhydrous ether were reacted according to the procedure for compound 35a. The crude product was purified via flash chromatography over silica gel with gradual elutions from 95/5 to 90/10 (v/v, Hex/EtOAc). Evaporation of the solvent yielded 748 mg (80%) of colorless liquid.

Methyl-4-(trans-5-decenyloxy)-benzoate (35j). DEAD (256 mg, 1.47 mmol), phenol 34 (194 mg, 1.28 mmol), alcohol 26j (200 mg, 1.28 mmol), and TPP (386 mg, 1.47 mmol) in 13 ml anhydrous ether were reacted according to the procedure for compound 35a. The crude product was purified via flash chromatography over silica gel with gradual elutions from 95/5 to 90/10 (v/v, Hex/EtOAc). Evaporation of the solvent yielded 266 mg (72%) of colorless liquid.

4-octadecyloxy-benzoic acid (36a). The ester 35a (405 mg, 1.0 mmol) was dissolved in 15 ml THF and 50 ml methanol was added. Water (approximately 10 ml) was added until the solution remained cloudy with vigorous stirring, at which time lithium hydroxide monohydrate (840 mg, 20.0 mmol) was added. The reaction mixture was refluxed overnight, acidified with concentrated HCl and cooled. The precipitate was filtered, washed with water and air dried to yield 279 mg (71%) of a white powder.

4-(cis-9, cis-12-octadecadienyloxy)-benzoic acid (36c). The starting ester 35c (520 mg, 1.3 mmol) was dissolved in 40 ml THF. Water (approximately 10 ml) was added until the solution remained cloudy, at which time lithium hydroxide monohydrate (273 mg, 6.5 mmol) was added. The reaction mixture was refluxed overnight, acidified with concentrated HCl and extracted with ether. The organic layer was washed with brine and dried over $MgSO_4$. Evaporation of the solvent yielded 481 mg (96%) of a viscous white liquid crystalline material. Further purification was possible via flash chromatography (50/50, v/v, Hex/EtOAc) over silica gel, however the crude product was sufficiently pure to be used in the next step.

4-(trans-9, trans-12-octadecadienyloxy)-benzoic acid (36d). The ester 35d (491 mg, 1.23 mmol) was dissolved in 40 ml THF. Water (approximately 10 ml) was added until the solution remained cloudy, at which time lithium hydroxide monohydrate (257 mg, 6.1 mmol) was added. The reaction mixture was refluxed overnight, acidified with concentrated HCl and extracted with ether. The organic layer was washed with brine and dried over $MgSO_4$. The crude product was purified via flash chromatography over silica gel (50/50, v/v, Hex/EtOAc) to yield 380 mg (80%) of a white solid.

4-(trans-2-Decenyloxy)-benzoic acid (36 g). The ester 35 g 565 mg, 1.95 mmol), and lithium hydroxide monohydrate (817 mg, 19.5 mmol) in 20 ml methanol were reacted according to the procedure for compound 36a. The yield was 482 mg (89% of a white powder.

4-(trans-3-Decenyloxy)-benzoic acid (36h). Ester 35h (600 mg, 2.07 mmol), and lithium hydroxide monohydrate (867 mg, 20.7 mmol) in 20 ml methanol were reacted according to the procedure for compound 36a. The yield was 500 mg (87%) of a white powder which was not quite pure (95%). The product was used without further purification.

4-(trans-4-decenyloxy)-benzoic acid (36i). The ester 35i (500 mg, 1.7 mmol) was dissolved in 50 ml methanol. Water (approximately 10 ml) was added until the solution remained cloudy, at which time lithium hydroxide monohydrate (723 mg, 17.0 mmol) was added. The reaction mixture was refluxed overnight and acidified with concentrated HCl. Water was added (approximately 30 ml), the mixture was cooled, filtered, washed with water and allowed to air dry yielding 400 mg (84%) of a white powder.

4-(trans-5-decenyloxy)-benzoic acid (36j). The ester 35j (240 mg, 0.83 mmol) was dissolved in 15 ml methanol. Water (approximately 2 ml) was added until the solution remained cloudy with vigorous stirring, at which time lithium hydroxide monohydrate (347 mg, 8.3 mmol) was added. The reaction mixture was refluxed overnight and acidified with concentrated HCl. Water was added (approximately 10 ml), the mixture was cooled, filtered, washed with water and allowed to air dry yielding 183 mg (80%) of a white powder.

Biphenol Fragment

4'-(hydroxy)-3'-(nitro)-4-biphenylbenzoate (37). Concentrated nitric acid (0.36 ml) was added over a 30 minute period to a cooled suspension (5–10° C.) of 4'-(benzoyl)-4-biphenol [Naciri, J. et al., *Chem. Mater.* (1995) 7:1397] (500 mg, 1.7 mmol) in 12 ml glacial acetic acid. The reaction mixture was stirred for 1 hour as it slowly warmed to room temperature, then water was added and the reaction mixture was cooled. The resulting precipitate was filtered, washed with water and air dried. The product was recrystallized from a solution of ethanol/THF (3/1, v/v) to yield 455 mg of product. The mother liquor was then adsorbed onto silica gel and purified via flash chromatography [50/45/5, v/v/v, Hex/dichloromethane/EtOAc]. Evaporation of solvent yielded an additional 100 mg, for a total yield of 555 mg (97%) of a yellow solid.

4'-(1-Methylheptyloxy)-3'-(nitro)-4-biphenylbenzoate (38a). Phenol 37 (700 mg, 2.1 mmol), R-2-octanol (340 mg, 2.6 mmol), TPP (821 mg, 3.1 mmol), and DEAD (545 mg, 3.1 mmol) in 21 ml dry THF were reacted according to the procedure for compound 35a. The crude product was purified via flash chromatography over silica gel [50/45/5, v/v/v, Hex/dichloromethane/EtOAc]. Evaporation of solvent yielded 833 mg (89%) of a viscous yellow oil.

(S)-4'-(1-Methylnonyloxy)-3'-(nitro)-4-biphenylbenzoate (38b). Phenol 37 (529 mg, 1.58 mmol), R-2-decanol (250 mg, 1.58 mmol), TPP (621 mg, 2.37 mmol), and DEAD (412 mg, 2.37 mmol) in 16 ml dry THF were reacted according to the procedure for compound 35a. The crude product was purified via flash chromatography over silica gel with gradual elutions from 95/5–80/20 (v/v, Hex/EtOAc). Evaporation of solvent yielded 504 mg (67%) of a light green viscous oil.

4'-(1-Methylheptyloxy)-3'-(nitro)-4-biphenol (39a). Ester 38a (288 mg, 0.64 mmol) was dissolved in 10 ml THF and 5 ml methanol. Water was added with vigorous stirring until the solution remained cloudy, followed by the addition of lithium hydroxide monohydrate (135 mg, 3.2 mmol). The reaction mixture was stirred overnight and was then acidified with concentrated HCl. The reaction mixture was separated with ether. The organic layer was washed with brine and dried over $MgSO_4$. The crude product was purified via flash chromatography over silica gel [60/40, v/v, Hex/EtOAc]. Evaporation of solvent yielded 190 mg (86%) of a viscous orange oil.

(S)-4'(1-Methylnonyloxy)-3'-(nitro)-4-biphenol (39b). Ester 38b (470 mg, 0.989 mmol), and lithium hydroxide monohydrate (207 mg, 4.90 mmol) in 20 ml THF were reacted according to the procedure for compound 39a. The crude product was purified via flash chromatography over silica gel with gradual elutions from 80/20–50/50 (v/v, Hex/EtOAc). Evaporation of solvent yielded 321 mg (88%) of a viscous orange oil.

Example 1.6

Electroclinic Tilt Measurements

Electroclinic tilt angles were measured using a DC field supplied by a low frequency square wave generator. The cell was rotated to extinction and the field was then reversed. The cell was rotated back to extinction to yield 2θ. The LC cells varied from the commercially available 4μ Hamlin type cell, to standard ITO glass slides coated with a rubbed nylon alignment layer and separated with glass spacers of known thickness.

Example 1.7

Dichroic Ratio Measurements

The visible light dichroic measurements were performed on a Hewlett Packard model HP 8452 diode array spectrometer, fitted with a temperature controller (Model: HP 8909A). The cells consisted of two glass plates coated with a rubbed nylon alignment layer. A rotating polarizing stage was fitted between the cell and the light source.

Example 1.8

Bis-Chiral Tailed Biphenylcarboxylates (S,S)-[4"-(1-Methylheptyloxy)-3"-nitrophenyl]-4'-(1-methylheptyloxy)-3'-(nitro)-4-biphenylcarboxylate (W363). DCC (193 mg, 0.93 mmol), carboxylic acid 42a (315 mg, 0.85 mmol), phenol 33 (238 mg, 0.89 mmol), and DMAP (41 mg, 0.34 mmol) in 7 ml dichloromethane were reacted according to the procedure for compound 16. The crude product was purified via flash chromatography over silica gel with gradual elutions from 95/5 to 65/35 (Hex/EtOAc). Evaporation of the solvent yielded 410 mg (78%) of a yellow solid, which was then precipitated from hexanes.

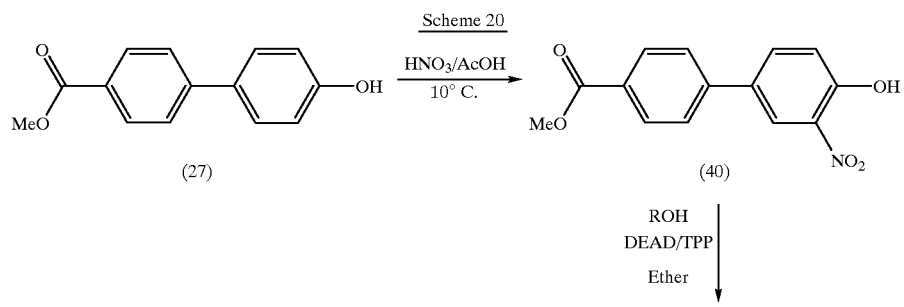

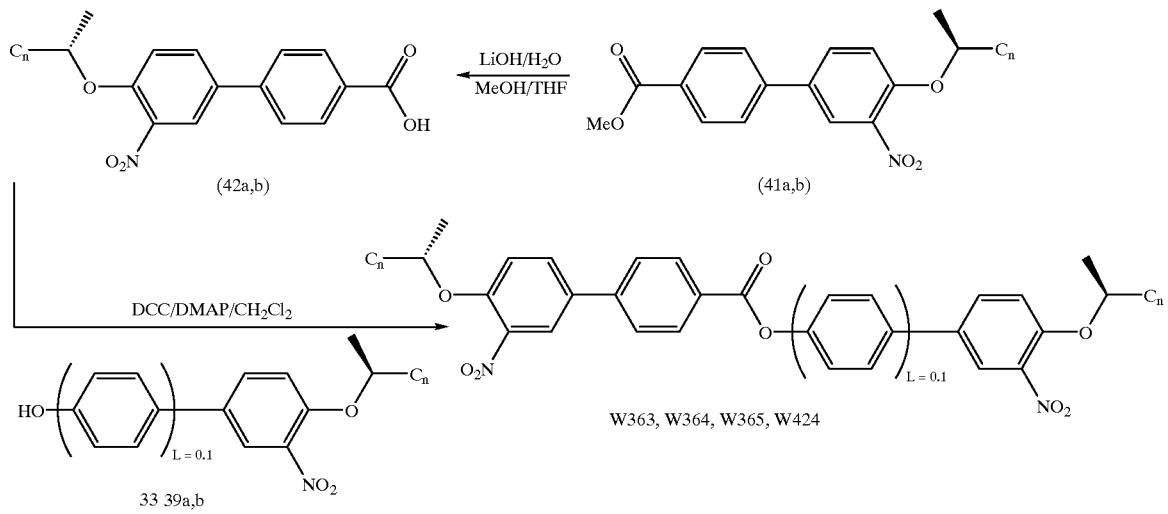

(S,S)-[4'''-(1-Methylheptyloxy)-3'''-(nitro)-biphenyl]-4'-(1-methylheptyloxy)-3'-(nitro)-4-biphenylcarboxylate (W364). DCC (306 mg, 1.48 mmol), carboxylic acid 42a (500 mg, 1.35 mmol), phenol 39a (485 mg, 1.41 mmol), and DMAP (66 mg, 0.54 mmol) in 13 ml dichloromethane were reacted according to the procedure for compound 16. The crude product was purified via flash chromatography over silica gel with gradual elutions from 98/2 to 65/35 (Hex/EtOAc). Evaporation of the solvent yielded 760 mg (81%) of a yellow solid, which was then precipitated from hexanes.

(S,S)-[4''-(1-Methylheptyloxy)-3'''-nitrophenyl]-4'-(1-methylnonyloxy)-3'-(nitro)-4-biphenylcarboxylate (W365). DCC (57 mg, 0.27 mmol), carboxylic acid 42b (100 mg, 0.25 mmol), phenol 33 (67 mg, 0.25 mmol), and DMAP (12 mg, 0.10 mmol) in 3 ml dichloromethane were reacted according to the procedure for compound 16. The crude product was purified via flash chromatography over silica gel with gradual elutions from 95/5 to 80/20 (Hex/EtOAc). Evaporation of the solvent yielded 102 mg (63%) of a yellow solid, which was then precipitated from hexanes.

(S,S)-[4'''-(1-Methylnonyloxy)-3'''-(nitro)-biphenyl]-4'-(1-methylnonyloxy)-3'-(nitro)-4-biphenylcarboxylate (W424). Carboxylic acid 42b (100 mg, 0.25 mmol), phenol 39b (93 mg, 0.25 mmol), DCC (65 mg, 0.31 mmol), and DMAP (15 mg, 0.12 mmol) in 4 ml dichloromethane was reacted according to the procedure for compound 16. The crude product was purified via flash chromatography over silica gel with gradual elutions from 95/5–50/50 (Hex/EtOAc). Evaporation of solvent yielded 137 mg (73%) of a yellow solid, which was then precipitated from hexanes.

o-Nitro-Biphenylcarboxylic Acid Fragment

Methyl-4'-(hydroxy)-3'-(nitro)-4-biphenylcarboxylate (40). Concentrated nitric acid (1.8 ml) was carefully added to a cooled suspension (5–10° C.) of phenol 27 (2.0 mg, 8.8 mmol) in 60 ml of glacial acetic acid. The reaction mixture was stirred for one hour and was then allowed to warm to room temperature and stirred for an additional 30 minutes. Water was added (50 ml) and the reaction mixture was cooled, filtered, and washed with water to yield a yellow powder. The crude product was purified via flash chromatography through a small pad of silica gel with elutions of 80/20 and 50/50 (Hex/EtOAc), respectively. Evaporation of the solvent yielded 2.23 g (93%) of a bright yellow solid.

(S)-Methyl-4'-(1-methylheptyloxy)-3'-(nitro)-4-biphenylcarboxylate (41a). DEAD (1.097 g, 6.3 mmol), phenol 40 (1.50 g, 5.5 mmol), R-2-octanol (751 mg, 5.77 mmol), and TPP (1.657 g, 6.3 mmol) in 55 ml anhydrous ether were reacted according to the procedure for compound 35a. The crude product was concentrated and purified via flash chromatography over silica gel with gradual elutions from 90/10 to 65/35 (Hex/EtOAc). Evaporation of the solvent yielded 1.90 g (90%) of yellow solid.

(S)-Methyl-4'-(1-methylnonyloxy)-3'-(nitro)-4-biphenylcarboxylate (41b). DEAD (323 mg, 1.85 mmol), phenol 40 (440 mg, 1.61 mmol), R-2-decanol (268 mg, 1.69 mmol), and TPP (486 mg, 1.85 mmol) in 16 ml anhydrous ether were reacted according to the procedure for compound 35a. The crude product was concentrated and purified via flash chromatography over silica gel with gradual elutions from 95/5 to 65/35 (Hex/EtOAc). Evaporation of the solvent yielded 439 mg (66%) of a yellow solid.

(R)-Methyl-3'-(nitro)-4'-(1-methylheptyloxy)-4-biphenylcarboxylate (41c). DEAD (151 mg, 0.87 mmol), TPP (228 mg, 0.87 mmol), phenol 40 (190 mg, 0.69 mmol), and S-2-octanol (95 mg, 0.73 mmol) in 7 ml anhydrous ether were reacted according to the procedure for compound 35a. The crude product was purified via flash chromatography over silica gel with gradual elutions from 90/10 to 50/50 (Hex/EtOAc). Evaporation of solvent yielded 183 mg (68%) of a light yellow solid.

(S)-4'-(1-Methylheptyloxy)-3'-(nitro)-4-biphenylcarboxylic acid (42a). Ester 41a (1.679 g, 4.36 mmol) was dissolved in 10 ml of THF, and with vigorous stirring methanol (40 ml) was added, followed by water (approximately 10 ml) until the solution remained milky white. To this suspension was added lithium hydroxide monohydrate (1.83 g, 43.6 mmol). The reaction mixture was refluxed overnight and was then acidified with concentrated HCl. Brine was added, the reaction mixture was extracted with ether and the organic layer was washed with brine and dried over $MgSO_4$. Evaporation of the solvent yielded 1.486 g (92%) of a light yellow solid.

(S)-4'-(1-Methylnonyloxy)-3'-(nitro)-4-biphenylcarboxylic acid (42b). Ester 41b (390 mg, 0.94 mmol) was dissolved in 3 ml THF and 15 ml methanol. Water was added with vigorous stirring until the solution remained cloudy, followed by the addition of lithium hydroxide monohydrate (56 mg, 1.30 mmol). After refluxing overnight, the solution was acidified with concentrated HCl and extracted with ether. The organic layer was washed with brine and dried over $MgSO_4$. Evaporation of the solvent yielded 323 mg (86%) of a yellow solid.

Example 1.9

Azo-Dyes: Side by Side Dimers
Mixed Tolan-Biphenylcarboxylate System (S)-[4"-(1-Methylheptyloxy)-5"-(N,N-dimethylamino)-2"-[(S)-2'"-(1-methylheptyloxy)-5'"-[4""-carboxy-(4"""-dodecyloxyphenyl)-phenylacetylenyl]-4'"-nitro-phenylazo]-phenyl]-4'-(decyloxy)-4-biphenylcarboxylate (W421)

[Stephens, R. D. and Castro, C., *J. Org. Chem.* (1963) 28:3313; Sonogashira, K. et al., *Tet. Lett.* (1975) 50:4467]. To a solution of the azo-dye 46 (266 mg, 0.265 mmol) and the acetylide 47 (129 mg, 0.318 mmol) in pyridine (27 ml), was added copper iodide (20 mg), copper(acetate)$_2$ monohydrate (20 mg), and tetrakis(triphenylphosphine)palladium (0) catalyst (50 mg). The reaction mixture was stirred for 48 hours at 25° C. Ethyl acetate (approximately 15 ml) was added, followed by brine, and the organic layer was separated. The organic layer was washed twice with 10% HCl, followed by saturated sodium bicarbonate and brine. After drying over $MgSO_4$, the crude product was adsorbed onto silica gel and purified via flash chromatography with gradual elutions from 90/5/5 to 80/15/5 (v/v/v) (Hex/EtOAc/dichloromethane). Evaporation of the solvent yielded 79 mg (23%) of a red solid. An additional 123 mg of the starting azo-dye was recovered for an adjusted yield of 43%.

Scheme 21

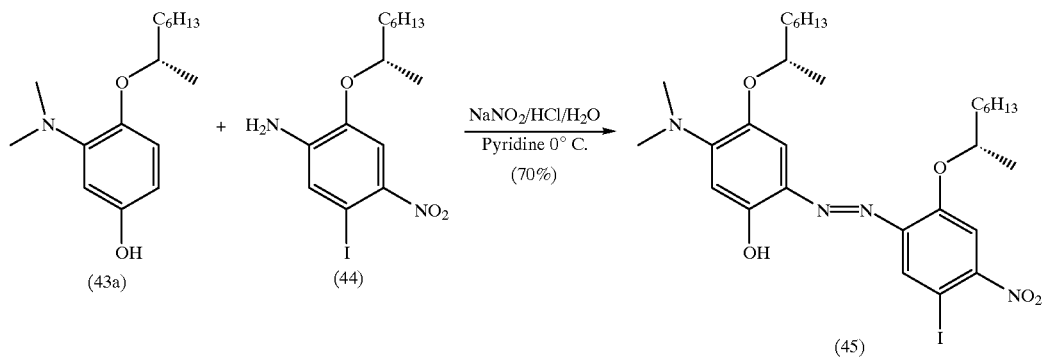

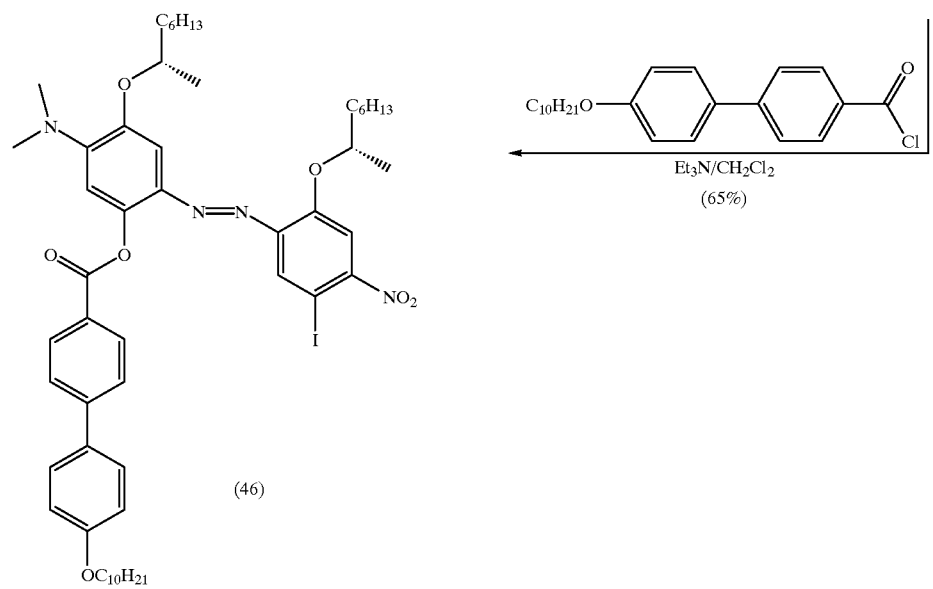

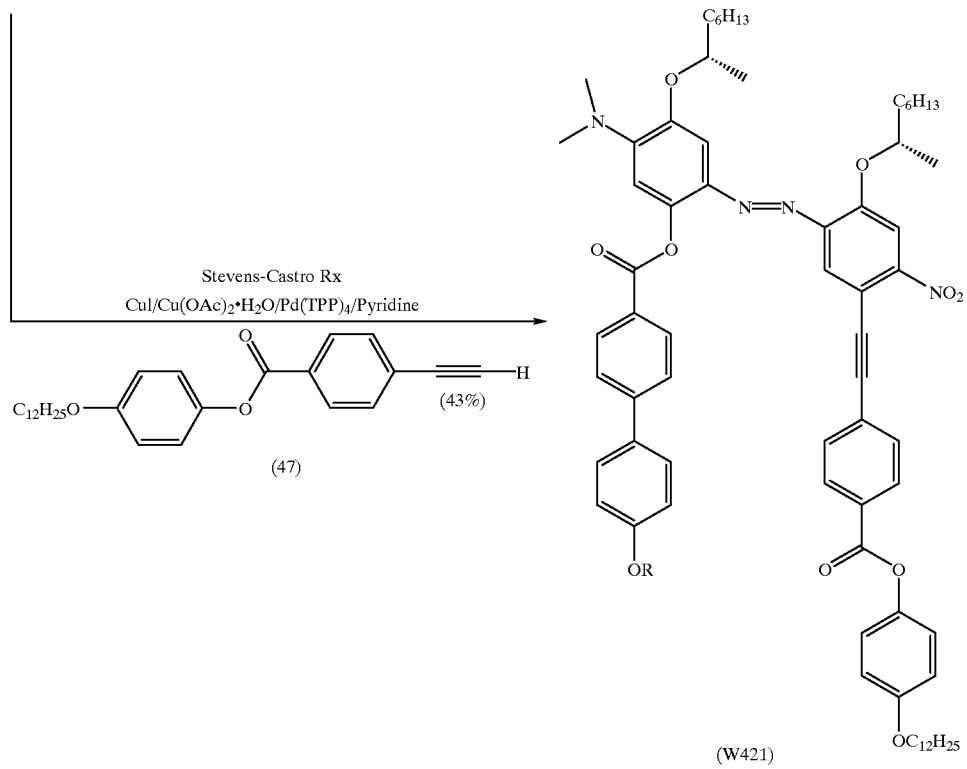

(S)-4-(1-Methylheptyloxy)-3-(N,N-dimethylamino)-phenol (43a) [Hunig, S. and Baron, W., Ber. (1957) 90:395]. Iodomethane (16 ml, 257 mmol) was added to a stirred solution of analine 48a (1.10 g, 3.22 mmol), anhydrous potassium carbonate (1.337 g, 9.67 mmol), and DMF (32 ml). The reaction mixture was stirred for 2 hours at 25° C. and the excess iodomethane was evaporated off. Ethanolamine (65 ml) was added and the reaction mixture was refluxed (165° C.) for 2 hours. The reaction mixture was cooled, diluted with water, and extracted twice with ethyl acetate. The combined organic layers were washed with brine and dried over $MgSO_4$. The crude product was concentrated and purified via flash chromatography over silica gel, with gradual elutions from 80/20 to 50/50 (Hex/EtOAc). Evaporation of solvent yielded 695 mg (81%) of a yellow oil.

(S)-4-(1-Methylheptyloxy)-3-(N,N-dimethyl)-aminophenol (43b). Methyl iodide (7.9 ml), compound 48b (551 mg, 1.68 mmol), ethanolamine (34 ml), and potassium carbonate (698 mg), in 16 ml DMF were reacted according to the procedure for compound 43a. The crude product was purified via flash chromatography over silica gel with gradual elutions from 80/20–50/50 (Hex/EtOAc). Evaporation of solvent yielded 260 mg (61%) of a viscous yellow oil.

(S)-5-Iodo-4-nitro-2-(1-methylheptyloxy)-aniline (44). The synthesis and physical data of this compound are described elsewhere (WO 92/20058).

(S)-4-(1-Methylheptyloxy)-5-[(S)-5'-(1-methylheptyloxy)-2'-(hydroxy)-4'-(N,N-dimethylamino)-phenylazo]-2-nitro-1-iodobenzene (45). Compound 44 (300 mg, 0.77 mmol) was dissolved in 20 ml of a 15% concentrated HCl/ethanol solution and was then cooled to 0° C. with an ice-salt water bath. To this solution, sodium nitrite (7.7 ml of a 0.1 M solution in water) was slowly added dropwise at a rate to maintain the temperature at or below 2° C. (approximately 20 minutes). To this cooled solution was added the dimethyl analine 43a (210 mg, 0.77 mmol) dissolved in 4 ml dichloromethane. Pyridine (2.4 ml) was slowly added dropwise at a rate to maintain the temperature below 2° C. (approximately 20 minutes). An additional 15 ml dichloromethane was added to increase the solubility, the reaction mixture was stirred for one hour at 0° C. and then was allowed to warm to room temperature over an additional 30 minutes. The organic layer was separated and the aqueous portion was extracted with dichloromethane. The combined organic layers were washed with 5% HCl, followed by brine and dried over $MgSO_4$. The crude product was adsorbed onto silica gel and purified via flash chromatography (80/20 hexanes/EtOAc). Evaporation of the solvent yielded 360 mg (70%) of a metallic green solid.

(S)-[4"-(1-Methylheptyloxy)-5"-(N,N-dimethylamino)-2"-[(S)-2'"-(1-methylheptyloxy)-5'"-iodo-4'"-nitro-phenylazo]-phenyl]-4'-(decyloxy)-4-biphenylcarboxylate (46). The acid chloride 29 (373 mg, 1.0 mmol) dissolved in 5 ml dichloromethane was added via syringe with stirring and under argon to a solution of the azo-dye (550 mg, 0.82 mmol), and triethylamine (100 mg, 0.98 mmol) in 95 ml dichloromethane. The reaction mixture was stirred at 25° C. for 16 hours and was then treated with 10% HCl. The organic layer was separated, washed with brine and dried over $MgSO_4$. The crude product was purified via flash chromatography over silica gel (90/10 hexanes/EtOAc). Evaporation of the solvent yielded 535 mg (65%) of a dark purple solid.

4-(Dodecyloxy)-4'-ethynyl-phenylbenzoate (47). The synthesis and physical properties of this compound have been described elsewhere (WO 92/20058).

Bis-Biphenylcarboxylate DR1 System

Example 1.10

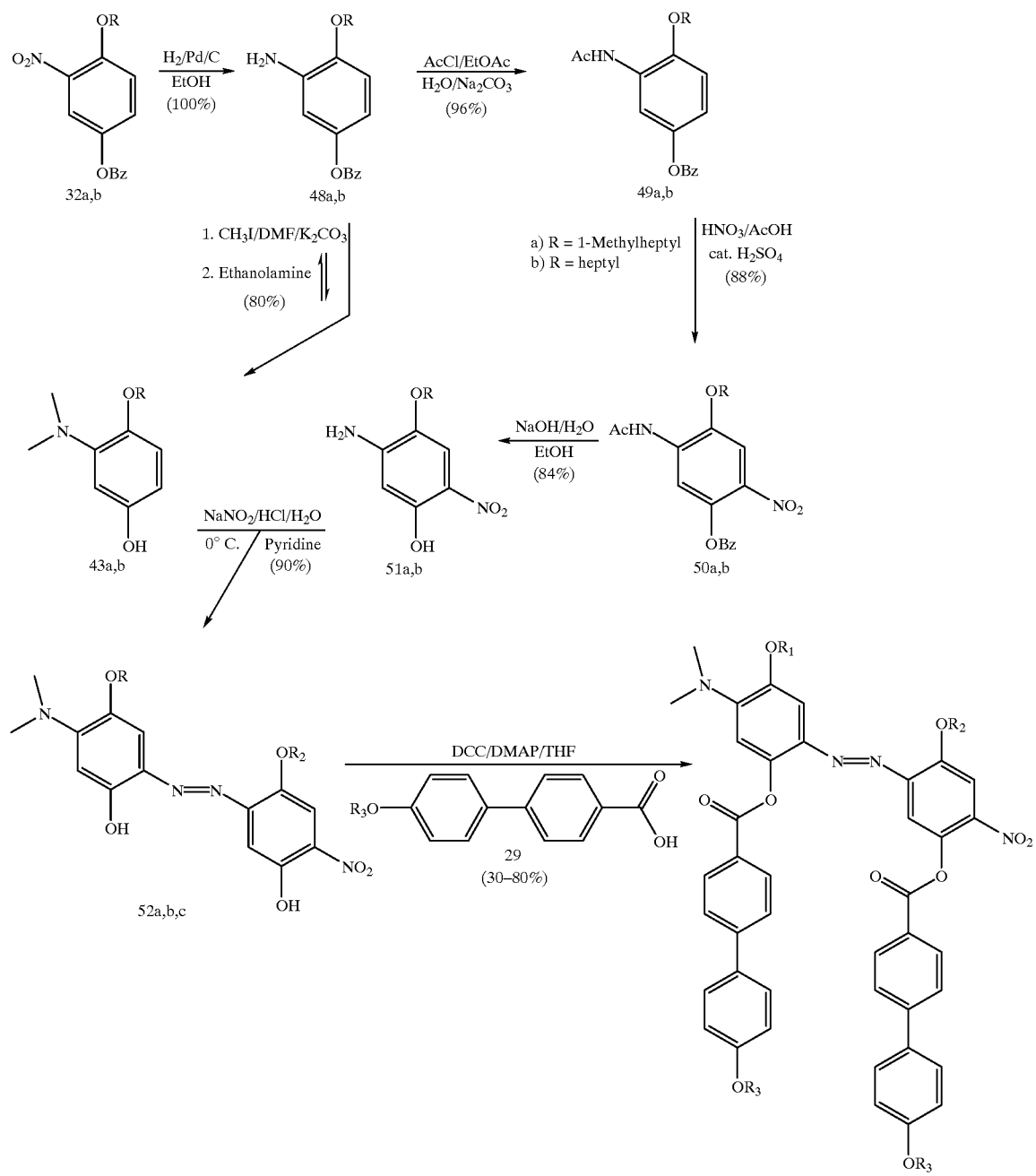

Scheme 22

(S)-[4"-(1-Methyl-heptyloxy)-5"-[(S)-5'"-(1-methyl-heptyloxy)-2'"-hydroxy-4'"-(N,N-dimethylamino)-phenylazo]-2",-nitro]-bis-(1",2'")-4'-(cis-9, cis-12-octadecadieneyloxy)-4-biphenylcarboxylate (W427). DCC (106 mg, 0.51 mmol) dissolved in 1 ml dichloromethane was added, via syringe with stirring and under argon, to a solution of the carboxylic acid of 29c (190 mg, 0.41 mmol), 52a (115 mg, 0.20 mmol), and DMAP (13 mg, 0.10 mmol) in 4 ml dichloromethane. The reaction mixture was stirred overnight at 25° C. and was then treated with 5% HCl. The organic layer was separated and the aqueous layer was extracted with dichloromethane. The combined organic layers were washed with brine and dried over $MgSO_4$. TLC of the crude product showed mostly starting material, and NMR confirmed that the major products were the mono-substituted azo dyes. The crude product was dissolved in dichloromethane (4 ml), and DMAP (13 mg, 0.10 mmol) was added followed by triethylamine (40 mg, 0.40 mmol).

The acid chloride of 29c (144 mg, 0.30 mmol) dissolved in 1 ml dichloromethane was added via syringe with stirring and under argon. The reaction mixture was stirred overnight at 25° C. and the previous workup was repeated. The crude product was purified via flash chromatography over silica gel with gradual elutions from 90/5/5 to 80/15/5 (v/v/v, Hex/EtOAc/dichloromethane). Evaporation of solvent yield 186 mg (31%) of a dark red solid.

(S)-[4"-(1-Methyl-heptyloxy)-5"-[(S)-5'"-(1-methyl-heptyloxy)-2'"-hydroxy-4'"-(N,N-dimethyamino)-phenylazo]-2"-nitro]-bis-(1',2'")-4'-(decyloxy)-4-biphenylcarboxylate (W429). 4'-(decyloxy)-4-biphenyl-acid chloride (140 mg, 0.376 mmol) dissolved in 1.5 ml dichloromethane was added via syringe, with stirring and under argon, to a solution of 52a (100 mg, 0.179 mmol), triethylamine (45 mg, 0.448 mmol), and DMAP (11 mg, 0.09 mmol) in 2.5 ml dichloromethane. The reaction mixture was stirred overnight at 25° C. and was then treated with 5% HCl. Dichloromethane (approximately 20 ml) was added, the organic layer was separated and washed with saturated sodium bicarbonate, followed by brine, and dried over MgSO$_4$. The crude product was adsorbed onto silica gel and purified via flash chromatography with gradual elutions from 90/5/5 to 80/15/5 (hexanes/ethyl acetate/dichloromethane). Evaporation of the solvent yielded 173 mg (79%) of a dark red solid.

(S)-[4"-(1-Methyl-heptyloxy)-5"-[5'"-(heptyloxy)-2'"-hydroxy-4'"-(N,N-dimethylamino)-phenylazo]-2"-nitro]-bis-(1",2'")-4'-(cis-9, cis-12-octadecadieneyloxy)-4-biphenylcarboxylate (W438). DCC (174 mg, 0.84 mmol) dissolved in 0.5 ml dry THF was carefully added via syringe, with stirring and under argon, to a solution of azo-dye 52b (184 mg, 0.338 mmol), carboxylic acid 29c (343 mg, 0.74 mmol), and DMAP (25 mg, 0.20 mmol) in 3 ml dry THF. The reaction mixture was stirred overnight and then was treated with 5% HCl, and extracted with dichloromethane. The organic layer was washed with brine and dried over MgSO$_4$. The crude product was adsorbed onto silica gel and purified via flash chromatography with gradual elutions from 90/5/5 to 75/20/5 (hexanes/ethyl acetate/dichloromethane). Evaporation of solvent yielded 278 mg (57%) of a dark red solid. This was then precipitated from hexanes.

[4"-(Heptyloxy)-5"-[(S)-5'"-(1-methyl-heptyloxy)-2'"-hydroxy-4'"-(N,N-dimethylamino)-phenylazo]-2"-nitro]-bis-(1",2'")-4'-(cis-9, cis-12-octadecadieneyloxy)-4-biphenylcarboxylate (W439). DCC (213 mg, 1.03 mmol) dissolved in 1 ml dry THF was carefully added via syringe, with stirring and under argon, to a solution of azo-dye 52c (225 mg, 0.413 mmol), carboxylic acid 29c (420 mg, 0.91 mmol), and DMAP (40 mg, 0.33 mmol) in 5 ml dry THF. The reaction mixture was stirred for 48 hours and then was treated with 5% HCl and extracted with dichloromethane. The organic layer was washed with brine and dried over MgSO$_4$. The crude product was adsorbed onto silica gel and purified via flash chromatography with gradual elutions from 90/5/5 to 75/20/5 (hexanes/ethyl acetate/dichloromethane). Evaporation of solvent yielded 277 mg (47%) of a dark red solid. This was then precipitated from hexanes.

Bis-Phenol DR1 Fragment (S)-4-(1-Methylheptyloxy)-3-amino-phenylbenzoate (48a). Compound 32a (1.195 g, 3.22 mmol) was dissolved in ethanol (32 ml), and a small scoop of 10% Pd/C was added. The reaction flask was evacuated and filled with hydrogen three times. The reaction mixture was stirred under hydrogen (balloon) atmosphere overnight and then was filtered through a pad of celite. Evaporation of solvent yielded 1.10 g (100%) of a viscous brown oil. The crude product was used without further purification.

4-(Heptyloxy)-3-amino-phenylbenzoate (48b). A small scoop of 10% Pd/C catalyst was added to a solution of 32b (1.744 g, 4.88 mmol) in 50 ml ethanol. The flask was evacuated and filled with hydrogen three times. The reaction mixture was stirred overnight under hydrogen balloon atmosphere, then filtered through a pad of celite. Evaporation of solvent yielded 1.523 g (95%) of a brown solid.

(S)-4-(1-Methyl-heptyloxy)-3-(N-acetyl)amino-phenylbenzoate (49a). Acetyl chloride (1.04 ml, 14.6 mmol) was carefully added to a stirred solution of 48a (500 mg, 1.46 mmol) in 15 ml ethyl acetate, and 30 ml of a 10% aqueous Na$_2$CO$_3$ solution. The reaction mixture was stirred for 20 minutes and then an additional 1.04 ml of acetyl chloride was added. The reaction mixture was stirred for two hours, the organic layer was then separated, washed with brine, and dried over MgSO$_4$. Evaporation of the solvent yielded 538 mg (96%) of a red-brown viscous oil. The crude product was used without purification.

4-(heptyloxy)-3-(N-acetyl)amino-phenylbenzoate (49b). Acetyl chloride (2.11 ml, 29.6 mmol) was slowly added to a stirred solution of 48b in 30 ml ethyl acetate and 60 ml of a 10% aqueous sodium carbonate solution. The reaction mixture was stirred for 30 minutes and then an additional 2.1 ml of acetyl chloride was added. Stirring was continued for one hour, the organic layer was then separated, washed with brine, and dried over MgSO$_4$. Evaporation of solvent yielded 937 mg (86%) of an orange solid. The crude product was used without purification.

(S)-4-(1-Methylheptyloxy)-5-(N-acetyl)amino-2-nitro-phenylbenzoate (50a). A solution of concentrated nitric acid (0.47 ml) and glacial acetic acid (2.6 ml) was carefully added at 0° C. to a stirred solution of 49a (300 mg, 0.78 mmol) in 16 ml glacial acetic acid and 0.7 ml concentrated sulfuric acid. The reaction mixture was stirred for 20 minutes as it warmed to room temperature. Water (approximately 100 ml) was added and the reaction mixture was extracted twice with dichloromethane. The combined organic layers were washed with brine and dried over MgSO$_4$. Evaporation of the solvent yielded 294 mg (88%) of a yellow solid. The crude product was used without purification.

4-(Heptyloxy)-5-(N-acetyl)amino-2-nitro-phenylbenzoate (Sob). A solution of concentrated nitric acid (1.45 ml) and glacial acetic acid (8 ml) was slowly added at 5–10° C. to a stirred solution of 49b (893 mg, 2.42 mmol) in 50 ml glacial acetic acid. The reaction mixture was allowed to warm to room temperature over a 30 minute period. Water was then added, and the solution was extracted with dichloromethane. The organic layer was washed with brine and dried over MgSO$_4$. Evaporation of solvent yielded 893 mg (89%) of an orange solid. The crude product was used without purification.

(S)-4-(1-Methylheptyloxy)-2-nitro-5-aminophenol (51a). Sodium hydroxide (687 mg, 17.2 mmol) was carefully added to a stirred solution of 50a (294 mg, 0.69 mmol), water (8 ml), and ethanol (25 ml). The reaction mixture was stirred overnight at 25° C. and then was neutralized with concentrated HCl. The resulting solution was extracted twice with dichloromethane, and the combined organic layers were washed with brine and dried over MgSO$_4$. The crude product was concentrated and purified via flash chromatography over silica gel with gradual elutions from 90/10 to 80/20 (v/v, Hex/EtOAc). Evaporation of the solvent yielded 164 mg (84%) of an orange oil which eventually solidified.

4-(Heptyloxy)-2-nitro-5-aminophenol (51b). Sodium hydroxide (2.15 g, 53.7 mmol) was carefully added to a stirred solution of 50b (890 mg, 2.15 mmol) in 80 ml ethanol and 20 ml water. The reaction mixture was stirred overnight and was then acidified with concentrated HCl. Extracted three times with dichloromethane, and the combined organic layers were washed with brine and dried over $MgSO_4$. The crude product was adsorbed onto silica gel and purified via flash chromatography with gradual elutions from 85/10/5 to 75/20/5 (Hex/EtOAc/dichloromethane). Evaporation of solvent yielded 469 mg (81%) of an orange solid.

(S)-4-(1-Methylheptyloxy)-5-[(S)-5'-(1-methylheptyloxy)-2'-hydroxy-4'-(N,N-dimethylamino)-phenylazo]-2-nitrophenol (52a). The amino-nitro compound 51a (357 mg, 1.26 mmol) was dissolved in 33 ml of a 15% concentrated HCl in ethanol solution and was then cooled to 0° C. with an ice-salt bath. To this solution, sodium nitrite (12.5 ml of a 0.1M solution in water) was slowly added dropwise at a rate to maintain the temperature at or below 2° C. (approximately 20 minutes). To this cooled solution was added the dimethyl analine 43a (336 mg, 1.26 mmol) dissolved in 5 ml dichloromethane. Pyridine (3.9 ml) was then slowly added to the solution dropwise at a rate to maintain the temperature below 2° C. (approximately 20 minutes). An additional 15 ml of dichloromethane was added to increase the solubility, the reaction mixture was stirred for one hour at 0° C. and was then allowed to warm to room temperature over an additional 30 minutes. The organic layer was separated, and the aqueous portion was extracted with dichloromethane. The combined organic layers were washed with 5% HCl, followed by brine, and dried over $MgSO_4$. The crude product was adsorbed onto silica gel and purified via flash chromatography with gradual elutions from 85/10/5 to 75/20/5 percentage of (Hex/EtOAc/dichloromethane). Evaporation of the solvent yielded 635 mg (90%) of a metallic green solid.

(S)-4-(1-Methylheptyloxy)-5-[5'-(heptyloxy)-2'-hydroxy-4'-(N,N-dimethylamino)-phenylazo]-2-nitrophenol (52b). Compound 43b (143 mg, 0.57 mmol), compound 51a (161 mg, 0.57 mmol), 0.1 M aqueous sodium nitrite (5.6 ml), and pyridine (1.8 ml) in 15 ml of a 15% HCl/ethanol solution were reacted according to the procedure for compound 52a. The crude product was adsorbed onto silica gel and purified via flash chromatography with gradual elutions from 85/10/5 to 75/20/5 (Hex/EtOAc/dichloromethane). Evaporation of solvent yielded 199 mg (64%) of a metallic green solid.

4-(Heptyloxy)-5-[(S)-5'-(1-methylheptyloxy)-2'-hydroxy-4'-(N,N-dimethylamino)-phenylazo]-2-nitrophenol (52c). Compound 43a (388 mg, 1.46 mmol), compound 51b (392 mg, 1.46 mmol), 0.1M aqueous sodium nitrite (14.5 ml), and pyridine (4.5 ml) in 39 ml of a 15% HCl/ethanol solution were reacted according to the procedure for compound 52a. The crude product was adsorbed onto silica gel and purified via flash chromatography with gradual elutions from 90/5/5 to 75/20/5 (Hex/EtOAc/dichloromethane). Recrystallization from hexanes yielded 370 mg (46%) of a metallic green solid.

para-Nitroanalines

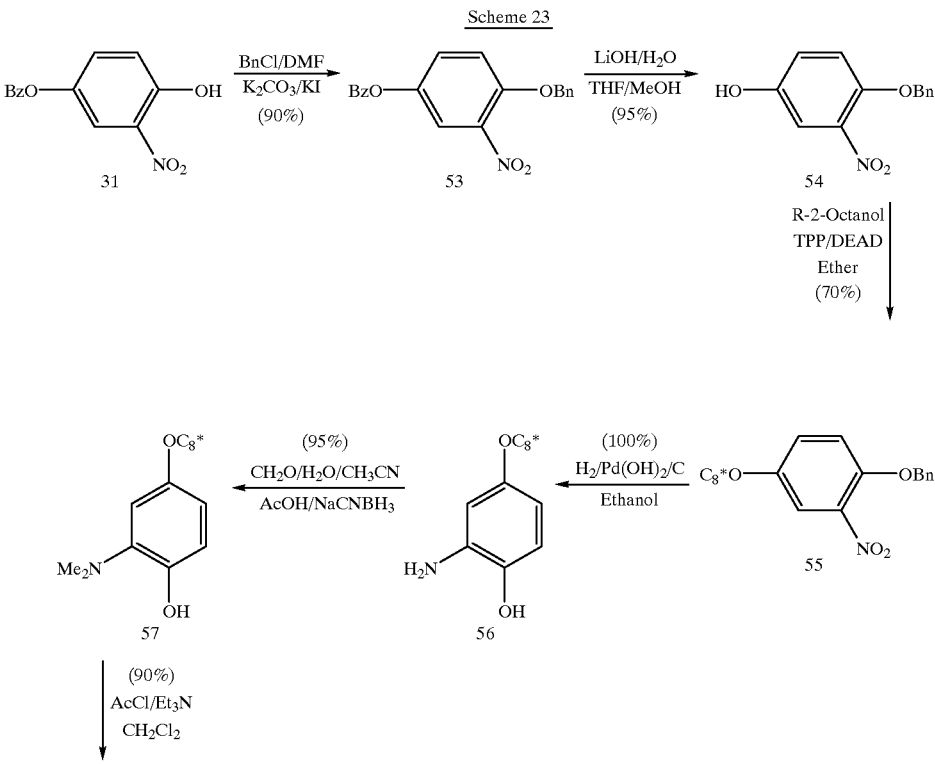

Scheme 23

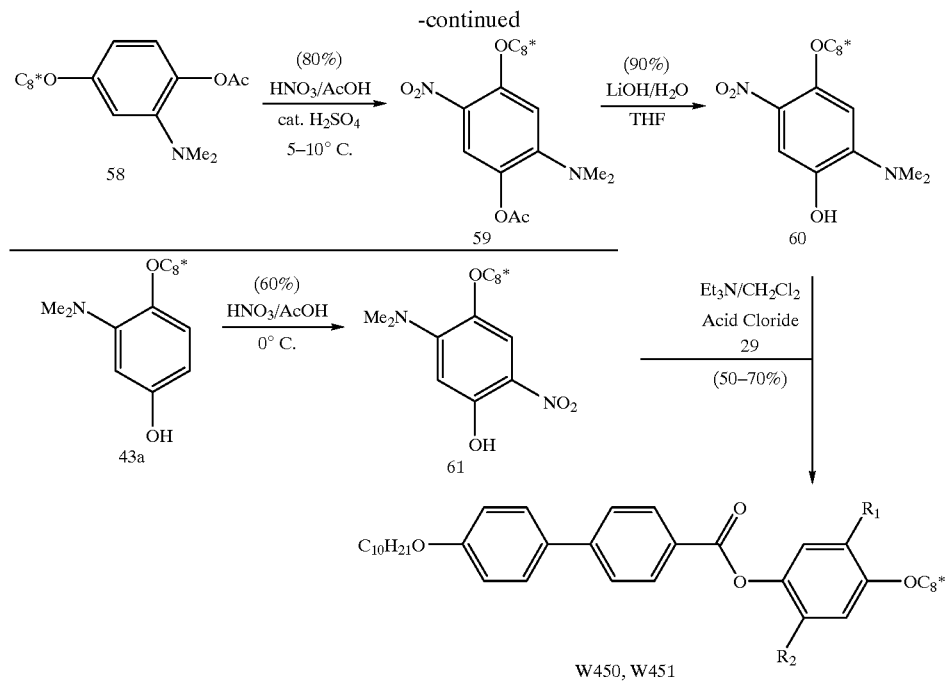

(S)-[41"-(1-Methylheptyloxy)-2"-(N,N-dimethylamino)-5"-nitrophenyl]-4'-decyloxy-4-biphenylcarboxylate (W450). DCC (110 mg, 0 .53 mmol) dissolved in 1 ml dichloromethane was added via syringe, with stirring and under argon, to a solution of phenol 60 (150 mg, 0.48 mmol) carboxylic acid 29 (171 mg, 0.48 mmol), and DMAP (24 mg, 0.19 mmol) in 9 ml dichloromethane. The reaction mixture was stirred for 24 hours and was then treated with 5% HCl. The organic layer was separated, washed with brine, and dried over MgSO$_4$. The crude product was purified via flash chromatography over silica gel with gradual elutions from 98/2–80/20 (v/v, Hex/EtOAc). Evaporation of solvent yielded 141 mg (45%) of a yellow solid which was then precipitated from hexanes.

(S)-[4"-(1-Methylheptyloxy)-5"-(N,N-dimethylamino)-2"-nitrophenyl]-4'-declyoxy-4-biphenylcarboxylate (W451). The acid chloride of compound 29 (120 mg, 0.32 mmol), dissolved in 1 ml dichloromethane, was added via syringe, with stirring and under argon, to a solution of phenol 61 (100 mg, 0.32 mmol) and triethyl amine (39 mg, 0.39 mmol) in 5 ml dichloromethane. The reaction mixture was stirred overnight and was then treated with 5% HCl. Extracted with dichloromethane, the organic layer was washed with brine and dried over MgSO$_4$. The crude product was purified via flash chromatography over silica gel by elution with 15% dichloromethane and 85% (by volume) of a 95/5, v/v, Hex/EtOAc solution. Evaporation of solvent yielded 146 mg (70%) of a yellow solid which was then precipitated from hexanes.

PNA Intermediates 4-(Benzyloxy)-3-nitro-phenylbenzoate (53). Benzyl chloride (5.35 ml, 46.5 mmol) was added to a stirred solution of 31 (6.023 g, 23.2 mmol), potassium carbonate (6.428 g, 46.5 mmol), and potassium iodide (7.72 g, 46.5 mmol) in 100 ml DMF. The reaction mixture was stirred for 24 hours and then water was added (approximately 50 ml). Extracted twice with ethyl acetate, and the combined organic layers were washed with 5% HCl, followed by brine, and dried over MgSO$_4$. The crude product was recrystallized from ethanol to yield 7.245 g (89%) of a yellow solid.

4-(Benzyloxy)-3-nitrophenol (54). Lithium hydroxide monohydrate (5.632 g, 134.2 mmol) was added to a stirred solution of compound 53 (2.343 g, 6.71 mmol) in 150 ml methanol and 50 ml water. THF (50 ml) was added after 20 minutes to increase solubility. The reaction mixture was stirred overnight and was then acidified with concentrated HCl. The reaction mixture was extracted five times with dichloromethane, and the combined organic layers were washed with brine and dried over MgSO$_4$. The crude product was purified via flash chromatography over silica gel with gradual elutions from 80/10–50/50 (Hex/EtOAc). Evaporation of solvent yielded 1.567 g (95%) of a yellow solid.

(S)-4-(1-Methylheptyloxy)-2-(nitro)-1-(benzyloxy)-benzene (55). DEAD (777 mg, 4.46 mmol), TPP (1.171 g, 4.46 mmol), R-2-octanol (511 mg, 3.93 mmol), and compound 54 (875 mg, 3.57 mmol) were reacted according to the procedure for compound 32a. The crude product was purified via flash chromatography over silica gel with gradual elutions from 95/5–80/20 (Hex/EtOAc). Evaporation of solvent yielded 972 mg (76%) of a light yellow oil.

(S)-4-(1-Methylheptyloxy)-2-aminophenol (56). A small scoop of Pear(mans catalyst (Pd(OH)$_2$/C) was added to a solution of compound 55 (1.0 g, 2.8 mmol) in 30 ml ethanol. The flask was evacuated, filled with hydrogen three times, and stirred overnight under an H$_2$ balloon atmosphere. The reaction mixture was filtered through a pad of celite, and evaporation of solvent yielded 639 mg (95%) of a tan solid. The crude product was used without purification.

(S)-4-(1-Methylheptyloxy)-2-(N,N-dimethylamino)-phenol (57) [Borch, R. F. and Hassid, A., *J. Org. Chem.* (1972) 37:1673]. Sodium cyanoborohydride (795 mg, 12.6 mmol) was carefully added at 0° C. to a solution of compound 56 (1.0 g, 4.2 mmol) and 37% aqueous formaldehyde (5.05 ml, 63.2 mmol) in 45 ml acetonitrile. The reaction mixture was stirred for 5 minutes and then 0.4 ml glacial acetic acid was added. The reaction mixture was stirred for one hour at room temperature and then an additional 0.4 ml glacial acetic acid was added. The reaction mixture was stirred for an additional one hour and then excess solvent was evaporated off. The crude product was taken up in ether and treated with 1N KOH. T he reaction mixture was then acidified (pH=5) with concentrated HCl. The reaction mixture was extracted with ether, and the organic layer was washed with brine and dried over MgSO$_4$. Evaporation of solvent yielded 1.053 g (94%) of a red oil. The crude product was used without purification.

(S)-4-(1-Methylheptyloxy)-2-(N,N-dimethylamino)-phenylacetate (58). Acetyl chloride (0.31 ml, 4.3 mmol) was carefully added to a stirred solution of compound 57 (1.05 g, 3.96 mmol) and triethylamine (481 mg, 4.75 mmol) in 40 ml dichloromethane.

The reaction mixture was stirred for 15 minutes and was then treated with 5% HCl. The organic layer was separated, washed with brine, and dried over MgSO$_4$. Evaporation of solvent yielded 1.069 g (88%) of an orange-red oil. The crude product was used without purification.

(S)-4-(1-Methylheptyloxy)-2-(N,N-dimethylamino)-5-nitro-phenylacetate (59). Concentrated nitric acid (0.25 ml) was slowly added at O° C. to a stirred solution of compound 58 in 15 ml glacial acetic acid. The reaction mixture was stirred for five minutes and was then diluted with water. The reaction mixture was extracted with dichloromethane, the organic layer was washed with brine and dried over MgSO$_4$. The crude product was purified via flash chromatography over silica gel with gradual elutions from 90/10–50150 (v/v, Hex/EtOAc). Evaporation of solvent yielded 188 mg (57%) of a viscous orange oil.

(S)-4-(1-Methylheptyloxy)-2-(N,N-dimethylamino)-5-nitro-phenol (60). Lithium hydroxide monohydrate (226 mg, 5.38 mmol) was added to a stirred solution of compound 59 in 15 ml THF and 5 ml water. The reaction mixture was stirred for 15 minutes and was then acidified with concentrated HCl. Extracted with ether, the organic layer was washed with brine and dried over MgSO$_4$. The crude product was purified via flash chromatography over silica gel (80/20, v/v, Hex/EtOAc). Evaporation of solvent yielded 308 mg (92%) of a viscous orange oil. This product rapidly decomposes in chloroform and should be carried on immediately to the next step.

(S)-4-(1-Methylheptyloxy)-5-(N,N-dimethylamino)-2-nitro-phenol (61). Concentrated nitric acid (0.20 ml) was added at 0° C. to a stirred solution of compound 43a in 15 ml glacial acetic acid. The reaction mixture was stirred for 30 seconds until the solution turned dark red. The reaction mixture was then diluted with water and extracted three times with dichloromethane. The combined organic layers were washed with brine and dried over MgSO$_4$. The crude product was purified via flash chromatography over silica gel with gradual elutions from 95/5–90/10 (Hex/EtOAc). Evaporation of solvent yielded 103 mg (61%) of a viscous yellow oil.

Bis-PNA-Biphenylcarboxylate System (S,R)-[2"-(N,N-Dimethylamino)-4"-(1-methylheptyloxy)-5"-nitrophenyl]-2'-(nitro)-4'-(1-methylheptyloxy)-5'-(N,N-dimethylamino)-4-biphenylcarboxylate (W454). DCC (54 mg, 0.26 mmol), carboxylic acid 65 (73 mg, 0.176 mmol), phenol 60 (120 mg, 0.387 mmol), and DMAP (9 mg, 0.07 mmol) in 8 ml dichloromethane were reacted according to the procedure for compound 16. The crude product was purified via flash chromatography over silica gel with gradual elutions from 90/10–50/50 (Hex/EtOAc). Evaporation of solvent yielded 72 mg (58%) of a yellow solid which was then precipitated from hexanes.

PNA Biphenylcarboxylic Acid Fragment (R)-Methyl-3'-(amino)-4'-(1-methylheptyloxy)-4-biphenylcarboxylate (62). A small scoop of 10% Pd/C catalyst was added to a solution of 41c in 15 ml methanol. The flask was evacuated and filled with hydrogen three time. The reaction mixture was stirred three hours under H$_2$ balloon atmosphere and filtered through a pad of celite. Evaporation of solvent yielded 169 mg (100%) of a gray solid. The crude product was used without purification.

(R)-Methyl-3'-(N,N-dimethylamino)-4'-(1-methylheptyloxy)-4-biphenylcarboxylate (63). Sodium cyanoborohydride (202 mg, 3.20 mmol), compound 62 (380 mg, 1.07 mmol), glacial acetic acid (2×0.09 ml), and aqueous formaldehyde (1.28 ml, 16.0 mmol) in 35 ml acetonitrile were reacted according to the procedure for compound 57. Evaporation of solvent yielded 321 mg (78%) of a white solid. The crude product was used without purification.

Scheme 24

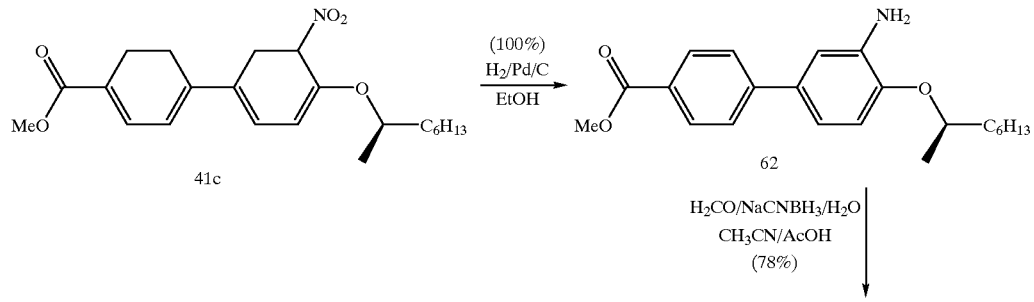

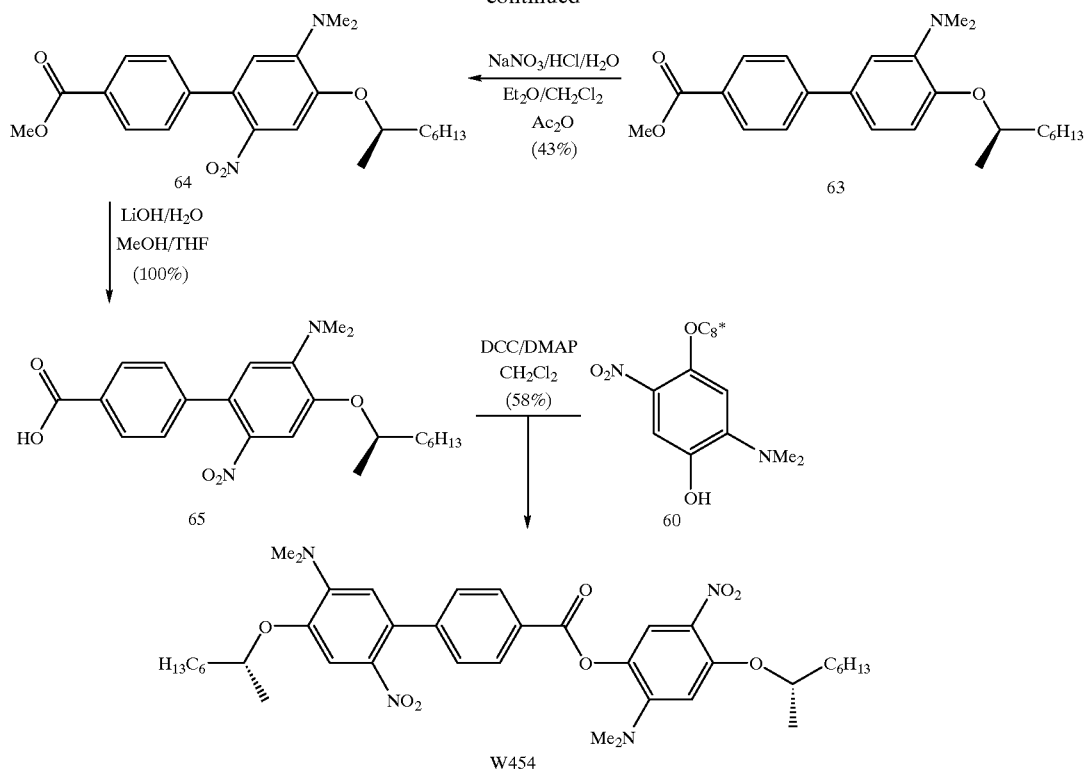

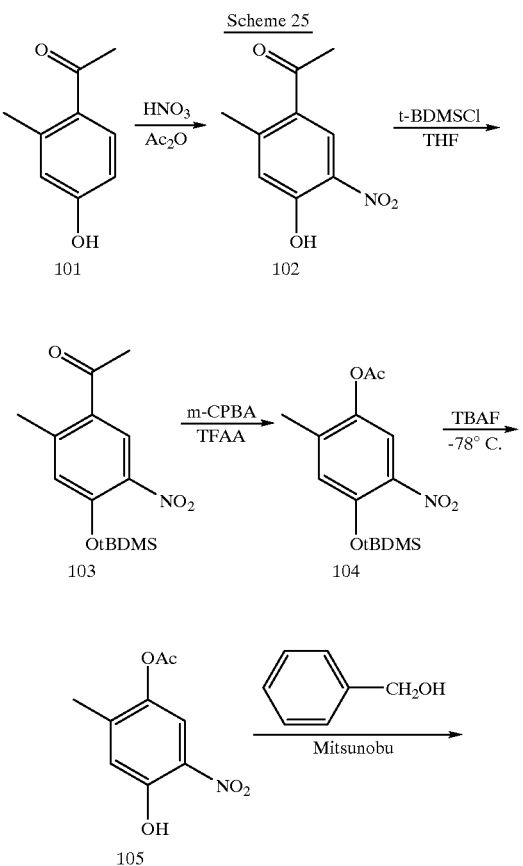

(R)-Methyl-2'-(nitro)-4'-(1-methylheptyloxy)-5'-(N,N-dimethylamino)-4-biphenylcarboxylate (64). Acetic anhydride (3 drops) was added to a stirred solution of compound 63 (75 mg, 0.195 mmol), sodium nitrate (17 mg, 0.205 mmol), water (0.3 ml), concentrated HCl (0.16 ml), dichloromethane (0.5 ml), and ether (3 ml). The reaction mixture was stirred for 15 minutes and then more HCl and Ac$_2$O were added until the solution changed color to a bright yellow. After the color had changed, the reaction mixture was stirred for an additional three hours, and then the organic layer was separated, washed with brine, and dried over MgSO$_4$. The crude product was purified via flash chromatography over silica gel with gradual elutions from 95/5–80/20 (Hex/EtOAc). Evaporation of solvent yielded 36 mg (43%) of a yellow solid.

(R)-2'-(Nitro)-4'-(1-Methylheptyloxy)-5'-(N,N-dimethylamino)-4-biphenylcarboxylic acid (65). Lithium hydroxide monohydrate (96 mg, 2.28 mmol) was added to a stirred solution of compound 64 (49 mg, 0.11 mmol), THF (2 ml), water (3 ml), and methanol (10 ml). The reaction mixture was refluxed overnight and then was acidified with concentrated HCl. The reaction mixture was extracted twice with dichloromethane, the combined organic layers were washed with brine and dried over MgSO$_4$. Evaporation of solvent yielded 47 mg (100%) of a yellow solid. The crude product was carried on without purification.

Example 1.11

The following reaction schemes illustrate and compare the methods for preparation of stilbene derivatives (122 and 140) in which the NO$_2$ group is meta (122) or ortho (140) to the chiral tail or:

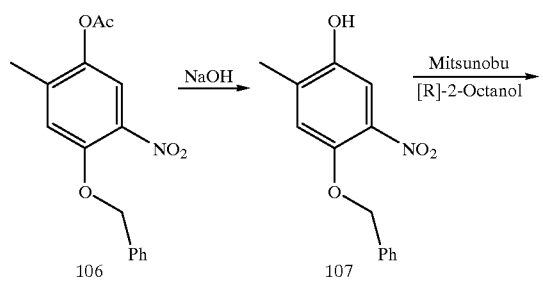
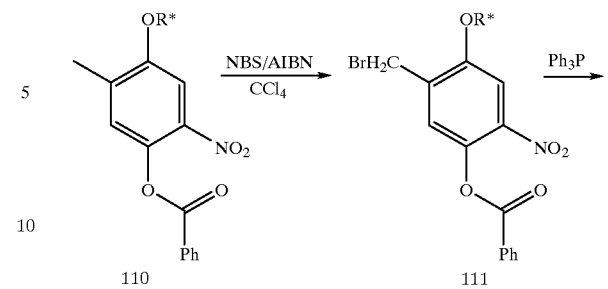
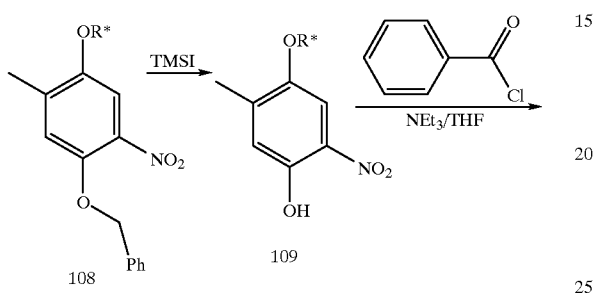
Scheme 26
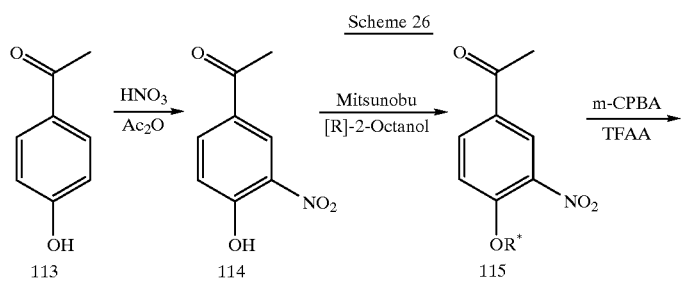
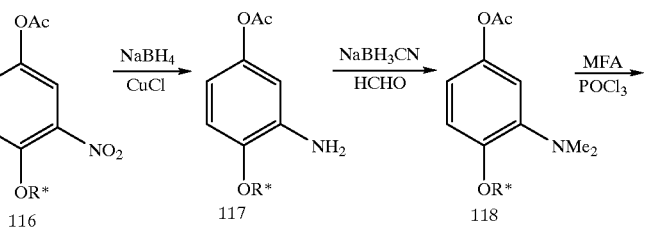
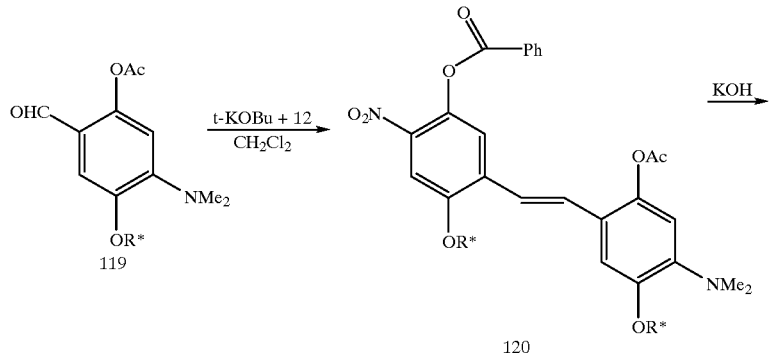

-continued
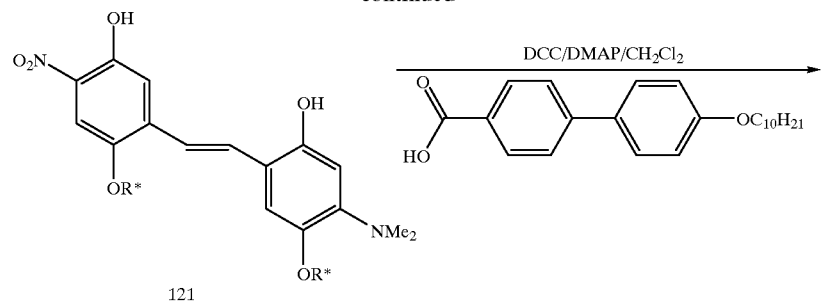
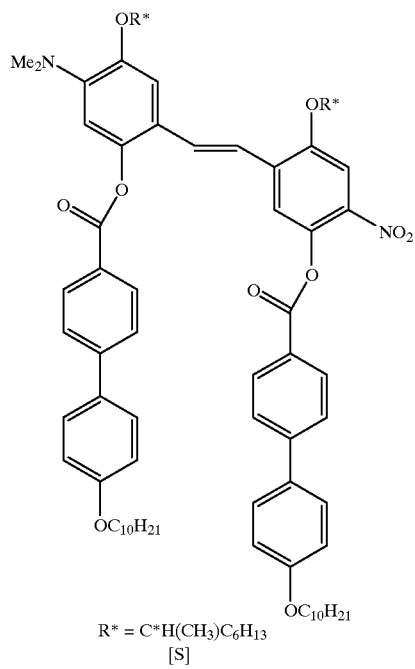
Scheme 27
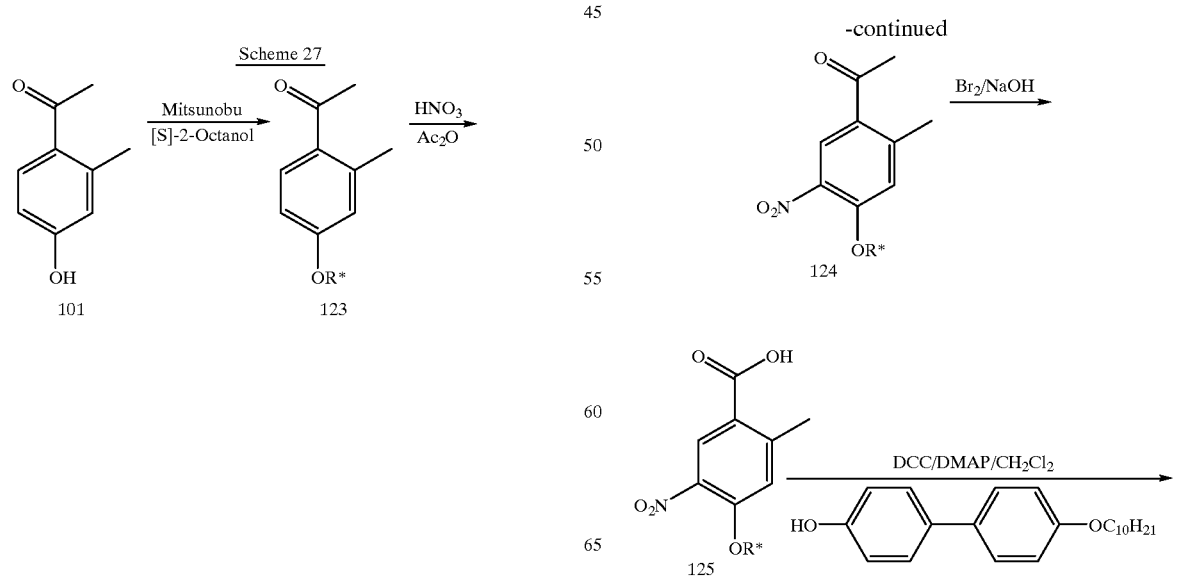

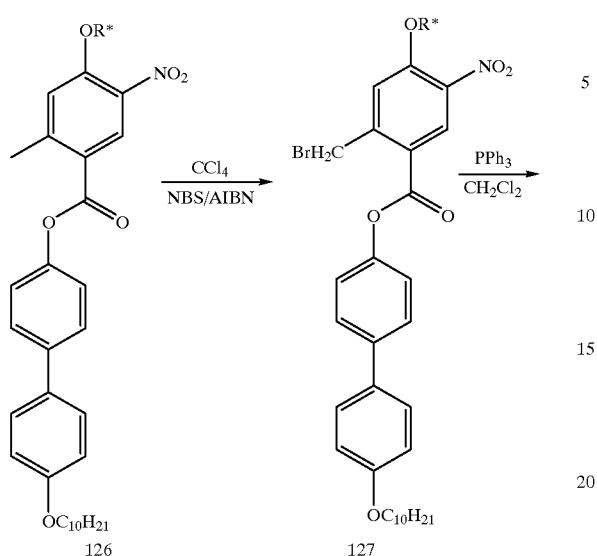
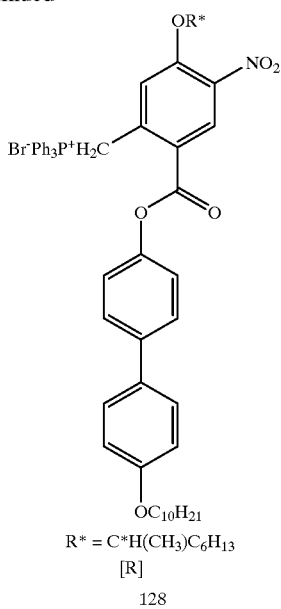
Scheme 28
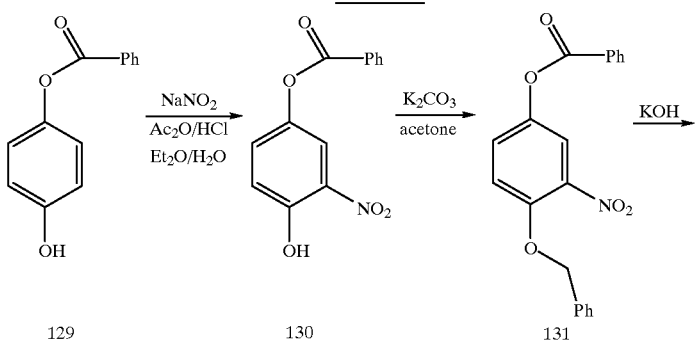
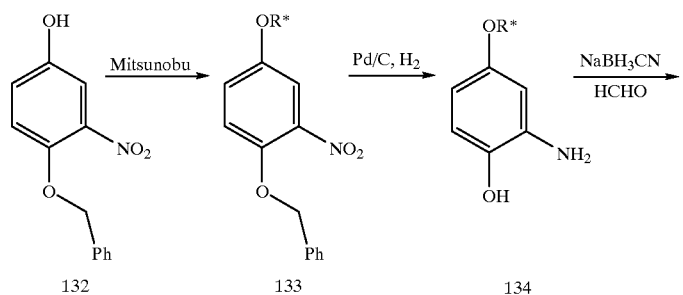

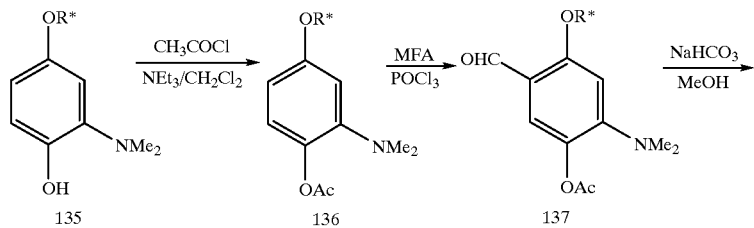
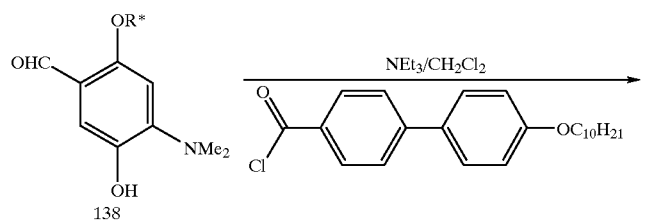
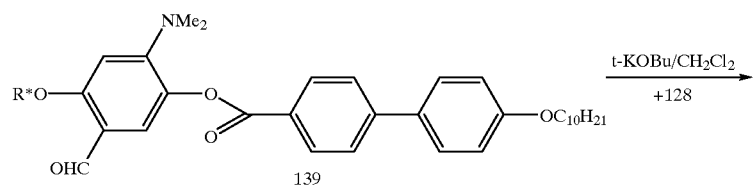
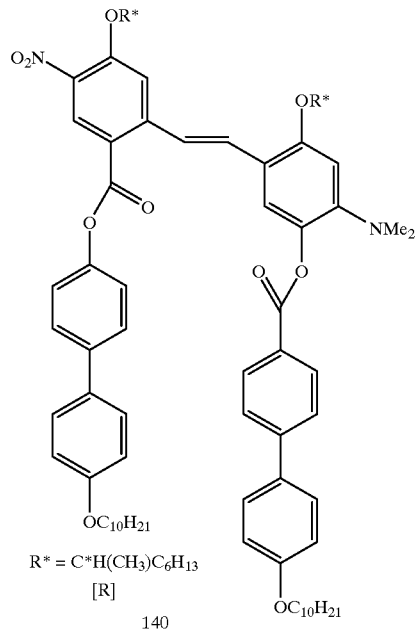
Example 1.12
This example illustrates additional methods for preparation of compounds of this invention. Compound MDW 1115 (153) its analogs and related compounds can be prepared by the reaction of the following scheme:

Scheme 29
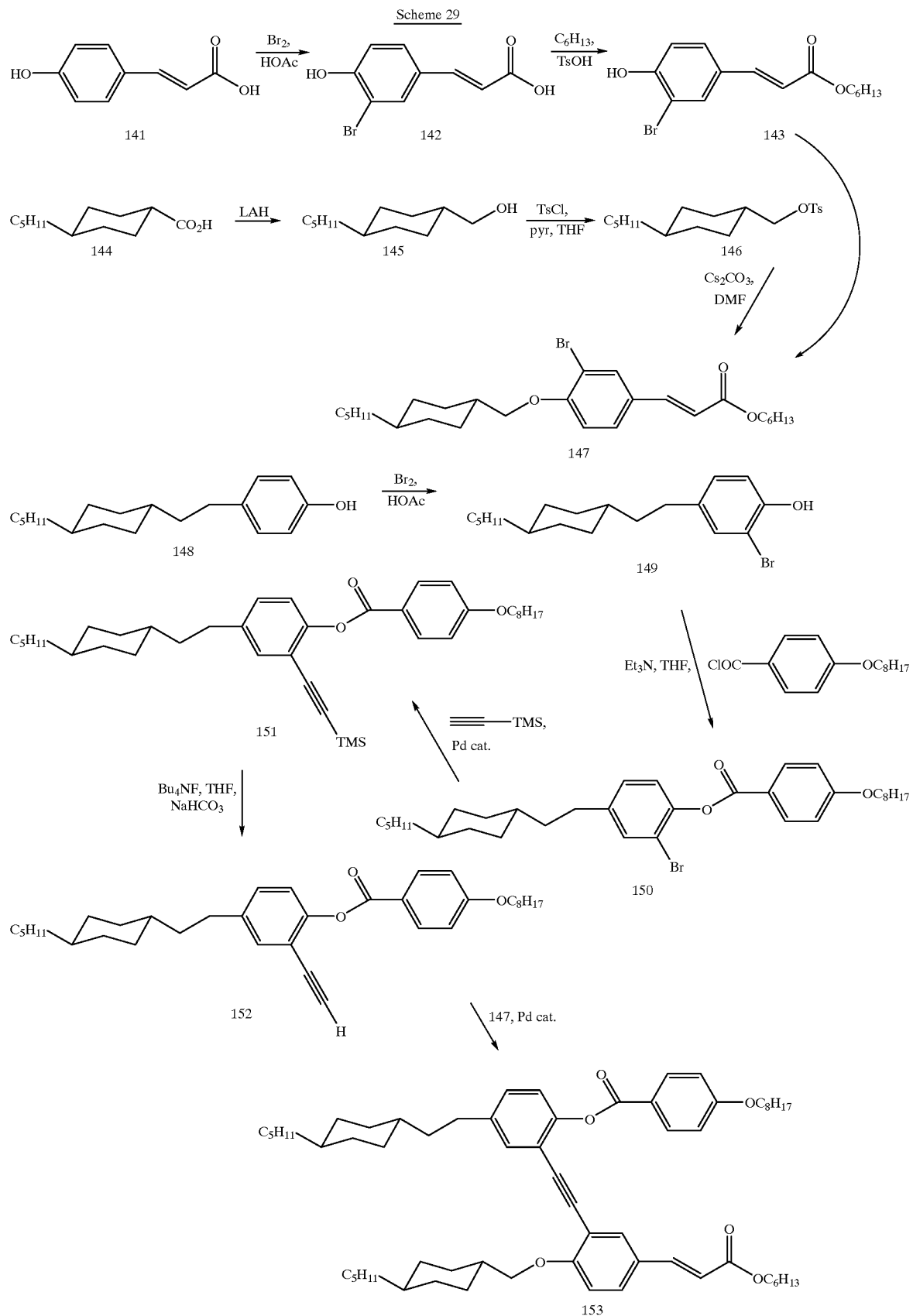

Hexyl 2-Bromo-3-hydroxycinnamate 143. To 2 g (12.2. mmoles) of hydroxycinnamic acid 141 in 60 ml glacial acetic acid was added, dropwise, a solution of 1.85 g (11.6 mmoles) bromine in 5 ml glacial acetic acid. When all the bromine had been added, the acetic acid was distilled off, leaving behind bromoacid 142 as a white melt. To this melt was then added 22 ml hexanol and 50 mg toluenesulfonic acid. The hexanol-water azeotrope (bp. 100° C.) was distilled off dropwise at ambient pressure, until only about half the hexanol remained, and the remainder of the hexanol was then removed in vacuo. The reaction mixture was chromotographed on silica gel using 15% ethyl acetate in haxanes to yield 0.77 g (20%) of bromoester 143 as a white solid.

(trans-4-Pentyl)cyclohexylmethanol 145. To a flask containing 1.91 g (50 mmoles) lithium aluminum hydride and 50 mL ether, cooled to 0° C., was added 5 g (25 mmoles) acid 144. The reaction was warmed to room temperature and allowed to stir overnight, at which time it was again cooled to 0° C. and a reflux condenser was attached. Water (1.91 mL), 15% sodium hydroxide (1.91 mL), and water (5.73 mL) were then added dropwise. When the suspension was white, magnesium sulfate was added as a drying agent, and the solution was filtered. The solvent was removed in vacuo to yield 4.24. g (91%) of alcohol 145.

(trans-4-Pentyl)cyclohexylmethanol toluenesulfonate 146. To a flask containing 4.24 g (23 mmoles) alcohol 145 was added 5.47 g (24 mmoles) toluenesulfonyl chloride and 7 mL anhydrous tetrahydrofuran. The reaction mixture was cooled in an ice bath and 4.6 mL (57 mmoles) pyridine was added. the reaction mixture was stirred 30 min., then allowed to stand at −20° C. for 12 hours. It was then poured into a 10% HCl solution and extracted with 1:1 ethyl acetate:hexane. The solvent was removed in vacuo and the residue was dissolved in tetrahydrofuran. Triethylamine 94 mL) and about 8 drops water were added, and the mixture was allowed to stir for 1 hour. The mixture was checked by TLC (9:1 hexane:ethyl acetate) for remaining tosyl chloride; if any remained, additional drops of water were added and the mixture was stirred for another hour. When no tosyl chloride remained, it was then poured into a 10% HCl solution and extracted with 1:1 ethyl acetate:hexane. The combined organic layers were washed with saturated sodium chloride (brine), then dried over magnesium sulfate. The solvent was removed in vacuo to give 7.8 g (100%) of tosylate 146 as a slightly yellow solid.

Octyl 3-bromo-4-((trans-4-pentyl) cyclohexylmethyleneoxy)cinnamate 147. To a flask containing 300 mg (0.92 mmoles) bromophenol 143 was added 341 mg (1.01 mmoles) tosylate 146,388 mg (1.2 mmoles) anhydrous cesium carbonate, and 1.83 mL anhydrous dimethylformamide. The solution was heated to 100° C. and allowed to stir for 1 hour. It was then cooled to room temperature, poured into a solution of 10% HCl, and extracted with 1:1 hexane:ethyl acetate. The combined organic layers were washed with brine and dried over magnesium sulfate, and the solvent was removed in vacuo. The product was chromatographed on silica gel using 5% ethyl acetate in hexane (product Rf 0.24) to give 139 mg (30%) of the ether 147 as a white solid.

2-Bromo-4-(trans-4-pentylcyclohexyl)ethylene)phenol 149. To a flask containing 5 g (18 mmoles) 4-((trans-4-pentylcyclohexyl)ethylene)phenol 148 was added 90 mL glacial acetic acid. Into a small flask was weighed 2.60 g (16.3 mmoles) bromine, and to this was added 5 mL glacial acetic acid. This solution was added dropwise to the reaction mixture, ensuring that the color of the mixture did not go past yellow-orange. The mixture was stirred an additional hour, then poured into water and ethyl acetate. The organic layer was washed three times with water, then twice with saturated sodium bicarbonate, and finally with brine. The organic layer was dried over sodium sulfate, and the solvent was removed in vacuo. The product was chromatographed on silica gel with 5% ethyl acetate in hexanes to yield 5.39 g (94% based on bromine) of bromophenol 149 as a white solid.

2-Bromo-4-((trans-4-pentylcyclohexyl)ethylene)phenoxy 4'-octyloxybenzoate 150. To a flask containing 1.22 g (4.88 mmoles) 4-octyloxybenzoic acid was added 1.2 mL oxalyl chloride. The reaction mixture was stirred one hour, and then the excess oxalyl chloride was removed in vacuo. To this flask was added phenol 149 and 13 mL anhydrous tetrahydrofuran. The mixture was stirred until homogenous, then 2.96 mL (21 mmoles) freshly distilled dry triethylamine were added. the mixture was allowed to stir 12 hours, then was poured into a solution of 10% HCl, and extracted with 1:1 hexane:ethyl acetate. The combined organic layers were washed with brine and dried over magnesium sulfate, and the solvent was removed in vacuo. The product was chromatographed on silica gel using 5% ethyl acetate in hexane to give 2.16 g (87%) of ester 150 as a white solid.

2-Trimethylsilylacetyleneyl-4-((trans-4-pentylcyclohexyl)ethylene)phenoxy 4'-octyloxybenzoate 151. To a flask containing 1.5 g (2.56 mmoles) of phenyl bromide 150 was added 0.54 mL (3.8 mmoles) trimethylsilylacetylene. 298 mg (0.26 mmoles) tetrakis (triphenylphosphine)palladium, and 13 mL triethylamine. Dry nitrogen was bubbled through the solution for 20 minutes, and it was then refluxed for 18 hours. The black reaction mixture was passed through 3 cm of silica gel, eluting with 10% ethyl acetate in hexanes. The product was chromatographed on silica gel using 5% ethyl acetate in hexanes to give 0.70 g (45%) of the alkyne 151 as a white solid.

2-Acetylenyl-4-((trans-4-pentylcyclohexyl)ethylene) phenoxy 4'-octyloxybenzoate 152. To a flask containing 0.94 g (1.56 mmoles) of silane 151 in 5 mL tetrahydrofuran was added 130 mg (1.56 mmoles) sodium bicarbonate and 3.1 mL (3.1 mmoles) of a 1 M solution of tetrybutylammonium fluoride in tetrahydrofuran. The reaction mixture immediately turned red. It was allowed to stir 15 minutes, at which time it was poured into water and extracted with 1:1 ethyl acetate:hexane. The combined organic layers were washed with brine and dried over magnesium sulfate, and the solvent was removed in vacuo. The product was chromatographed on silica gel using 3% ethyl acetate in hexane to give 400 mg (48%) of acetylene 152 as a white solid. 5-(trans-4'''-Pentylcyclohexyl)ethylene)-2-(4"-Octyloxyphenylcarbonyloxy)-5'-(hexyloxycarbonylvinyl)-2'-(trans-4''''-pentyl)cyclohexylmethyleneoxy)tolane 153. To a flask containing 139 mg (0.27 mmoles) of aryl bromide 147 and 145 mg (0.27 mmoles) acetylene 152 was added 32 mg (0.027 mmoles) tetrakis(triphenylphosphine)palladium and 2 ml diisopropylamine. Dry nitrogen was bubbled through the solution for 15 minutes, and it was then refluxed for 18 hours. The cooled reaction mixture was filtered through 3 cm silica gel using 10% ethyl acetate in hexane a the eluent. The product was then chromatographed on silica gel using 5% ethyl acetate in hexane to yield 112 mg of the dimer 153. This product was recrystallized from a solution of hexane, ethyl acetate, and acetonitrile to give 78 mg (30%) of a slightly yellow solid.

Specific examples of negative birefringement materials that can be made by this method or routine adaptations of this method include MDW 1115 as well as its derivatives 1115A and B illustrated below and MDW 1069 and its derivatives MDW 1069A and B (phase diagrams are given for MDW 1115 and MDW 1115:

VII

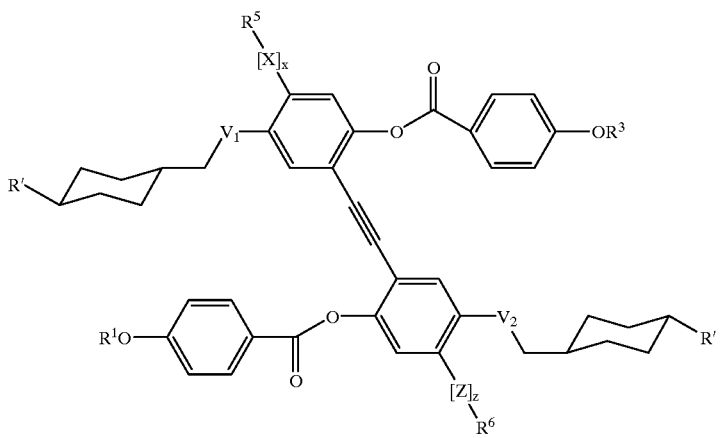

where X, Z, x, z, $R^3$, $R^4$, $R^5$ and $R^6$ are as defined in formula I, $W_1$ and $W_2$, independently of one another, can be —O— or a —CH$_2$— group and R' and R", independently of one another, can be groups as defined for R' and $R^2$. Preferred R' and R" are groups having 1 to about 6 carbon atoms. MDW 1069 has structure VII where x and z are 0, $R^5$ and $R^6$ are H, W, and $W_2$ are —CH$_2$—, $R^3$ and $R^4$ are —C$_8$H$_{17}$, R' and R" are both C$_5$H$_{11}$ and has the phase diagram:

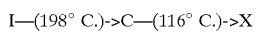

I—(198° C.)->C—(116° C.)->X

<-(1 30° C.)—

MDW 1115 has structure VII where x and z are 0, $R^5$ and $R^6$ are H, W, is —CH$_2$—, $W_2$ is O, $R^3$ is C$_8$H$_{17}$, $R^4$ is —C$_6$H$_{13}$, R' and R" are both C$_5$H$_{11}$ and has the phase diagram:

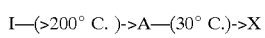

I—(>200° C. )->A—(30° C.)->X

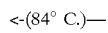

<-(84° C.)—

Figure 5:
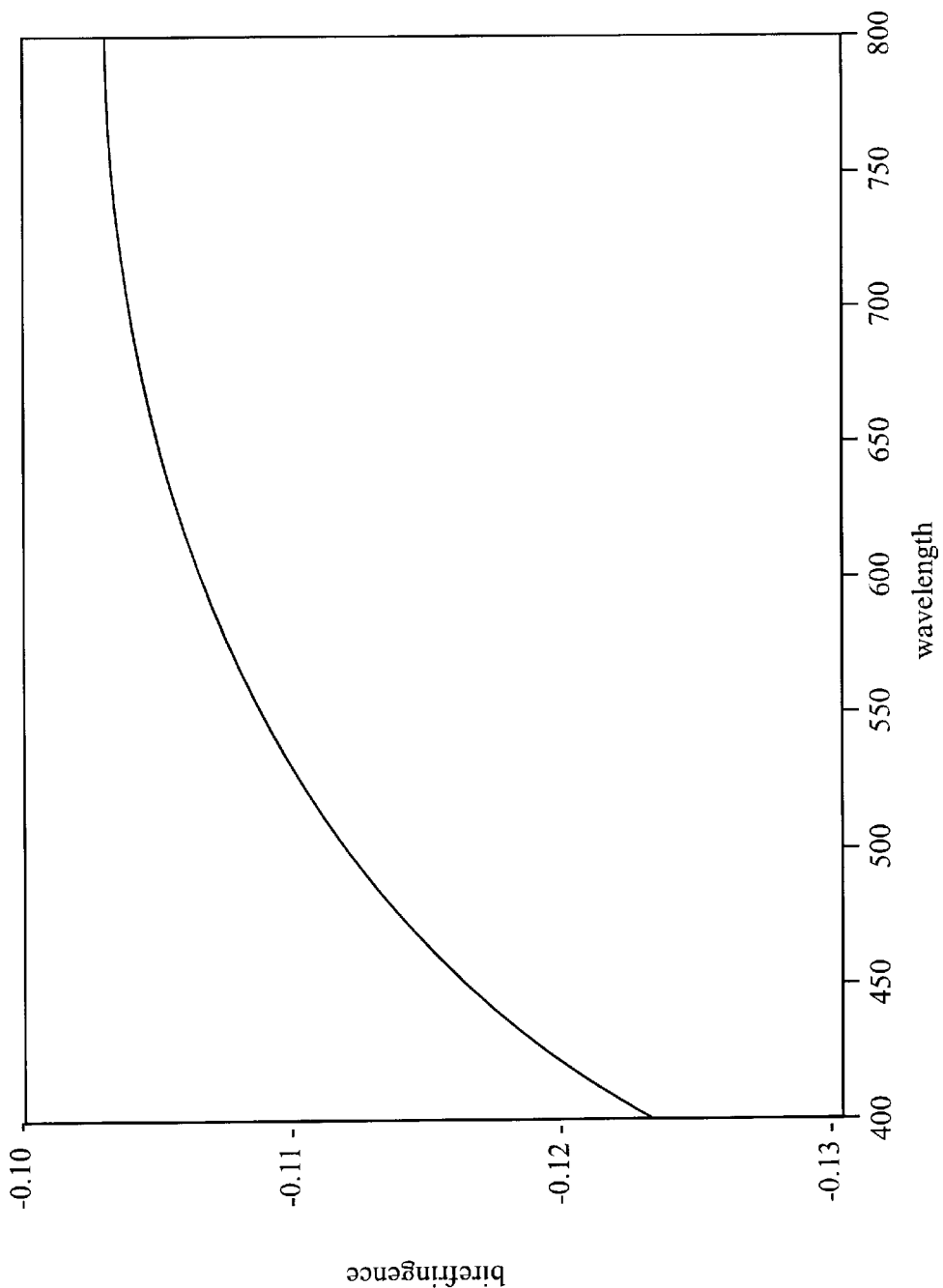
FIG. 5 shows a plot of the birefringence as a function of wavelength illustrating negative birefrigence of MDW 1069.

Other compounds od formula VII that are of interest in this invention are those in which one or both of the groups —[X]$_x$—$R^5$ and —[Z]$_z$—$R^6$ are —C≡C—H or —C≡C—$R^5$, or —C≡C—$R^6$ with preferred $R^5$ and $R^6$ being alkyl or haloalkyl having 1 to about 6 carbon atoms. Of particular interest are those compounds of formula VII where one or both of —[X]$_x$—$R^5$ and —[Z]$_z$—$R^6$ are —C≡C—CH$_3$. FIG. 5 illustrates negative birefringence of MDW 1069 in the visible region.

The specific examples provided herein are illustrative and in no way intended to limit the scope of the invention which is defined by the appended claims.

All of the references cited in this specification are incorporated herein in their entirety by reference.

We claim:
1. A compound of formula I:

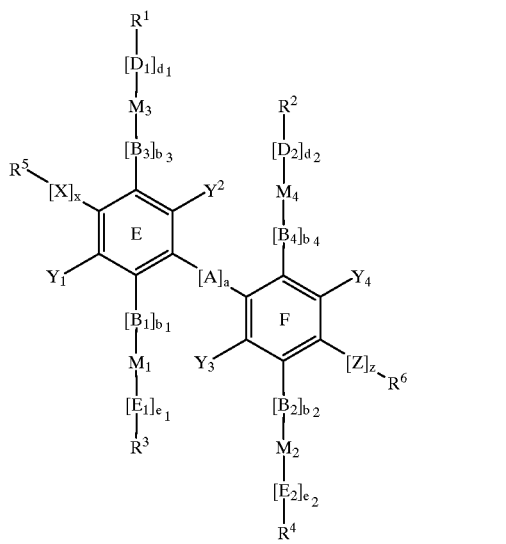

where a is 0 or 1 and A is selected from the group consisting of a —C=C—, —C≡C—, —C≡C—C≡C—, —C=C—C=C—, —C≡C—C=C—C≡C—, —N=N—, —N=NO—, and a —HC=N— group;

$b_1$–$b_4$, independently of one another, are 0 or 1 and $B_1$–$B_4$, independently of one another, are selected from the group consisting of—C=C—, —C≡C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—;

$d_1$ and $d_2$, independently of one another, are 0 or 1 and $D_1$ and $D_2$, independently of one another, are selected from the group consisting of—C=C—, —C≡—C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—;

$e_1$ and $e_2$, independently of one another, are 0 or 1 and $E_1$ and $E_2$, independently of one another, are selected from the group consisting of —C=C—, —C≡C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—;

six-membered aromatic rings E and F, independently of one another, are phenyl rings or phenyl rings in which one or two of the carbon atoms of the ring are replaced with nitrogen atoms and wherein the carbon atoms of the phenyl or nitrogen-containing phenyl rings can be substituted with a halogen, CN, NO$_2$, alkyl, alkenyl, alkynyl, haloalkyl, haloalkenyl, or haloalkynyl groups having from 1 to about 20 carbon atoms;

$Y_1-Y_4$, substituents on rings E and F, independently of one another, are selected from the group consisting of H, halogen, CN, alkyl, alkenyl, alkynyl, haloalkyl, haloalkenyl, and haloalkynyl groups having from 1 to about 20 carbon atoms, wherein one or more non-neighboring CH$_2$ groups in the substituent can be substituted with an O, or S or with a SiR$^A$R$^B$ group, where R$^A$ and R$^B$ are small alkyl or alkenyl groups having from 1 to about 6 carbon atoms, with the proviso that any ring position of aromatic rings E or F that is a nitrogen is not substituted with any of the $Y-Y_4$; x and z, independently of one another are 0 or 1, and X and Z, independently of one another, are selected from the group consisting of electron acceptor groups, electron donor groups, H, halogen, NO$_2$, —C=C—, —C≡C—, —COO—, —OOC—, —CO—, O, S, —COS—, —SCO—, CN, NH, NCH$_3$1, NR', where R' is a small alkyl having 1 to about 3 carbon atoms, NHCO, NCH$_3$CO NR'CO, where R' is a small alkyl having 1 to about 3 carbon atoms, SO, and SO$_2$, with the proviso that any ring position of aromatic rings E or F that is a nitrogen is not substituted with any X or Z, and R$^5$ and R$^6$, independently of one another, are selected from the group consisting of H, halogen, CN, alkyl, alkenyl, alkynyl, haloalkyl, haloalkenyl, and haloalkynyl groups having from 1 to about 20 carbon atoms, wherein one or more non-neighboring CH$_2$ groups in the substituent can be substituted with an O, or S, or with a SiR$^A$R$^B$ group, where R$^A$ and R$^B$ are small alkyl or alkenyl groups having from 1 to about 6 carbon atoms, dependent upon the X or Z group, R$^5$ and/or R$^6$ may be absent; and $M_1-M_4$, independently of one another, are core moieties having from one to four aromatic or non-aromatic rings, optionally separated by up to three linking groups $F_1-F_3$ as in formula:

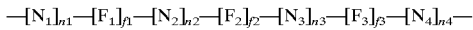

where f1—f4, independently of one another, are 0 or 1, $F_1-F_4$, independently of one another, are selected from the group consisting of —C=C—, —C≡C—, —COO—, —OOC—, —CO—, —O—, —CH$_2$O—, —OCH$_2$—, —CH$_2$—CH$_2$—, —S—, —COS—, —SOC—, —CH=CHCOO—, —OOCCH=CH—, —CH=CHCOS—, and —SOCCH=CH—; and n1–n4, independently of one another, are 0 or 1, and $N_1-N_4$ are selected from the group consisting of aromatic rings having one or two six-member and/or five-membered aromatic rings, which may be fused or non-fused ring systems, or monocyclic or bicyclic alkyl and alkenyl non-aromatic rings having from 5 to about 12 ring carbon atoms wherein in each ring of $N_1-N_4$, one or more of the ring carbons can be substituted with a halogen, CN, small alkyl, alkenyl or alkynyl group having from 1 to about 3 carbon atoms or small halogenated alkyl, halogenated alkenyl or halogenated alkynyl in each ring of $N_1-N_4$ that is aromatic, one or two of the ring carbons can be replaced with a nitrogen (N), in each ring of $N_1-N_4$ that is non-aromatic, one or two non-neighboring CH$_2$ groups can be replaced with an oxygen; and R$^1$, R$^2$, R$^3$, and R$^4$, independently of one another, are selected from the group consisting of linear, branched or cyclic alkyl, alkenyl or alkynyl groups having from 1 to about 20 carbon atoms wherein one or more CH$_2$ groups can be optionally substituted with one or more halogens, or CN groups, or in which one or more non-neighboring CH$_2$ groups can be replaced with an oxygen, a sulfur, or a substituted silyl group, Si(R$^A$)(R$^B$), in which R$^A$ and R$^B$, independently, are alkyl, alkenyl, alkynyl, haloalkyl, haloalkenyl or haloalkynyl groups having from 1 to about 6 carbon atoms.

2. A liquid crystal composition exhibiting negative birefringence which comprises a compound of claim 1.

3. The compound of claim 1 wherein a is 1; and E and F are phenyl rings.

4. The compound of claim 1 wherein:
a is 1;
$B_1$ and $B_2$ are both —O—;
E and F are phenyl rings; and
$M_1$ and $M_2$ are absent.

5. The compound of claim 1 wherein:
a is 1 and A is —C=C—, —C≡C—, —C≡C—C≡C—, —C=C—C=C—, or—C≡C=C≡C—;
$B_1$ and $B_2$ are both —O—;
$B_3$ and $B_4$ are —O—, —CH$_2$—O—, —O—CH$_2$—, —CH$_2$—CH$_2$—, —COO—, —OOC— or —CO—;
E and F are phenyl rings;
x=1, z=1, X and Z, independently of one another, are selected from the group H, NO$_2$, halogen, —CN, —NH—, —C=C—, —C≡C—, and —NR'—, where R' is a small alkyl group having from 1 to about 3 carbon atoms;
$M_1$ and $M_2$ are absent and $M_3$ and $M_4$ are 1,4-cyclohexyl groups, 1,4-cyclohexenyl groups, 1,4-phenyl groups or 1,4'-biphenyl groups; and
$d_1$, $d_2$, $e_1$, and $e_2$ are all zero.

6. The compound of claim 5 wherein a is 1 and A is —C=C—, or —C≡C—.

7. The compound of claim 5 wherein X and Z are selected from H, NO$_2$, —NH—, —C=C—, —C≡C—, and —NR'—, where R' is a small alkyl group having from 1 to about 3 carbon atoms.

8. The compound of claim 5 wherein $M_3$ and $M_4$ are 1,4-cyclohexyl groups, 1,4-cyclohexenyl groups, 1,4-cyclohexyl or 1,4-cyclohexenyl groups in which one or two of the non-neighboring CH$_2$ groups are replaced with an oxygen or 1,4-cyclohexyl or 1,4-cyclohexenyl groups in which one or more of the ring carbons are substituted with a halogen or CN group.

9. The compound of claim 8 wherein $B_3$ and $B_4$ are independently selected from the groups: —O—, —CH$_2$—O—, —O—CH$_2$— and —CH$_2$—CH$_2$—.

10. The compound of claim 5 wherein $M_3$ and $M_4$ are 1,4-cyclohexyl groups.

11. The compound of claim 10 wherein $B_3$ and $B_4$ are independently selected from the groups: —O—, —CH$_2$—O—, —O—CH$_2$— and —CH$_2$—CH$_2$—.

12. The compound of claim 5 wherein $R^1$–$R^4$ are independently selected from the group consisting of hydrogen, an alkyl group, an alkenyl group, an alkynyl group, a halogenated alkyl group, a halogenated alkenyl group or a halogenated alkynyl group.

13. The compound of claim 5 wherein $R^5$ and $R^6$ are independently selected from the group consisting of hydrogen, an alkyl group, an alkenyl group, an alkynyl group, a halogenated alkyl group, a halogenated alkenyl group or a halogenated alkynyl group.

14. The compound of claim 1 wherein X and Z are selected from H, —C=C—, or —C≡C—.

15. The compound of claim 1 wherein $Y_1$–$Y_4$ are all hydrogens.

16. The compound of claim 1 wherein $Y_1$–Y4 are independently selected from the group of hydrogens, alkyl groups or haloalkyl groups.

17. The compound of claim 1 wherein a=1 and A is —C≡C—.

18. The compound of claim 1 wherein z=1 and Z is —C≡C—.

19. The compound of claim 1 wherein:

$b_1$–$b_4$ are all 1;

$B_3$ and $B_4$ are both —O—$CH_2$—;

$B_1$ and $B_2$ are both —O—;

$M_1$ and $M_2$ are absent and $M_3$ and $M_4$ are both cyclohexyl groups; and $R^1$–$R^4$ are alkyl groups having from 1 to 20 carbon atoms.

20. The compound of claim 1 wherein:

a is 1 and A is —C≡C—;

$b_1$–$b_4$ are all 1;

$B_1$ and $B_2$ are both —O—;

$B_3$ and $B_4$ are both —O—$CH_2$—;

E and F are phenyl rings;

$Y_1$–$Y_4$ are all hydrogens;

x=0, z=1 and Z is —C≡C—;

$M_1$ and $M_2$ are absent and $M_3$ and $M_4$ are both 1,4-cyclohexyl groups;

$d_1$, $d_2$, $e_1$, and $e_2$ are all zero;

$R^1$–$R^4$ are alkyl groups having from 1 to 20 carbon atoms; and $R^5$ and $R^6$ are both hydrogens.

21. The compound of claim 20 wherein $R^1$–$R^4$ are alkyl groups having from about 6 to 12 carbon atoms.

22. A liquid crystal composition of exhibiting negative birefringence that comprises a compound of claim 20.

23. The compound of claim 1 wherein $R^1$–$R^4$ are fully or partially fluorinated alkyl, alkenyl or alkynyl groups.

24. The compound of claim 1 where x and z are 1, $R^5$ and $R^6$ are absent and X and Z are selected from the group consisting of hydrogen, an electron donor or an electron acceptor with the proviso that when one of X or Z is an electron donor, the other of X or Z is an electron acceptor.

25. The compound of claim 227 wherein one of X or Z is —$NO_2$ and the other of X or Z is —NR"R'" where R" and R'" are independently selected from the group H or an alkyl group having from 1 to about 6 carbon atoms.

26. The compound of claim 1 wherein $M_1$ has the formula:

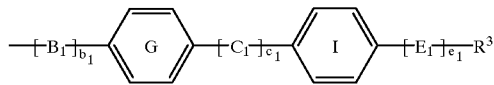

and $M_2$ has the formula:

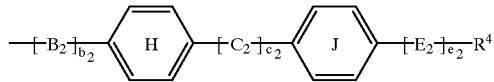

wherein $c_1$ and $c_2$, independently of one another, are 0 or 1 and $C_1$ and $C_2$, independently of one another are selected from the group consisting of —C=C—, —C≡C—, —COO—, —OOC—, —CO—, —O—, —$CH_2$O—, —$OCH_2$—, —$CH_2$—$CH_2$—, —S—, —COS—, —SCO—, —CH=CHCOO—, —OOCCH=CH—, —CH=CHCOS— and —SOCH=CH—; and six-membered aromatic rings G, H, I and J, independently of one another, are 1,4-phenyl rings or 1,4-phenyl rings in which one or two of the carbon atoms of the ring are replaced with nitrogen atoms and in which carbons of the phenyl rings or nitrogen-containing phenyl rings can be substituted with halogens, CN, $NO_2$ or small alkyl, alkenyl, alkynyl, haloalkyl, haloalkenyl or haloalkynyl groups having from 1 to about 3 carbon atoms.

27. The compound of claim 23 wherein six-membered aromatic rings G, H, I and J are all 1,4-phenyl rings.

28. The compound of claim 1 wherein a is 1 and A is —N=N—.

29. The compound of claim 28 wherein one of X or Z is —$NO_2$ and the other of X or Z is —NR"R'" where R" and R'" are independently selected from the group H or an alkyl group having from 1 to about 6 carbon atoms.

30. The compound of claim 1 wherein a=1 and A is —C=C—.

31. An electrooptical device employing a liquid crystal composition of claim 2.

32. A liquid crystal composition comprising a rod-like liquid crystal molecule exhibiting negative birefringence and having a liquid crystal core and one or more tail groups wherein the liquid crystal core comprises one or more aromatic rings.

33. The liquid crystal composition of claim 32 having a nematic phase.

34. The liquid crystal composition of claim 32 having a smectic phase.

35. The LC composition of claim 32 that is a ferroelectric LC composition.

36. An electrooptical device employing a liquid crystal composition of claim 32.

37. A liquid crystal composition comprising a rod-like liquid crystal molecule that is a dimer exhibiting negative birefringence and which comprises liquid crystal monomers each of which has a liquid crystal core comprising one or more aromatic rings.

38. The liquid crystal composition of claim 37 wherein the LC monomers are linked through a high birefringence moiety.

39. An electrooptical device employing a liquid crystal composition of claim 37.

* * * * *

UNITED STATES PATENT AND TRADEMARK OFFICE
CERTIFICATE OF CORRECTION

PATENT NO.   : 6,139,771
DATED        : October 31, 2000
INVENTOR(S)  : Walba et al.

It is certified that error appears in the above-identified patent and that said Letters Patent is hereby corrected as shown below:

Column 1,
Line 5, please add the following section:
-- CROSS REFERENCE TO RELATED APPLICATTIONS
This application claims priority to United States provisional application Serial No. 60/015,376, filed April 5, 1996 --
Line 29, delete "(An)" and replace with -- $\Delta$n --.
Line 34, insert -- along -- between "refraction" and "its".

Column 5,
Line 66, delete "n" and replace with -- $\hat{n}$ --.

Column 6,
Line 56, delete "(An)" and replace with -- $\Delta$n --.

Column 8,
Line 14, delete "$CH_2$" and replace with -- $CH_2O$ --.

Column 9,
Line 16, please insert -- ( -- before "preferred".
Line 38, please replace "RF" with -- $R_F$ --.
Line 63, delete "replace" and insert -- replaced --.

Column 10,
Line 47, after "$B_2$". delete "$d_3$" and replace with -- $d_1$ --.

Column 12,
Line 33, delete "$R_3$ and $R_4$" and replace with -- $R^3$ and $R^4$ --.

Column 15,
Line 65, delete "n," and replace with -- $n_o$ --.
Line 66, delete "n," and replace with -- $n_e$ --.

Column 18,
Between Lines 13 and 19, delete the formulas and replace with:

```
  --R-D-M-B-Ph-B'-M'-E-R'              R-D-M-B-Cyc-B'-M'-E-R'
        /                                    /
       A                   and              A
        \                                    \
  R-D-M-B-Ph-B'-M'-E-R'                R-D-M-B-Cyc-B'-M'-E-R'--
```

Page 1 of 5

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 19,
Line 19, group A, delete "$CH_2=CH_2$" and replace with -- $CH_2=CH$ --.
Line 28, group B, delete "alkyl-=-" and replace with -- alkyl -≡- --.
Line 31, group B, delete "$CH_2=CH_2-CH_2)_m$" and replace with -- $CH_2=CH-(CH_2)_n$ --.
Line 37, group B, delete "$R_1$" and replace with -- R --.
Line 54, group D, delete "$CH_2=CH_2$" and replace with -- $CH_2=CH$ --.
Line 62, group E, delete "$CH_2=CH_2 (CH_2)_{m-S-}$" and replace with -- $CH_2=CH-(CH_2)_n-S-$ --.

Column 20,
Lines 6 through 20, delete "$R_1$" and replace -- R --
Lines 22 and 36, insert -- is -- between "n+m" and "less".
Line 25, delete "$(CH_2)\alpha-$" and replace with -- $(CH_2)_n$ --.
Line 27, delete "$CH_2=CH_2$" and replace with -- $CH_2=CH$ --.
Line 31 replace "$(CH_2)-$" with -- $(CH_2)_m-$ --.     1
Line 33, replace "$(CH_2)-$" with -- $(CH_2)_n-$ --.
Lines 43-66, replace all 15 instances of "$\leqq$" with -- $\leq$ --.

Column 22,
Line 13, replace "$\leqq$" with -- $\leq$ --.

Columns 23 and 24,
Scheme 3, insert -- 72 -- under the phase diagram.

Columns 25 and 26,
Following the structure entitled "Tails", please insert the following:

| Compound | $R_1$ | $R_2$ | $R_3$ |
|---|---|---|---|
| 83 | $C_6$ | $C_8$ | $C_{10}$ |
| 84 | $C_6$ | $C_8$ | LA |
| 85 | $C_7$ | $C_8$ | LA |
| 86 | $C_6$ | $C_7$ | LA-- |

Column 33,
Line 16, delete "1 unit" and replace with -- β unit --.

Column 34,
Line 48, delete "of $\cong$" and replace with -- of $\simeq$ --.
Line 65, delete "$\cong$" and replace with -- $\simeq +$ --.
Line 66, delete "$\cong$" and replace with -- $\approx$ --.

Column 35,
Line 67, delete "$\cong$" and replace with -- $\approx$ --.

UNITED STATES PATENT AND TRADEMARK OFFICE
CERTIFICATE OF CORRECTION

PATENT NO.   : 6,139,771
DATED        : October 31, 2000
INVENTOR(S)  : Walba et al.

It is certified that error appears in the above-identified patent and that said Letters Patent is hereby corrected as shown below:

Column 37,
Line 5, delete the structure following "LA =" and replace with:

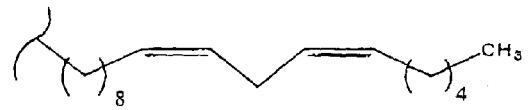

Line 47, delete "C" and replace with -- C --.

Column 38,
Line 66, delete "DR!" and replace with -- DR1 --.

Column 39,
Lines 16 through 34, delete the structure for Scheme 12 and replace with:

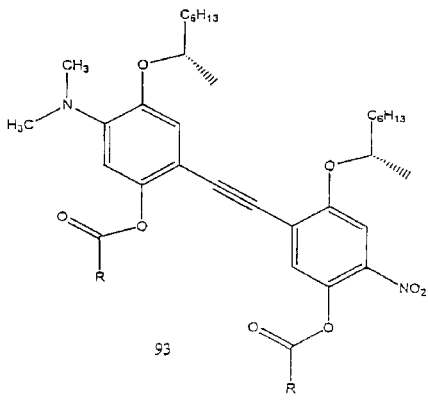

Column 60,
Line 36, insert -- ( -- between "g" and "565".

Column 71,
Line 11, delete "1'." and replace with -- 1", --.

Column 72,
Line 45, delete "(Sob)" and replace with -- (50b) --.

Column 75,
Line 29, delete "[41' " and replace with -- [4" --.

Column 76,
Line 57, delete "Pear(mans" and replace with -- Pearlmans --.

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 77,
Line 31, delete "O°C " and replace with -- 0°C --.
Line 37, delete "50150" and replace with -- 50/50 --.

Column 91,
Line 12, delete "haxanes" and replace with -- hexanes --.
Line 29, delete "added. the" and replace with -- added. The --.
Line 33, insert -- ( -- before "94".

Column 92,
Line 14, delete "added. the" and replace with -- added. The --.
Line 46, "5-(trans-" begins a new paragraph.

Column 93,
Lines 30 and 41, delete "W," and replace with -- $W_1$ --.
Line 52, delete "od" and replace with -- of --.

Column 95,
Line 27, delete "Y-$Y_4$" and replace with -- $Y_1$-$Y_4$ --.

Column 94,
Line 63, delete "—C≡—C—" and replace with -- —C≡C— --.

Column 95,
Line 32, delete "$NCH_3$1" and replace with -- $NCH_3$ --.
Line 34, delete "$NCH_3$CO NR'CO," and replace with --$NCH_3$CO,NR'CO --.

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 97,
Line 16, delete "Y4" and replace with -- $Y_4$ --.
Line 54, delete "arc" and replace with -- are --.
Line 59, delete "227" and replace with -- 21 --.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,139,771
DATED        : October 31, 2000
INVENTOR(S)  : Walba et al.

It is certified that error appears in the above-identified patent and that said Letters Patent is hereby corrected as shown below:

Column 1,
Line 5, please add the following section:
-- CROSS REFERENCE TO RELATED APPLICATTIONS
This application claims priority to United States provisional application Serial No. 60/015,376, filed April 5, 1996 --
Line 29, delete "(An)" and replace with -- $\Delta$n --.
Line 34, insert -- along -- between "refraction" and "its".

Column 5,
Line 66, delete "n" and replace with -- $\hat{n}$ --.

Column 6,
Line 56, delete "(An)" and replace with -- $\Delta$n --.

Column 8,
Line 14, delete "$CH_2$" and replace with -- $CH_2O$ --.

Column 9,
Line 16, please insert -- ( -- before "preferred".
Line 38, please replace "RF" with -- $R_F$ --.
Line 63, delete "replace" and insert -- replaced --.

Column 10,
Line 47, after "$B_2$". delete "$d_3$" and replace with -- $d_1$ --.

Column 12,
Line 33, delete "$R_3$ and $R_4$" and replace with -- $R^3$ and $R^4$ --.

Column 15,
Line 65, delete "n," and replace with -- $n_o$ --.
Line 66, delete "n," and replace with -- $n_e$ --.

Column 18,
Between Lines 13 and 19, delete the formulas and replace with:

```
      --R-D-M-B-Ph-B'-M'-E-R'             R-D-M-B-Cyc-B'-M'-E-R'
                /                                    /
               A                and                 A
              /                                    /
      R-D-M-B-Ph-B'-M'-E-R'             R-D-M-B-Cyc-B'-M'-E-R'--
```

UNITED STATES PATENT AND TRADEMARK OFFICE
CERTIFICATE OF CORRECTION

PATENT NO.   : 6,139,771
DATED        : October 31, 2000
INVENTOR(S)  : Walba et al.

It is certified that error appears in the above-identified patent and that said Letters Patent is hereby corrected as shown below:

Column 19,
Line 19, group A, delete "$CH_2=CH_2$" and replace with -- $CH_2=CH$ --.
Line 28, group B, delete "alkyl-=-" and replace with -- alkyl -≡- --.
Line 31, group B, delete "$CH_2=CH_2-CH_2)_m$" and replace with -- $CH_2=CH-(CH_2)_n$ --.
Line 37, group B, delete "$R_1$" and replace with -- R --.
Line 54, group D, delete "$CH_2=CH_2$" and replace with -- $CH_2=CH$ --.
Line 62, group E, delete "$CH_2=CH_2 -(CH_2)_{m-S-}$" and replace with -- $CH_2=CH-(CH_2)_n-S-$ --.

Column 20,
Lines 6 through 20, delete "$R_1$" and replace -- R --
Lines 22 and 36, insert -- is -- between "n+m" and "less".
Line 25, delete "$(CH_2)\alpha-$" and replace with -- $(CH_2)_n$ --.
Line 27, delete "$CH_2=CH_2$" and replace with -- $CH_2=CH$ --.
Line 31 replace "$(CH_2)-$" with -- $(CH_2)_m-$ --.    1
Line 33, replace "$(CH_2)-$" with -- $(CH_2)_n-$ --.
Lines 43-66, replace all 15 instances of "$\cong$" with -- $\leq$ --.

Column 22,
Line 13, replace "$\cong$" with -- $\leq$ --.

Columns 23 and 24,
Scheme 3, insert -- 72 -- under the phase diagram.

Columns 25 and 26,
Following the structure entitled "Tails", please insert the following:

| Compound | $R_1$ | $R_2$ | $R_3$ |
|---|---|---|---|
| 83 | $C_6$ | $C_8$ | $C_{10}$ |
| 84 | $C_6$ | $C_8$ | LA |
| 85 | $C_7$ | $C_8$ | LA |
| 86 | $C_8$ | $C_7$ | LA-- |

Column 33,
Line 16, delete "1 unit" and replace with -- β unit --.

Column 34,
Line 48, delete "of $\cong$" and replace with -- of $\approx$ --.
Line 65, delete "$\cong$" and replace with -- $\approx +$ --.
Line 66, delete "$\cong$" and replace with -- $\approx$ --.

Column 35,
Line 67, delete "$\cong$" and replace with -- $\approx$ --.

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 37,
Line 5, delete the structure following "LA =" and replace with:

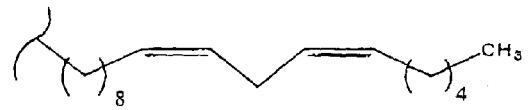

Line 47, delete "C" and replace with -- C* --.

Column 38,
Line 66, delete "DR!" and replace with -- DR1 --.

Column 39,
Lines 16 through 34, delete the structure for Scheme 12 and replace with:

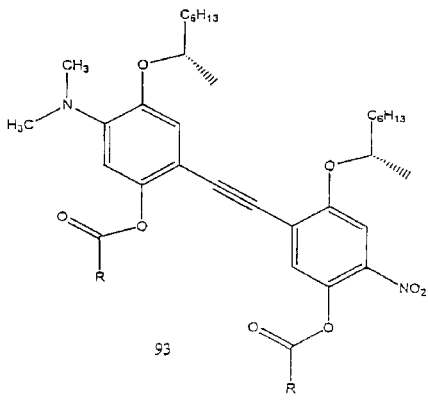

Column 60,
Line 36, insert -- ( -- between "g" and "565".

Column 71,
Line 11, delete "1'," and replace with -- 1", --.

Column 72,
Line 45, delete "(Sob)" and replace with -- (50b) --.

Column 75,
Line 29, delete "[41' " and replace with -- [4" --.

Column 76,
Line 57, delete "Pear(mans" and replace with -- Pearlmans --.

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 77,
Line 31, delete "O°C " and replace with -- 0°C --.
Line 37, delete "50150" and replace with -- 50/50 --.

Column 91,
Line 12, delete "haxanes" and replace with -- hexanes --.
Line 29, delete "added. the" and replace with -- added. The --.
Line 33, insert -- ( -- before "94".

Column 92,
Line 14, delete "added. the" and replace with -- added. The --.
Line 46, "5-(trans-" begins a new paragraph.

Column 93,
Lines 30 and 41, delete "W," and replace with -- $W_1$ --.
Line 52, delete "od" and replace with -- of --.

Column 95,
Line 27, delete "Y-$Y_4$" and replace with -- $Y_1$-$Y_4$ --.

Column 94,
Line 63, delete "—C≡—C—" and replace with -- —C≡C— --.

Column 95,
Line 32, delete "$NCH_3$1" and replace with -- $NCH_3$ --.
Line 34, delete "$NCH_3$CO NR'CO," and replace with --$NCH_3$CO,NR'CO --.

UNITED STATES PATENT AND TRADEMARK OFFICE
CERTIFICATE OF CORRECTION

PATENT NO. : 6,139,771
DATED : October 31, 2000
INVENTOR(S) : Walba et al.

It is certified that error appears in the above-identified patent and that said Letters Patent is hereby corrected as shown below:

Column 97,
Line 16, delete "Y4" and replace with -- $Y_4$ --.
Line 54, delete "arc" and replace with -- are --.
Line 59, delete "227" and replace with -- 21 --.

This certificate supersedes Certificate of Correction issued August 17, 2004.

Signed and Sealed this

Thirtieth Day of November, 2004

JON W. DUDAS
*Director of the United States Patent and Trademark Office*